United States Patent
Minshull et al.

(10) Patent No.: US 9,206,433 B2
(45) Date of Patent: Dec. 8, 2015

(54) METHODS, COMPOSITIONS AND KITS FOR A ONE-STEP DNA CLONING SYSTEM

(71) Applicant: DNA Twopointo, Inc., Menlo Park, CA (US)

(72) Inventors: Jeremy Minshull, Los Altos, CA (US); Jon Ness, Redwood City, CA (US); Elias Theodorou, Hamden, CT (US)

(73) Assignee: DNA Twopointo, Inc., Menlo Park, CA (US)

(*) Notice: Subject to any disclaimer, the term of this patent is extended or adjusted under 35 U.S.C. 154(b) by 174 days.

(21) Appl. No.: 13/875,277

(22) Filed: May 1, 2013

(65) Prior Publication Data

US 2014/0329233 A1 Nov. 6, 2014

(51) Int. Cl.
*C12N 15/63* (2006.01)
*C12N 15/64* (2006.01)
*C12N 15/66* (2006.01)

(52) U.S. Cl.
CPC .............. *C12N 15/64* (2013.01); *C12N 15/66* (2013.01)

(58) Field of Classification Search
CPC ............................... C12N 15/64; C12N 15/87
USPC .............................................. 435/320.1, 440
See application file for complete search history.

(56) References Cited

U.S. PATENT DOCUMENTS

| | | | | |
|---|---|---|---|---|
| 5,888,732 | A * | 3/1999 | Hartley et al. | 435/6.18 |
| 2003/0118994 | A1* | 6/2003 | Blackburn et al. | 435/6 |
| 2005/0069929 | A1 | 3/2005 | Chestnut et al. | |
| 2009/0298088 | A1* | 12/2009 | Belyaev et al. | 435/7.1 |
| 2009/0328244 | A1* | 12/2009 | Chesnut et al. | 800/13 |
| 2010/0291633 | A1 | 11/2010 | Selmer et al. | |
| 2011/0244521 | A1* | 10/2011 | Nagai et al. | 435/91.2 |
| 2011/0263024 | A1* | 10/2011 | Marillonnet et al. | 435/440 |
| 2012/0259607 | A1* | 10/2012 | Hillson | 703/11 |
| 2012/0301873 | A1* | 11/2012 | Sassano et al. | 435/6.1 |
| 2013/0267021 | A1* | 10/2013 | Weber et al. | 435/320.1 |

FOREIGN PATENT DOCUMENTS

WO WO2011/154147 * 12/2011

OTHER PUBLICATIONS

Engler et al., A One Pot, One Step, Precision Cloning Method with High Throughput Capability. PLoS ONE 3 (11) : e3647 pp. 1-7 (2008).*
Engler et al., Golden Gate Shuffling: A One-Pot DNA Shuffling Method Based on Type IIs Restriction Enzymes. PLoS ONE 4 (5) : e5553 pp. 1-9 (2009).*
Perkin Elmer Cetus [GeneAmp DNA amplification kit—Product Insert (1988)].*
Reyrat et al.,Counterselectable Markers: Untapped Tools for Bacterial Genetics and Pathogenesis. Infection and Immunity 66(9) : 4011 (1998).*
Szybalski et al. Class IIs restriction enzymes—a review. Gene 100 :13 (1991).*
Stratagene Catalog [p. 39 (1988) ].*
Weber et al., A Modular Cloning System for Standardized Assembly of Multigene Constructs. PLoS ONE 6 (2) : e16765, pp. 1-11 (2011).*
Padgett et al. Creating seamless junctions independent of restriction sites in PCR cloning. Gene 168 : 31 (1996).*

* cited by examiner

*Primary Examiner* — Ethan C Whisenant
(74) *Attorney, Agent, or Firm* — Alston & Bird LLP

(57) ABSTRACT

Methods and kits for joining two or more polynucleotides to form a product polynucleotide are provided. A mixture contains a first polynucleotide comprising a selectable marker. The mixture further contains a second polynucleotide comprising a first typeIIs recognition sequence and a second typeIIs recognition sequence. The second polynucleotide is other than the first polynucleotide. The mixture further contains a first typeIIs restriction endonuclease that cleaves the first typeIIs recognition sequence to produce a first end, a second typeIIs restriction endonuclease that cleaves the second typeIIs recognition sequence to produce a second end, and a DNA ligase. The first end is not compatible with the second end. The combined actions of the enzymes in the mixture join the first polynucleotide to the second polynucleotide forming a product polynucleotide, which is obtained by transforming the mixture into a host cell.

16 Claims, 11 Drawing Sheets

METHODS, COMPOSITIONS AND KITS FOR A ONE-STEP DNA CLONING SYSTEM

1. FIELD

Figure 1:
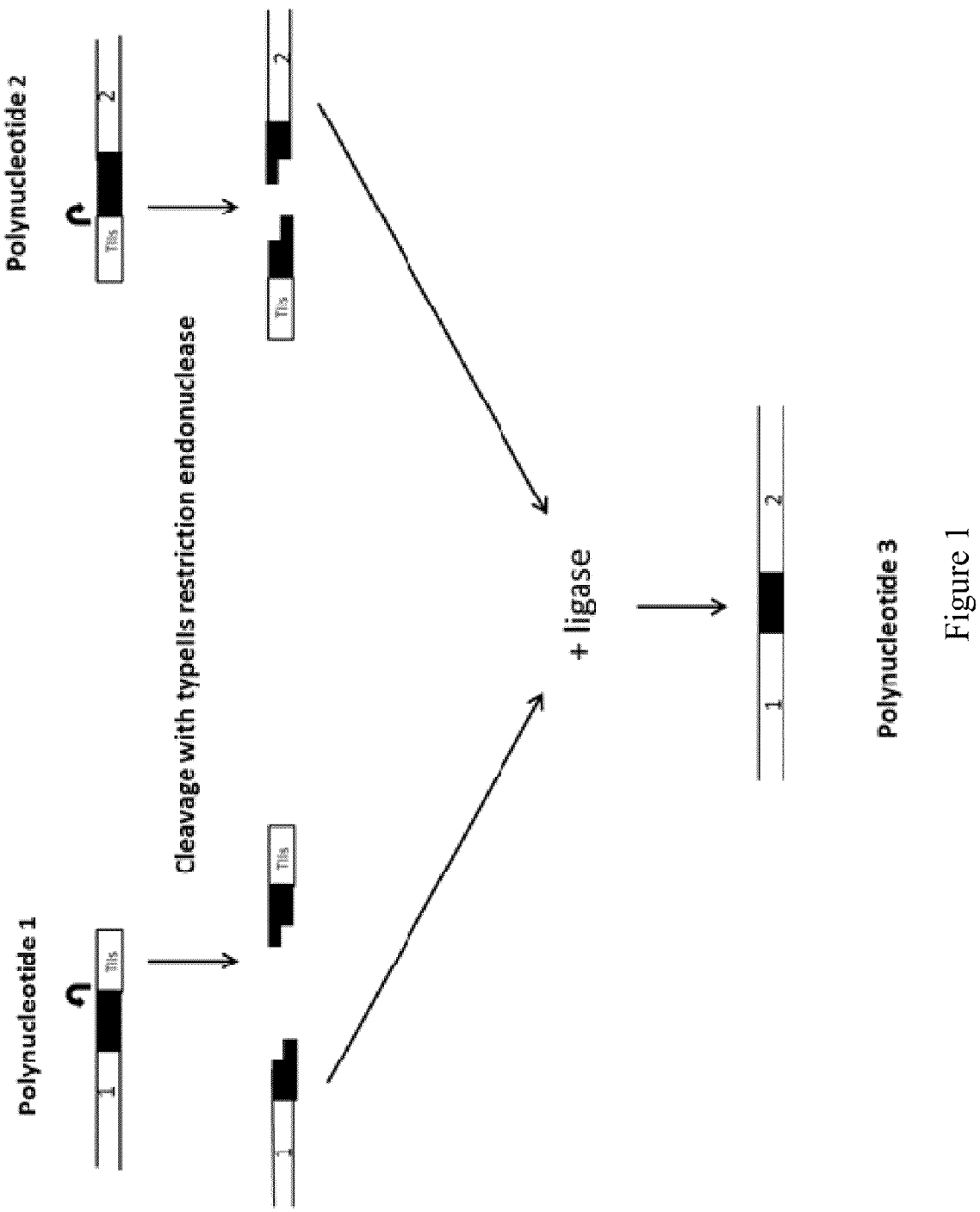

Methods, compositions and kits useful for a one-step molecular cloning system are provided. In certain embodiments the methods comprise combining into a mixture: a first polynucleotide comprising a selectable marker and two sequences recognized by typeIIs restriction enzymes; a second polynucleotide comprising two sequences recognized by typeIIs restriction enzymes; a typeIIs restriction enzyme and a DNA ligase so that the first polynucleotide is joined to the second polynucleotide. Methods for designing and synthesizing vectors useful for practicing of the method are also disclosed. Methods for creating combinatorial libraries using the method are also disclosed.

2. BACKGROUND

The cloning of DNA segments is performed as a daily routine in many research labs. It is frequently performed in order to move a first polynucleotide sequence from a first vector into a second vector, where the second vector performs a function that is not performed by the first. Differences between the two vectors may include differences in selectable markers or differences in replicative sequences. They may also include differences in vector sequence elements that may directly interact with the first polynucleotide, for example by affecting expression of the first polynucleotide, or by encoding polypeptides that interact with or are joined to polypeptides encoded by the first polynucleotide.

The specialized vectors used for subcloning DNA segments are functionally diverse. These include but are not limited to: vectors for expressing genes in various organisms; for regulating gene expression; for providing tags to modify polypeptide properties such as solubility, localization, affinity for a substrate, color, fluorescence, characteristics that facilitate protein purification and characteristics that facilitate tracking of proteins in cells; for modifying the cloned DNA segment (e.g., generating deletions); for the synthesis of probes (e.g., riboprobes); for the preparation of templates for DNA sequencing; for the identification of protein coding regions; for the fusion of various protein-coding regions; for expressing one or more enzymes to catalyze a reaction and for providing large amounts of the DNA of interest. It is common that a particular investigation will involve subcloning the DNA segment of interest into several different specialized vectors.

A great deal of time can be expended in the cloning of DNA segments. The basic methods of cloning have been known for many years and have changed little during that time. A typical cloning protocol based on restriction enzyme digestion is as follows: (1) digest the DNA to be cloned with one or two restriction enzymes; (2) purify the digested DNA segment of interest to be cloned; (3) prepare the vector by cutting with appropriate restriction enzymes, treating with alkaline phosphatase, purifying as appropriate; (4) ligate the DNA segment to the vector, with appropriate controls to estimate background of uncut and self-ligated vector; and (5) introduce the resulting vector into an *E. coli* host cell; (6) pick selected colonies and grow small cultures overnight; (7) purify plasmid DNA; and (8) analyze the isolated plasmid on agarose gels (often after diagnostic restriction enzyme digestions) or by PCR.

As known in the art, simple subclonings can be done in one day (e.g., the DNA segment is not large and the restriction sites are compatible with those of the subcloning vector). However, many other subclonings can take several weeks, especially those involving unknown sequences, long fragments, toxic genes, unsuitable placement of restriction sites, high backgrounds or impure enzymes. Subcloning DNA fragments is thus often viewed as a chore to be done as few times as possible.

Accordingly, subcloning methods, using traditional restriction enzymes and ligase, are time consuming and relatively unreliable. There is thus a need for a rapid and reliable method for moving a polynucleotide into a plurality of specialized vectors. There is also a need for a rapid and reliable method for moving a plurality of polynucleotides into a single specialized vector.

Furthermore, site specific recombinases have been used to recombine DNA in vitro and in vivo. However, significant disadvantages of such methods include the time required to perform the reaction, the cost of the reagents, and the unavoidable incorporation of specific recombinase recognition sequences into the final construct: these sequence "scars" can interfere with the functions of other sequence elements within the construct.

Accordingly, there is a need in the art for an alternative rapid cloning system that provides advantages over the known use of multiple cloning sites or engineered recombination sites.

3. SUMMARY

The present disclosure relates to nucleic acids, vectors and methods for combining one or more polynucleotides with one or more vectors.

The method takes advantage of DNA digestion by a restriction enzyme that recognizes a non-palindromic sequence, and that cleave outside its recognition sequence, for example a typeIIs restriction enzyme (referred to herein as a "typeIIs restriction enzyme"). Following cleavage of DNA by a typeIIs restriction enzyme, one of the ends produced by such cleavage lacks any part of the recognition sequence. It is thus possible to design two polynucleotide sequences, each comprising a recognition sequence for a respective typeIIs restriction enzyme, such that cleavage of each polynucleotide with its respective typeIIs restriction enzyme produces a first end from the first polynucleotide and a second end from the second polynucleotide, and wherein said first end and said second end are compatible ends, that is either both are blunt, or both possess overhangs of the same length and directionality and with complementary sequences, such that said DNA ends can be joined by a DNA ligase, producing a third polynucleotide (FIG. 1). In preferred embodiments the third polynucleotide lacks sequences recognized by one or both of the respective typeIIs restriction enzyme In some embodiments compatible ends are produced from one or more of the typeIIs enzymes that produce a 1 bp 5'-overhang selected from the group consisting of AlwI, BccI, PleI, AsuC2I, BceFI, BcnI, BisI, Bme13901, BmrFI, BseBI, BsiLI, Bst2UI, BstOI, CauII, Fsp4HI, GluI, ItaI, MspR91, MvaI, SatI, AspI, Psyl, TelI, and BstENI. In some embodiments compatible ends are produced from one or more of the typeIIs enzymes that produce a 2 bp 5'-overhang is selected from the group consisting of BceAI, FauI, EcoP15I, Hpy188III, SmuI, and Hpy178III. In some embodiments compatible ends are produced from one or more of the typeIIs enzymes that produce a 3 bp 5'-overhang selected from the group consisting of BspQI, Bst6I, EarI, Eam1104I, Ksp632I, LguI, PciSI, and SapI. In some embodiments compatible ends are produced from one or more of the typeIIs enzymes that produce a 4 bp 5'-overhang selected from the group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. In some embodiments compatible ends are produced from one or more of the typeIIs enzymes that produce a 5 bp 5'-overhang is CseI or HgaI. In some embodiments compatible ends are produced from one or more of the typeIIs enzymes that produce a 6 bp 5'-overhang is CjeI or CjePI. In some embodiments compatible ends are produced from one or more of the typeIIs enzymes that produce a 7 bp 5'-overhang including TscAI.

In some embodiments compatible ends are produced from one or more of the typeIIs enzymes that produce a 1 bp 3'-overhang selected from the group consisting of MnlI, HphI, HpyAV, MboII, BciVI, BmrI, BlsI, Hin4II, BmeRI, AspEI, and NruGI. In some embodiments compatible ends are produced from one or more of the typeIIs enzymes that produce a 2 bp 3'-overhang selected from the group consisting of BspCNI, BtsCI, BtsIMutI, AcuI, BpmI, BpuEI, BseRI, BsgI, BsrDI, BtsI, EciI, MmeI, NmeAIII, BcgI, CspCI, DrdI, BseGI, BseMII, BstF5I, TspDT1, TspGWI, ApyPI, Bce831, BsbI, Bse3DI, BseMI, CchII, CchIII, CdpI, CjeNIII, CstMI, DrdIV, Eco57I, Eco57MI, GsuI, NlaCI, PlaDI, PspPRI, RdeGBII, RdeGBIII, SdeAI, TaqII, TsoI, Tth111II, WviI, AquII, AquIV, DraRI, MaqI, PspOMII, RceI, RpaB5I, RpaBI, RpaI, SstE37I, NgoAVIII, AasI, Ali, BdaI, and DseDI. In some embodiments compatible ends are produced from one or more of the typeIIs enzymes that produce a 3 bp 3'-overhang selected from the group consisting of AlwNI, DraIII, DraIII-HF, BglI, BsaXI, BsII, BstAPI, MwoI, Pf1MI, SfiI, RleAI, AdeI, CaiI, PstNI, AccB71I, AfiI, BasI, Bsc4I, BseLI, BsiYI, BstMWI, HpyF10VI, Pf1BI, and Van91I. In some embodiments compatible ends are produced from one or more of the typeIIs enzymes that produce a 4 bp 3'-overhang including BstXI. In some embodiments compatible ends are produced from one or more of the typeIIs enzymes that produce a 5 bp 3'-overhang selected from the group consisting of BaeI, ApaBI, BpII, FaII, HaeIV, Hin4I, Bsp24I, PpiI, TstI, AloI, ArsI, BarI, PsrI, and AjuI.

In some embodiments the DNA ends are joined by a DNA ligase. DNA ligases join two DNA fragments by catalyzing the formation of an internucleotide ester bond between phosphate and deoxyribose and are active during DNA replication, DNA repair and DNA recombination. There are two forms of DNA ligase, one requires ATP and the other NAD, the latter being restricted to eubacteria. Eukaryotic, archebacterial, viral and some eubacterial DNA-ligases are ATP dependent. In a preferred embodiment, an ATP dependent T4 DNA ligase is used. Other examples of ligases include but are not limited to T3 DNA ligase, T7 DNA ligase, ElectroLigase™, Taq DNA ligase, 9° N™ DNA ligase, T4 RNA ligase, *E. coli* DNA ligase, DNA ligase I, DNA ligase III or DNA ligase IV.

Two polynucleotides comprising typeIIs restriction sites as described above can be joined to make a third polynucleotide by mixing into a single reaction: the two polynucleotides, a typeIIs restriction enzyme that recognizes said first recognition sequence and said second recognition sequence and a DNA ligase. Because the third polynucleotide lacks said recognition sequences, it cannot be cleaved by the typeIIs restriction enzymes, so that the reaction proceeds in one direction only.

Because the sequence of the cleaved end of the DNA is not contained within the recognition sequence, any compatible overhangs may be selected. Thus it is possible to completely control the sequence of the third polynucleotide, without being forced to incorporate restriction sites or recombination sequences. In some embodiments the overhang comprises a sequence that can perform a specific function, in some embodiments the overhang comprises the sequence of a codon, or a sequence complementary to a codon, in some embodiments the codon encodes a methionine or a glycine or an alanine or a stop codon, in some embodiments the overhang comprises 5'-ATG-3' or 5'-CAT-3' or 5'-GGN-3' or 5'-NCC-3' or 5'-GCN-3' or 5'-NGC-3' or 5'-TAA-3' or 5'-TTA-3'.

Figure 2:
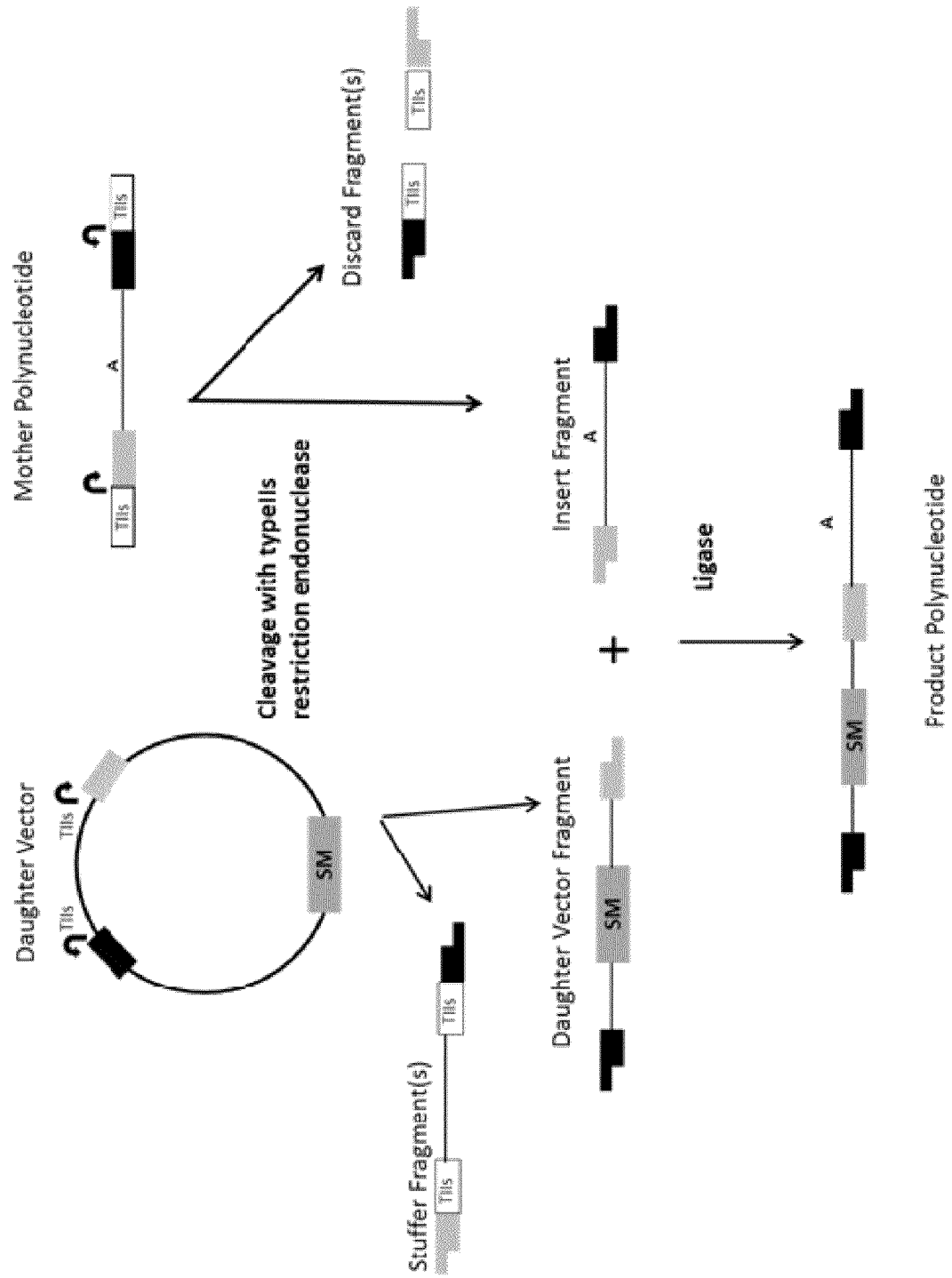

In some embodiments a first polynucleotide vector, referred to herein as a "Daughter Vector" comprises a first typeIIs restriction site and a second typeIIs restriction site, wherein cleavage of said Daughter Vector with said first and second typeIIs restriction enzymes produces a first polynucleotide vector fragment, referred to herein as a "Daughter Vector Fragment", which comprises a selectable marker but lacks said first and second typeIIs restriction sites, and a second polynucleotide fragment, referred to herein as a "Stuffer Fragment". A second polynucleotide, referred to herein as a "Mother Polynucleotide" comprises a third typeIIs restriction site and a fourth typeIIs restriction site, wherein cleavage of said second polynucleotide with said third and fourth typeIIs restriction enzymes produces a third polynucleotide fragment lacking said third and fourth typeIIs restriction sites, referred to herein as an "Insert Fragment", and a fourth polynucleotide, referred to herein as a "Discard Fragment". In some embodiments one or two ends of said Daughter Vector Fragment are compatible with one or two ends of said Insert Fragment, such that said fragments can be joined by a DNA ligase to produce a polynucleotide comprising a selectable marker, referred to herein as a "Product Polynucleotide" (FIG. 2).

In some embodiments said Product Polynucleotide is circular. In some embodiments said Product Polynucleotide lacks one or more of said first second, third and fourth typeIIs restriction sites. In some embodiments said restriction sites comprise two or more different sequences, in some embodiments said restriction sites are the same sequence. In preferred embodiments there is only one possible way of assembling the compatible ends of said Daughter Vector Fragment and said Insert Fragment, such that the relative positions and orientations of the Daughter Vector Fragment sequence and the Insert Fragment sequence in the Product Polynucleotide are predetermined.

Some embodiments comprise a mixture of a Daughter Vector, a Mother Polynucleotide, typeIIs restriction enzymes and DNA ligase such that a Daughter Vector Fragment, and an Insert Fragment are produced from said Daughter Vector and said Mother Polynucleotide by said typeIIs restriction enzymes, and the Daughter Vector Fragment and the Insert Fragment are joined by the DNA ligase to form a Product Polynucleotide. In preferred embodiments said Product Polynucleotide lacks typeIIs restriction sites recognized by the typeIIs restriction enzymes in the mixture. In some embodiments said mixture is transformed into a host cell.

Some embodiments comprise a mixture of a pre-digested Daughter Vector Fragment, a Mother Polynucleotide, typeIIs restriction enzymes and DNA ligase such that an Insert Fragment is produced from said Mother Polynucleotide by the typeIIs restriction enzymes, and the Daughter Vector Fragment and the Insert Fragment are joined by the DNA ligase to form a Product Polynucleotide. In preferred embodiments said Product Polynucleotide lacks typeIIs restriction sites recognized by the typeIIs restriction enzymes in the mixture. In some embodiments said mixture is transformed into a host cell.

In some embodiments said first Daughter Vector Fragment further comprises an origin of replication for a bacterial host, in some embodiments said bacterial host is *E. coli*. In some embodiments said Daughter Vector Fragment further comprises sequences conferring the ability to be replicated in a eukaryotic host, in some embodiments said eukaryotic host is a mammalian cell or a plant cell or an insect cell or a yeast cell. In some embodiments said Daughter Vector Fragment further comprises sequences conferring the ability to be replicated in a non-photosynthetic microorganism having the ability to use a C1 Substrate as a source of energy, whether or not such C1 Substrate is the sole source of energy for such microorganism. As used herein, a "C1 Substrate" is an organic compound containing at least one carbon atom that lacks carbon-to-carbon bonds, including without limitation syngas, natural gas, unconventional natural gas, methane, methanol, formaldehyde, formic acid (formate), carbon monoxide, carbon dioxide, methylated amines (e.g., methylamine, dimethylamine or trimethylamine), methylated thiols, methyl halogens (e.g., bromomethane, chloromethane, iodomethane or dichloromethane) and cyanide. In some embodiments said non-photosynthetic microorganism is selected from one of the following organisms: *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Paracoccus, Nocardia, Arthrobacter, Rhodopseudomonas, Hansenula, Torulopsis, Rhodotorula, Moorella, Pyrococcus, Eubacterium, Desulfobacterium, Carboxydothermus, Acetogenium, Acetobacterium, Acetoanaerobium, Butyribaceteriumm, Peptostreptococcus, Yarrowia, Yarrowia lipolytica, Candida lipolytica, Clostridium autoethanogenum, Clostridium llungdahli, Clostridium ragsdalei, Clostridium carboxydivorans, Butyribacterium methylotrophicum, Clostridium woodii* and *Clostridium neopropanologen.*

In some embodiments said Daughter Vector further comprises a double-stranded DNA break or a dephosphorylated double-stranded DNA break, or a counter-selectable marker within said Stuffer Fragment, in some embodiments said counter-selectable marker is sacB, rpsL, tetAR, pheS, thyA, lacY, gata-1, ccdB, kid or barnase. In some embodiments said Mother Polynucleotide further comprises a double-stranded DNA break, or a dephosphorylated double-stranded DNA break or a counter-selectable marker within said Discard Fragment sequence, in some embodiments said counter-selectable marker is sacB, rpsL, tetAR, pheS, thyA, lacY, gata-1, ccdB, kid or barnase. In some embodiments said mixture is transformed into a host cell that is grown under conditions that are restrictive for growth of cells containing a counter-selectable marker, thereby preventing the growth of cells containing DNA comprising said Stuffer Fragment or said Discard Fragment.

In some embodiments a Daughter Vector Fragment further comprises a sequence controlling transcription in a bacterial host, a sequence controlling transcription in a eukaryotic host, a sequence controlling initiation of translation, a sequence controlling termination of transcription, or a sequence encoding a first polypeptide that can confer properties such as solubility, stability, improved yields, proper folding, localization, affinity for a substrate, color, fluorescence, characteristics that facilitate protein purification and characteristics that facilitate tracking of proteins in cells when fused to a second polypeptide. In some embodiments an Insert Fragment comprises a sequence encoding a polypeptide. In some embodiments a Product Polynucleotide comprises a Daughter Vector Fragment sequence juxtaposed with an Insert Fragment sequence such that an element controlling or modifying expression that is partly derived from said Daughter Vector Fragment controls the expression of a polypeptide, which is in part encoded by said Insert Fragment. In some embodiments a Product Polynucleotide comprises a Daughter Vector Fragment sequence juxtaposed with an Insert Fragment sequence such that a polypeptide that is partly encoded by said Daughter Vector Fragment is fused to a polypeptide that is in part encoded by said Insert Fragment.

Figure 3A:
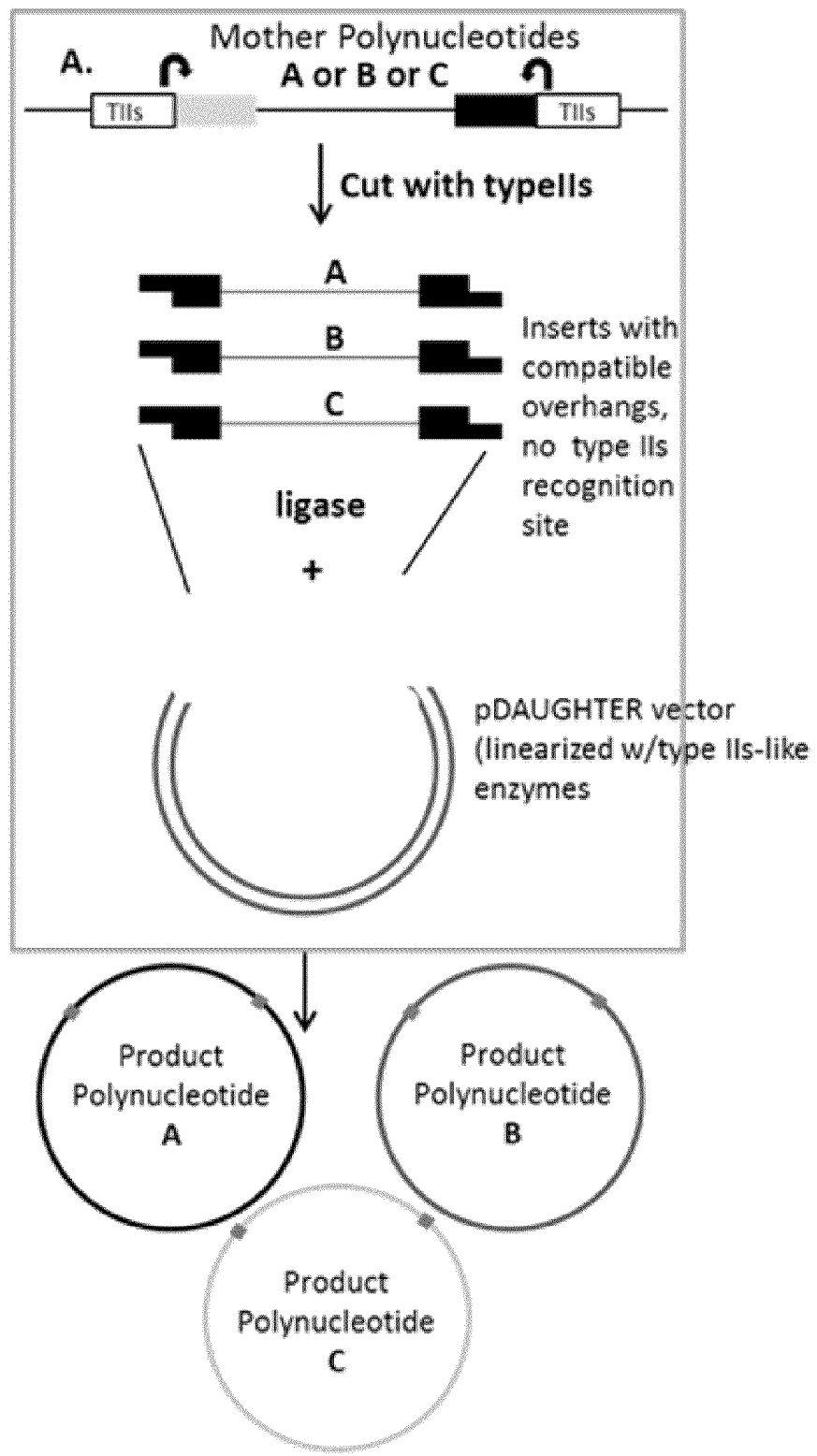

Some embodiments comprise a Daughter Vector and a plurality of Mother Polynucleotides, wherein cleavage of the Daughter Vector and the plurality of Mother Polynucleotides with their respective typeIIs restriction enzymes produces a Daughter Vector Fragment and a plurality of Insert Fragments, and wherein a mixture of the Daughter Vector Fragment and a plurality of Insert Fragments can be ligated together to produce a plurality of Product Polynucleotides, each comprising a single Insert Fragment ligated with a single Daughter Vector Fragment (FIG. 3A).

Figure 3B:
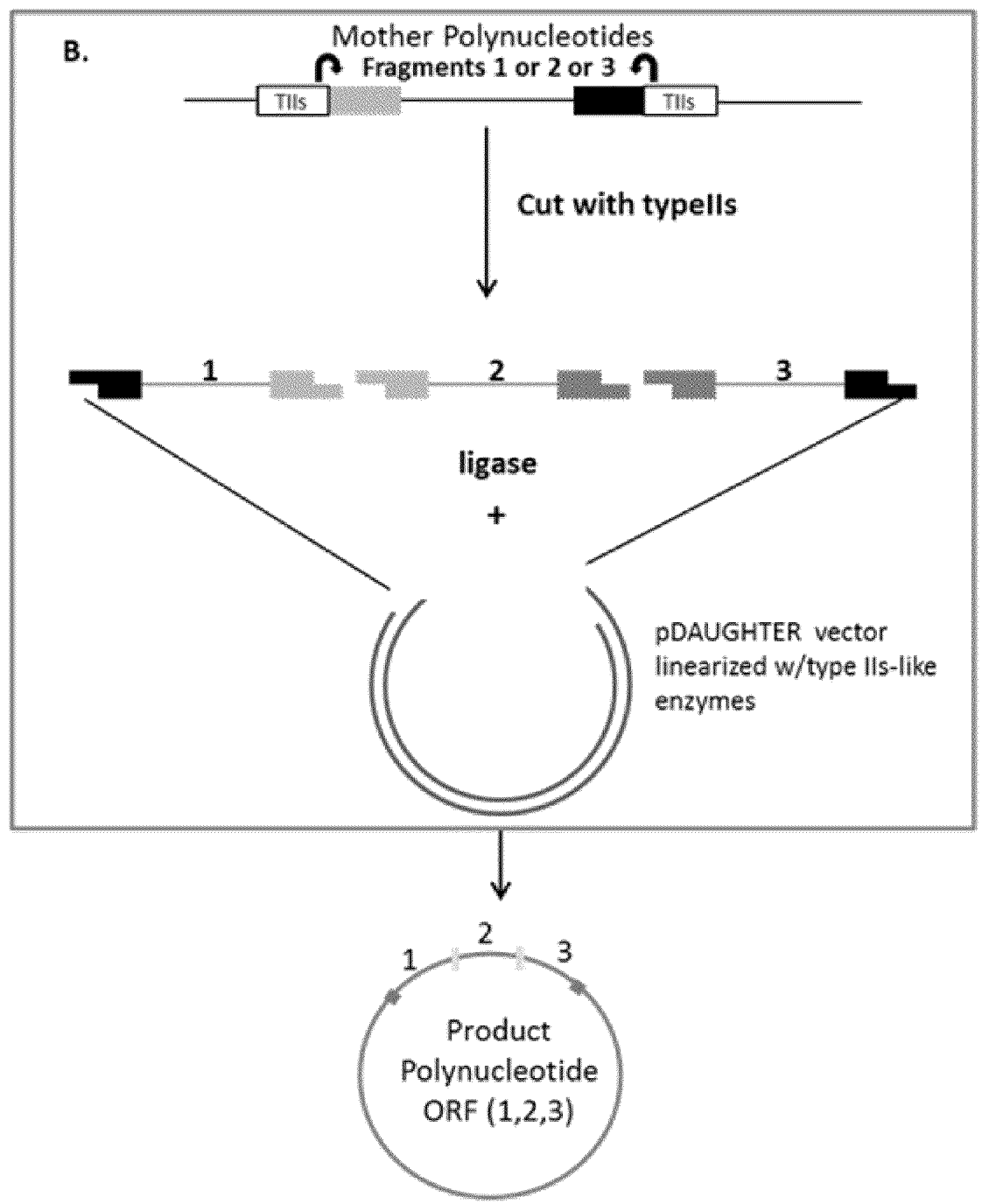

Some embodiments comprise a Daughter Vector and a plurality of Mother Polynucleotides, wherein cleavage of the Daughter Vector and the plurality of Mother Polynucleotides with their respective typeIIs restriction enzymes produces a Daughter Vector Fragment and a plurality of Insert Fragments, and wherein a mixture of the Daughter Vector Fragment and a plurality of Insert Fragments can be ligated together to produce one or more Product Polynucleotides, each comprising a plurality of Insert Fragments ligated with a single Daughter Vector Fragment, and wherein the order of the Insert Fragment sequences within the Product Polynucleotide is predetermined by their respective overhangs (FIG. 3B).

Figure 3C:
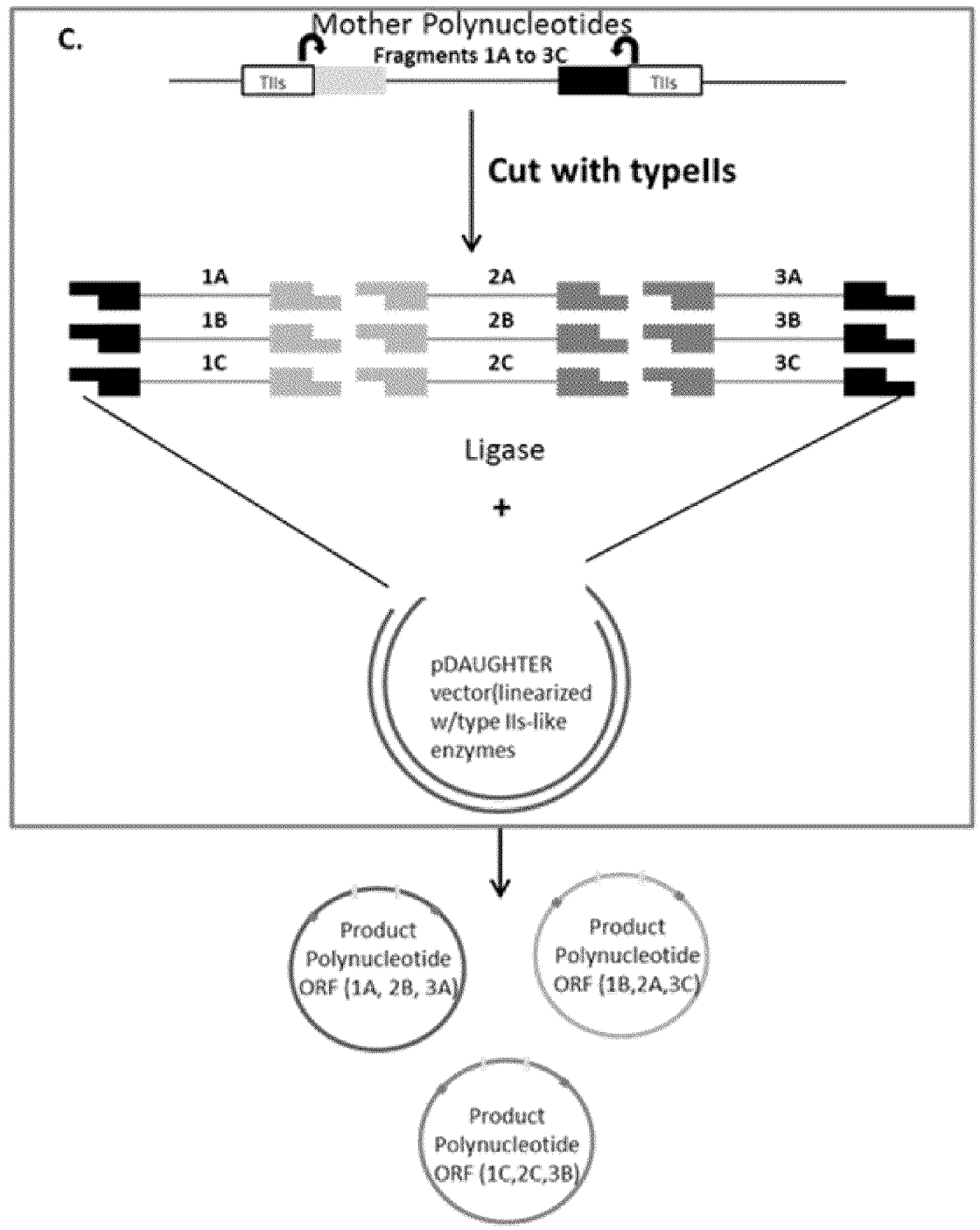

Some embodiments comprise a mixture of a Daughter Vector or a pre-digested Daughter Vector Fragment, a plurality of Mother Polynucleotides, typeIIs restriction enzymes and DNA ligase such that a Daughter Vector Fragment, and an Insert Fragment are produced from said Daughter Vector and said Mother Polynucleotide by said typeIIs restriction enzymes, and the Daughter Vector Fragment and the Insert Fragment are joined by the DNA ligase to form a Product Polynucleotide. In preferred embodiments said Product Polynucleotide lacks typeIIs restriction sites recognized by the typeIIs restriction enzymes in the mixture. In some embodiments said mixture is transformed into a host cell (FIGS. 3A-3C).

Another embodiment of the present disclosure relates to a kit comprising a carrier or receptacle being compartmentalized to receive and hold therein at least one container, wherein a first container contains a DNA molecule comprising a Daughter Vector comprising a first typeIIs restriction site and a second typeIIs restriction site, wherein cleavage of said first polynucleotide with said first and second typeIIs restriction enzymes produces a first polynucleotide fragment comprising a selectable marker but lacking said first and second typeIIs restriction sites, as described herein. In certain embodiments the kit comprises a linear DNA molecule comprising a selectable marker but lacking said first and second typeIIs restriction sites, wherein said linear DNA molecule was produced by digesting said first polynucleotide vector with said first typeIIs restriction enzyme and said second typeIIs restriction enzyme. In certain embodiments the kit further comprises a restriction enzyme capable of cleaving DNA to produce DNA ends that are compatible with the ends of the DNA molecule in the kit; in certain embodiments the kit further comprises a DNA ligase; in certain embodiments the restriction enzyme and the DNA ligase are mixed; in certain embodiments the kit further comprises a reaction buffer.

Other embodiments will be evident to those of ordinary skill in the art from the teachings contained herein in combination with what is known to the art.

4. BRIEF DESCRIPTION OF THE DRAWINGS

FIG. 1 is a schematic showing assembly of two polynucleotides with respective typeIIs recognition sequences. Cleavage of each polynucleotide with its respective typeIIs restriction enzyme, produces a first end from the first polynucleotide and a second end from the second polynucleotide, and wherein said first end and said second end are compatible ends, that is both are blunt ends, or both possess overhangs of the same directionality and with complementary sequences, such that said DNA ends can be joined by a DNA ligase, producing a third polynucleotide. In preferred embodiments the third polynucleotide lacks sequences recognized by either respective typeIIs restriction enzyme.

FIG. 2 depicts cleavage of Mother Polynucleotide and Daughter Vector by type IIs restriction enzyme(s) and their subsequent ligation by a DNA ligase to form a Product Polynucleotide. Cleavage of the Daughter Vector with the typeIIs restriction enzyme(s) generates a Daughter Vector Fragment and one or more Stuffer Fragments. Cleavage of the Mother Polynucleotide by typeIIs restriction enzyme(s) generates an Insert Fragment and one or more Discard Fragments. At least one overhang in the Daughter Vector Fragment is compatible with an overhang of the Insert Fragment, such that DNA ligase can join them to form a Product Polynucleotide. In preferred embodiments a first overhang in the Daughter Vector Fragment is compatible with a first overhang of the Insert Fragment and a second overhang in the Daughter Vector Fragment is compatible with a second overhang of the Insert Fragment so that the Product Polynucleotide is a closed circle.

FIGS. 3A-3C show schematics of ways of combining multiple inserts and vector fragments. FIG. 3A shows a mixture comprising Mother Polynucleotides A, B, or C. The inserts are digested with typeIIs enzymes to generate compatible ends to the Daughter Vector. The Daughter Vector can be linearized separately or in the same reaction with the Mother Polynucleotides. The reaction produces a plurality of Product Polynucleotides, each consisting of a single Insert ligated into a single Daughter Vector Fragment. FIG. 3B shows a plurality of Mother Polynucleotides which are joined in a pre-defined order into a single Daughter Vector Fragment. The Daughter Vector and the plurality of Mother Polynucleotides can be mixed in the presence of typeIIs enzyme(s) and DNA ligase to produce a Product Polynucleotide that has inserts 1, 2 and 3 seamlessly joined together to form one contiguous functional polynucleotides, wherein the order of the Insert Fragment sequences is predetermined by their respective overhangs. FIG. 3C shows assembly of a plurality of Mother Polynucleotides, each of which produces an Insert Fragment with defined overhangs following digestion with typeIIs restriction enzymes. A plurality of possible Insert Fragments may be ligated in at least one of the positions in the resulting Product Polynucleotide. In this Figure the number of the Insert Fragment denotes the position of that Insert Fragment within the Product Polynucleotide, and the letter indicates an alternative sequence that may be ligated at this position. In the example shown, there are 3 possible Insert Fragments that may be ligated at the first position (1A, 1B, 1C), 3 possible Insert Fragments that may be ligated at the second position (2A, 2B, 2C) and 3 possible Insert Fragments that may be ligated at the third position (3A, 3B, 3C). The reaction mixture in this example will therefore contain 9 possible Product Polynucleotides.

Figure 4:
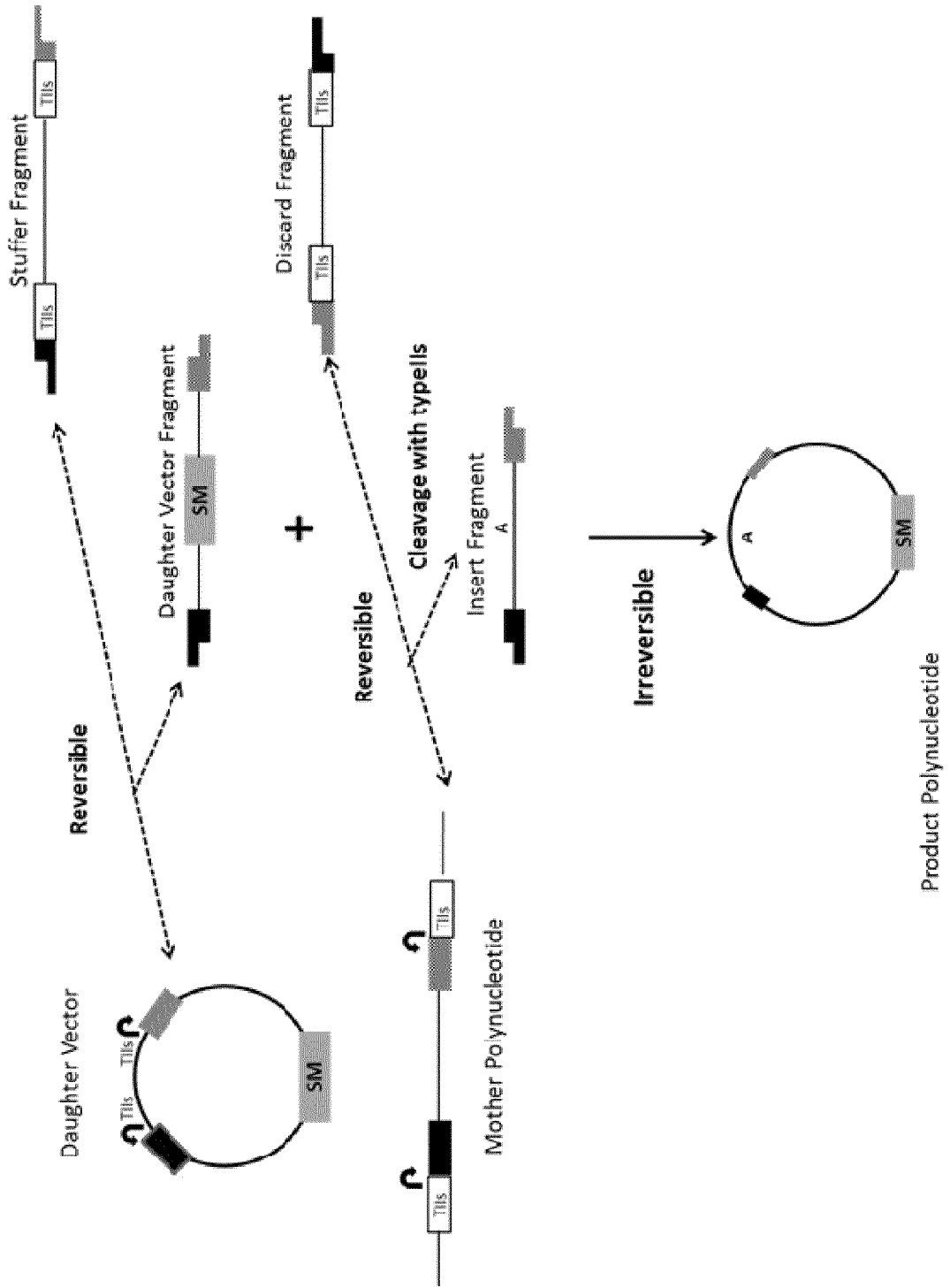

FIG. 4 shows that the presence of the typeIIs restriction enzyme and ligase in the same mix is advantageous and helps drive the reaction toward the formation of Product Polynucleotide. The Daughter Vector is digested by typeIIs enzymes to produce a Daughter Vector Fragment and one or more Stuffer Fragments. DNA ligase reverses this reaction, re-creating the Daughter Vector, which can again be digested by the typeIIs restriction enzymes. Similarly, the Mother Polynucleotide is digested by typeIIs enzymes to produce an Insert Fragment and one or more Discard Fragments. DNA ligase reverses this reaction, re-creating the Mother Polynucleotide, which can again be digested by the typeIIs restriction enzymes. The reversible reactions are indicated by dotted arrows. In contrast, the Product Polynucleotide, once formed from ligation of compatible Insert Fragment and Daughter Vector Fragment(s), lacks the typeIIs recognition sequences and therefore cannot be cut, making the reaction irreversible.

Figure 5:
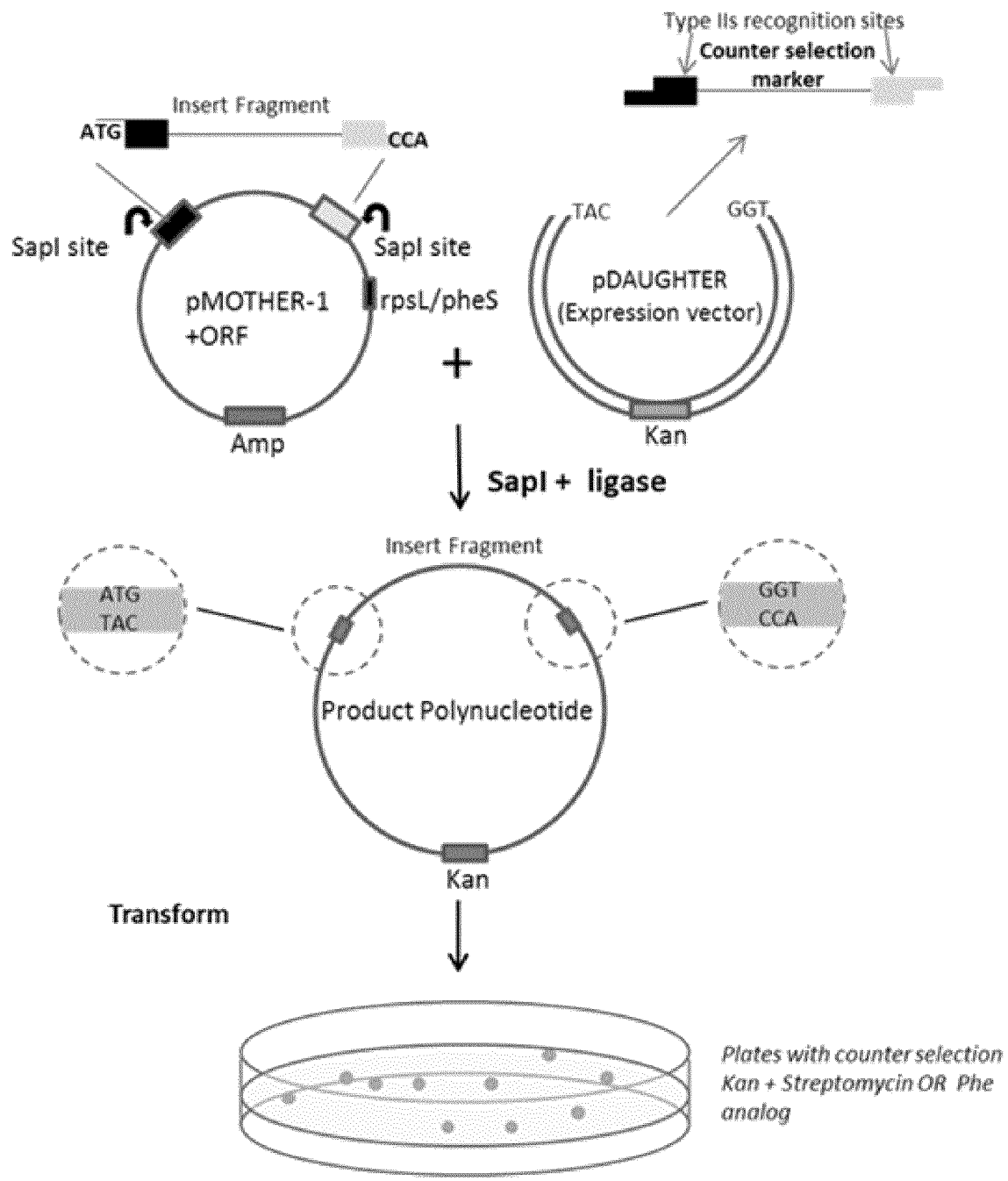

FIG. 5 is a schematic showing one embodiment of the approach described herein. The Mother polynucleotide with an open reading frame of interest (A) has flanking typeIIs sites that generate an ATG overhang at the 5' end and a CCA overhang at the 3' end in the Insert fragment; has counterselectable markers rpsL or pheS that allow selection against the mother polynucleotide and; a selectable resistance marker that is either the same as the daughter vector or is preferably different, in this illustration, the marker confers ampicillin resistance. The Daughter vector has a ccdB stuffer fragment that has flanking typeIIs sites such that compatible overhangs to the Insert Fragment are generated upon cleavage with typeIIs, presence of ccdB stuffer fragment selects against the daughter vector; has a selectable resistance marker that is the same or preferably different from the Mother polynucleotide, in this illustration, the marker confers Kanamycin resistance. The Daughter vector can be linearized or circular, shown in this illustration is a linearized Daughter vector which is a preferred embodiment. The vectors are mixed in a one-pot reaction along with typeIIs restriction enzyme SapI and ligase to produce the product polynucleotide that lacks the typeIIs sites. The product polynucleotide can be transformed and plated onto Agar plates with either the selection antibiotic kanamycin and counter selection antibiotic streptomycin or a phenylalanine analog p-chlorophenylalanine alone or in combination.

Figure 6A:
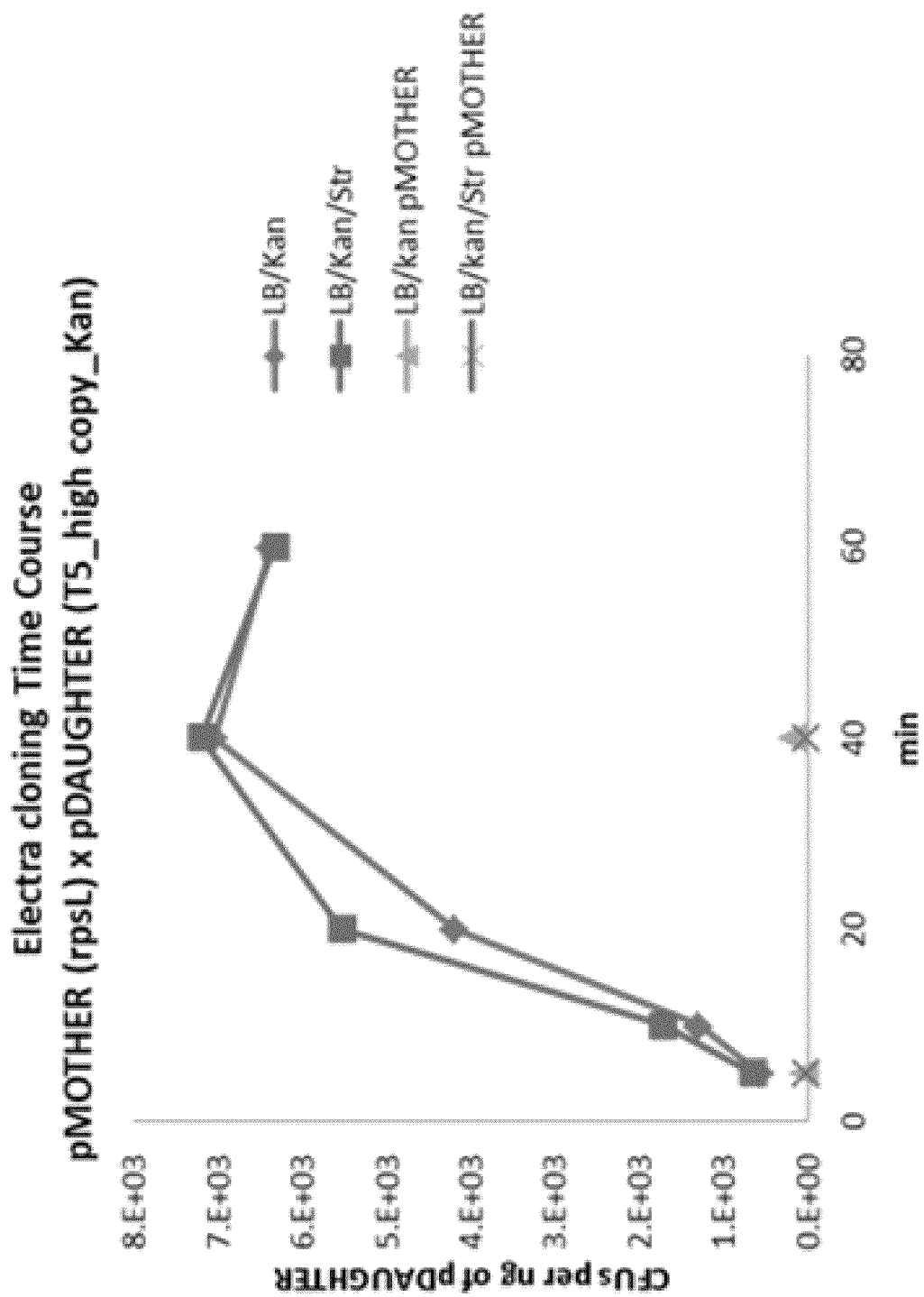
Figure 6B:
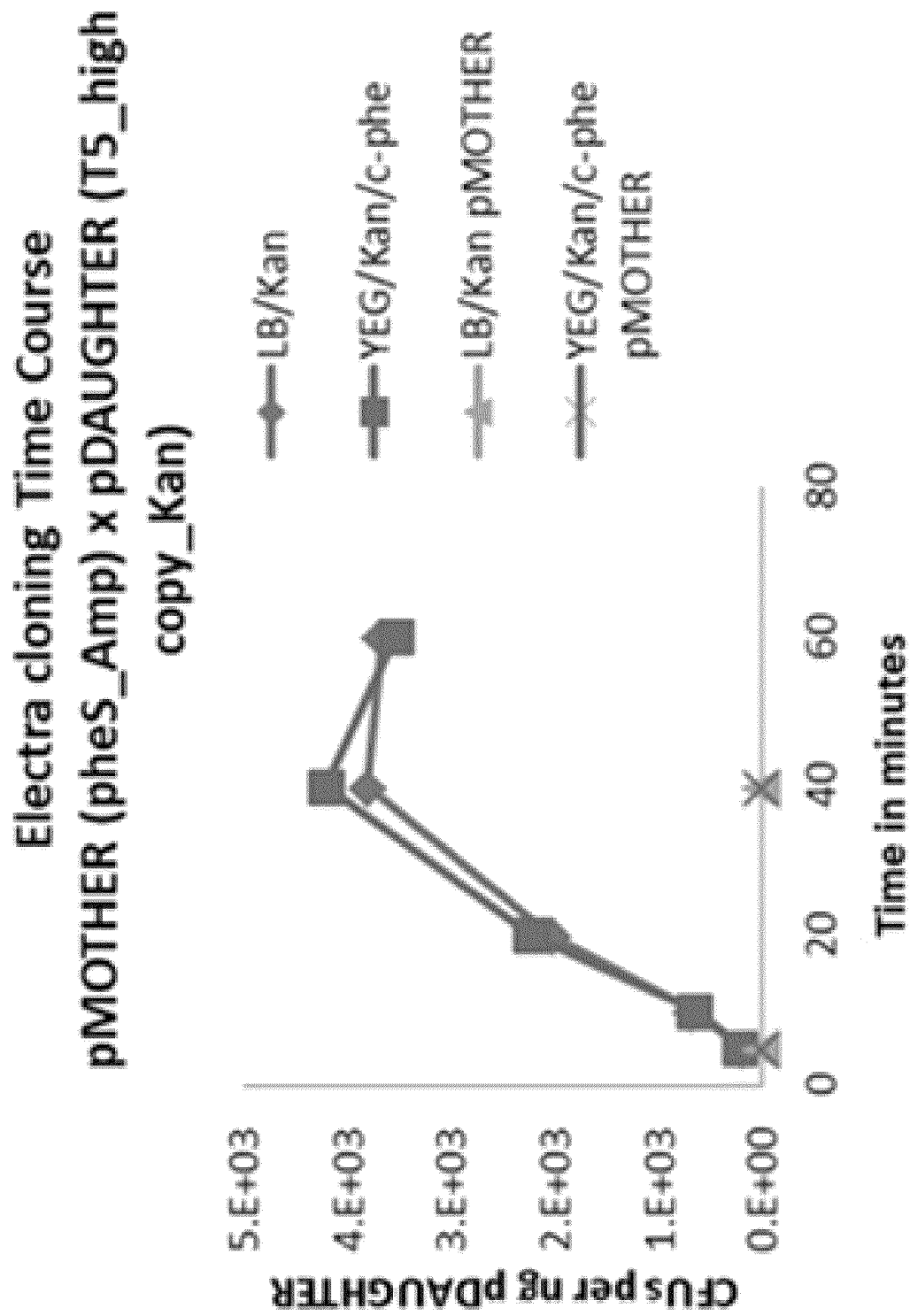

FIGS. 6A-6B illustrate a time course for the reaction containing SapI and ligase mix and combinations of two different Mother polynucleotides encoding yellow fluorescent protein and a daughter vector. FIG. 6A depicts a mother polynucleotide with rpsL counter selection marker and ampicillin resistance and an *E. coli* expression Daughter vector with a T5 promoter and strong RBS with kanamycin resistance marker. FIG. 6B depicts a mother polynucleotide with pheS counter selection marker and ampicillin resistance and an *E. coli* expression Daughter vector with a T5 promoter and strong RBS with kanamycin resistance marker. The reactions were incubated for time points ranging from 5 minutes to 60 minutes and transformants counted on plates with kanamycin alone or with both kanamycin and the counter selection marker, either streptomycin or the phenylalanine analog. Colony forming units (CFUs) were calculated per ng of Daughter vector DNA and plotted against the various time points. The reactions reach completion by 40 minutes, with transformants obtained in as little as 5 minutes.

Figure 7:
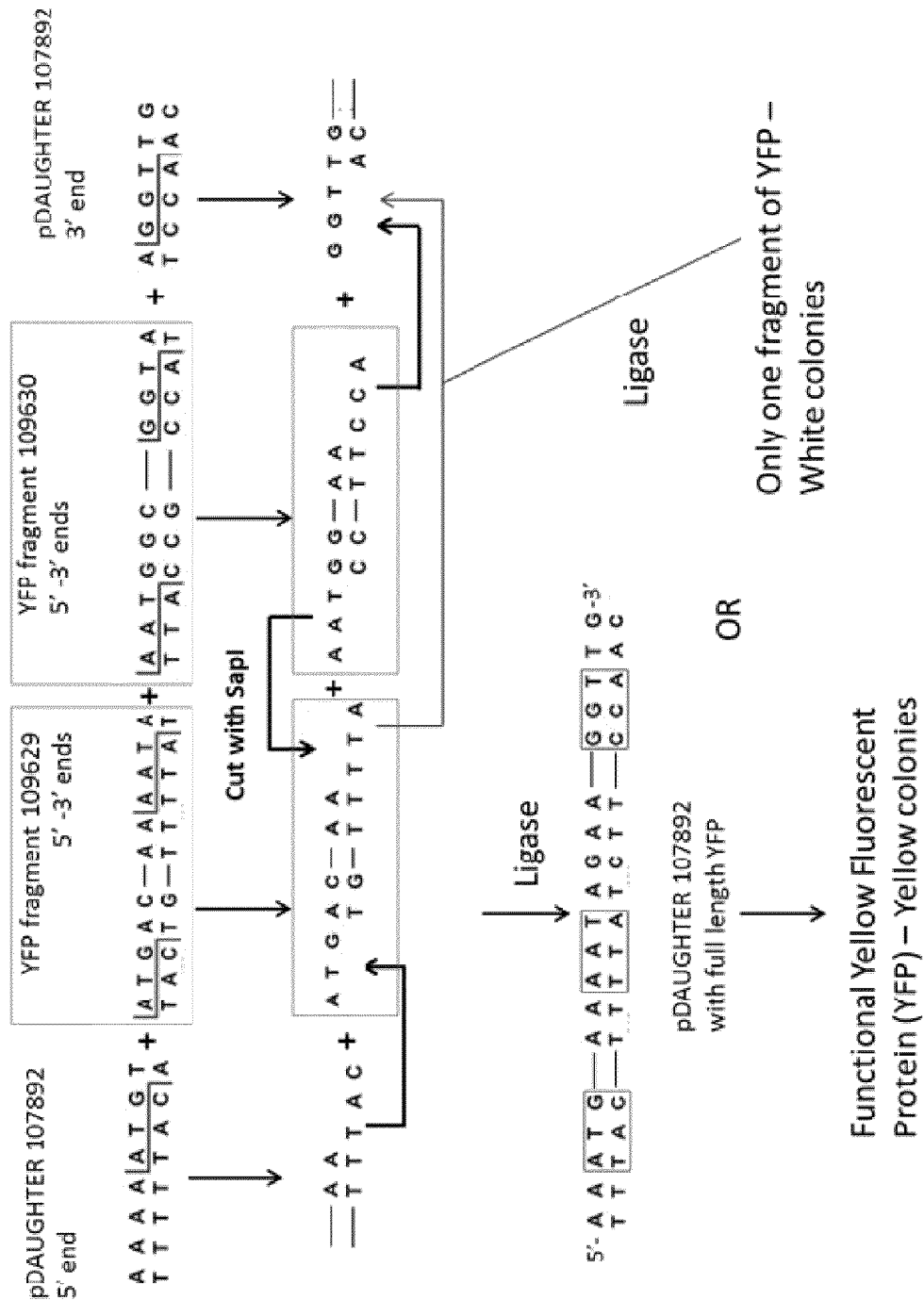

FIG. 7 is a schematic showing assembly of two fragments encoding yellow fluorescent proteins with three base compatible overhangs that were generated by type IIs restriction enzyme SapI. Assembly was done in a one pot reaction as described herein. The compatible ends of inserts from 109629 and 109630 can assemble to form a fully functional yellow fluorescent protein seen as yellow colonies. A large percentage of white colonies observed suggest that the TTA overhang of fragment insert from 109629, generated upon digestion with SapI, is psuedo-compatible to the GGT overhang generated by SapI digestion of daughter vector 107892, forming a non-standard Watson-Crick base pairing, T with G in a way that can be joined by DNA ligase with reasonable efficiency.

Figure 8:
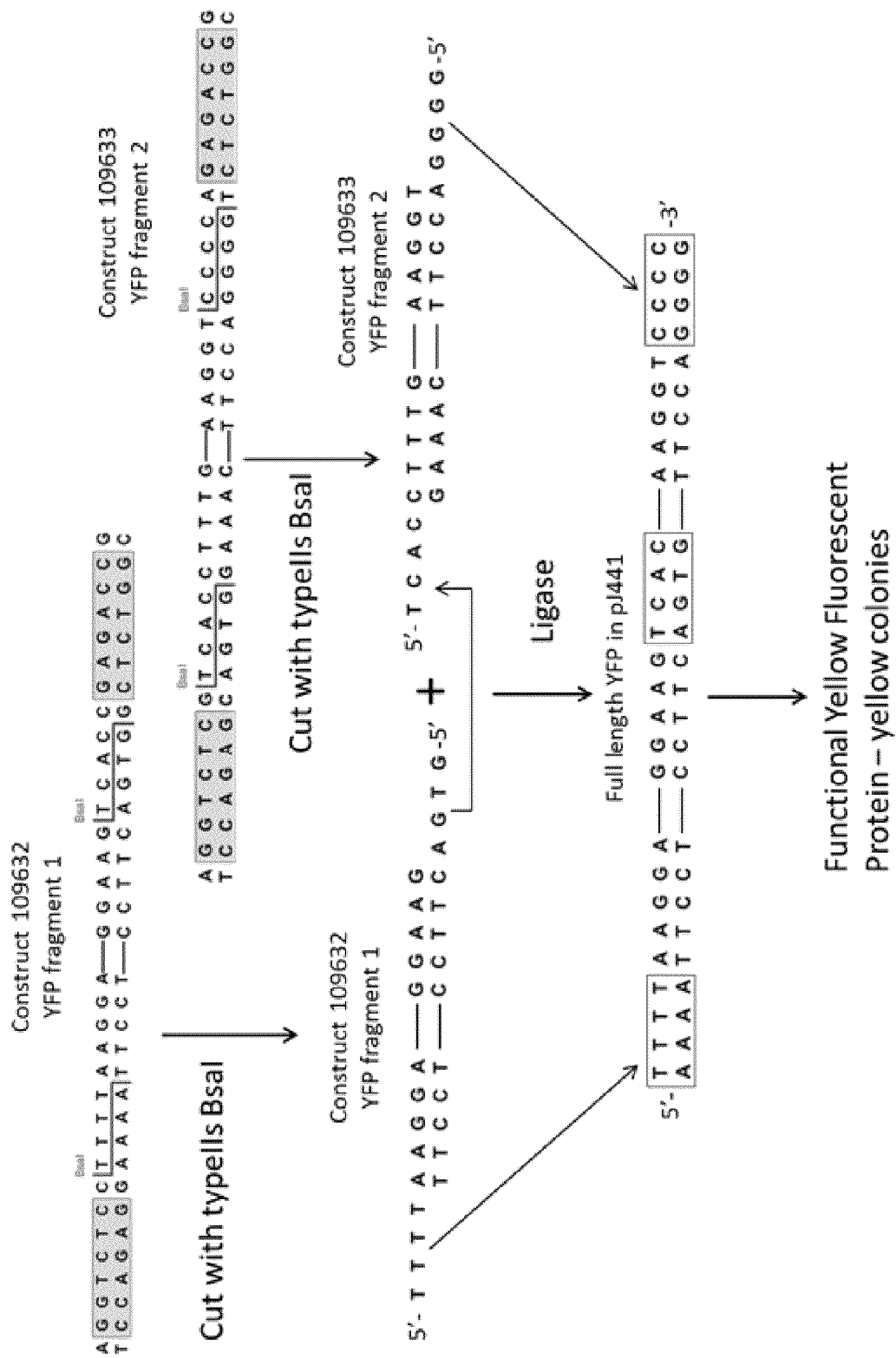

FIG. 8 is a schematic showing assembly of two fragments encoding yellow fluorescent proteins with four base compatible overhangs that were generated by type IIs restriction enzyme BsaI. Assembly was done in a one pot reaction as described herein. The compatible ends of inserts from 109632 and 109633 can assemble to form a fully functional yellow fluorescent protein seen as yellow colonies.

5. DETAILED DESCRIPTION

5.1 Brief Description

The first aspect of this disclosure is a method of joining two or more polynucleotides to form a product polynucleotide. In one embodiment, the method comprises incubating a mixture for a predetermined length of time, wherein the mixture comprises a) a first polynucleotide comprising a selectable marker, b) a second polynucleotide, other than the first polynucleotide, comprising a first typeIIs recognition sequence and a second typeIIs recognition sequence, c) a first typeIIs restriction endonuclease that recognizes the first typeIIs recognition sequence and cleaves the second polynucleotide to produce a first end, and a second typeIIs restriction endonuclease that recognizes the second typeIIs recognition sequence and cleaves the second polynucleotide to produce a second end, and wherein the first end is not complementary to or is not compatible with the second end, and d) a DNA ligase.

In one embodiment, the second polynucleotide of the first aspect of this disclosure further comprises a counter-selectable marker. In specific embodiments the counter-selectable marker is selected from the group consisting of sacB, rpsL, tetAR, pheS, thyA, lacY, gata-1, ccdB, kid and barnase. In one embodiment the selectable marker is an antibiotic resistant gene. In specific embodiments, the antibiotic resistant gene is a gene selected from the group consisting of an ampicillin resistant gene, a kanamycin resistant gene, a chloramphenicol resistant gene, and a zeocin resistant gene.

In one embodiment, the mixture of the first aspect of this disclosure is incubated at 25° C. In another embodiment the mixture is incubated at room temperature.

In one embodiment, the predetermined length of time of the first aspect of this disclosure is between 4 minutes and 10 minutes. In another embodiment the predetermined length of time is between 10 minutes and 30 minutes. In another embodiment the predetermined length of time is between 30 minutes and 50 minutes.

In one embodiment, the first typeIIs restriction endonuclease of the first aspect of this disclosure is selected from a group consisting of BspQI, Bst6I, EarI, Eam1104I, Ksp632I, LguI, PciSI, and SapI. In one embodiment, the second typeIIs restriction endonuclease of the first aspect of this disclosure is selected from a group consisting of BspQI, Bst6I, EarI, Eam1104I, Ksp632I, LguI, PciSI, and SapI.

In one embodiment, the first typeIIs restriction endonuclease of the first aspect of this disclosure is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. In one embodiment, the second typeIIs restriction endonuclease of the first aspect of this disclosure is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I.

In one embodiment, the first typeIIs restriction endonuclease of the first aspect of this disclosure is SapI. In one embodiment, the first typeIIs restriction endonuclease of the first aspect of this disclosure is BsaI. In one embodiment, the second typeIIs restriction endonuclease of the first aspect of this disclosure is SapI. In one embodiment, the second typeIIs restriction endonuclease of the first aspect of this disclosure is BsaI.

In one embodiment, of the first typeIIs restriction endonuclease of the first aspect of this disclosure generates a 5'-ATG-3' overhang. In another embodiment, second typeIIs restriction endonuclease of the first aspect of this disclosure generates a 5'-CTA-3' or 5'-TTA-3' or 5'-TCA-3' or 5'-NCC-3' or 5'-NGC-3' overhang. In a specific embodiment, the first typeIIs restriction endonuclease of the first aspect of this disclosure generates a 5'-CAT-3' overhang. In a specific embodiment, the second typeIIs restriction endonuclease of the first aspect of this disclosure generates a 5'-TAG-3' or 5'-TAA-3' or 5'-TGA-3' or 5'-GGN-3' or 5'-GCN-3' overhang.

In one embodiment, the concentration of the first polynucleotide in the mixture of the first aspect of this disclosure is between 0.1 pM and 100 nM. In an alternate embodiment the concentration of the first polynucleotide in the mixture is between 0.1 pM and 10 nM.

In one embodiment, the concentration of the second polynucleotide in the mixture of the first aspect of this disclosure is between 0.1 pM and 100 nM. In an alternate embodiment the concentration of the second polynucleotide in the mixture is between 1 pM and 10 nM. In an alternate embodiment the concentration of the second polynucleotide in the mixture is between 0.1 pM and 1 µM.

In one embodiment, the concentration of the first and second typeIIs restriction endonuclease in the mixture of the first aspect of this disclosure is each independently between 0.01 U/ul and 100 U/ul. In an alternate embodiment, the concentration of the first and second typeIIs restriction endonuclease in the mixture is each independently between 0.1 U/ul and 10 U/ul. In an alternate embodiment, the concentration of the first and second typeIIs restriction endonuclease in the mixture is each independently between 0.01 U/ul and 10 U/ul.

In one embodiment, the concentration of the DNA ligase in the mixture of the first aspect of this disclosure is each independently between 1 U/ul and 400 U/ul. In an alternate embodiment, the concentration of the DNA ligase in the mixture is between 1 U/ul and 40 U/ul. In an alternate embodiment, the concentration of the DNA ligase in the mixture is between 1 U/ul and 4 U/ul.

In one embodiment, the product polynucleotide of the first aspect of this disclosure lacks a recognition sequence for the first typeIIs restriction endonuclease and lacks a recognition sequence for the second typeIIs restriction endonuclease. In one embodiment, the first typeIIs restriction endonuclease and the second typeIIs restriction endonuclease of the first aspect of this disclosure are the same. In one embodiment, the first polynucleotide of the first aspect of this disclosure is a linear molecule, wherein one end of the first polynucleotide is compatible with the first or second end of the second polynucleotide.

In one embodiment, the first polynucleotide of the first aspect of this disclosure is selected from the group consisting of vectors, expression vectors, plasmid vectors, cosmid vectors, artificial chromosomes, viral vectors, and adeno-associated viral vectors.

In one embodiment, the first aspect of this disclosure also encompasses a method of producing a product polynucleotide comprising transforming the product polynucleotide into a host cell, growing the host cell under conditions that favor the growth of host cells containing the selectable marker and, optionally, isolating the product polynucleotide from the host cell.

In one embodiment, the first aspect of this disclosure also encompasses a kit comprising a) an enzyme mixture comprising the first typeIIs restriction endonuclease that recognizes a first typeIIs recognition sequence and a DNA ligase, b) a reaction buffer, and c) instructions for incubating the enzyme mixture, the reaction buffer, and the first polynucleotide and the second polynucleotide for a predetermined length of time, and transforming the mixture into a host cell. In a specific embodiment, the kit further comprises the first polynucleotide.

The second aspect of this disclosure is a method of joining two or more polynucleotides to form a product polynucleotide. In one embodiment, the method comprises incubating a mixture for a predetermined length of time, wherein the mixture comprises a) a first polynucleotide comprising a selectable marker, b) a second polynucleotide, other than the first polynucleotide, comprising a first typeIIs recognition sequence and a second typeIIs recognition sequence, c) a first typeIIs restriction endonuclease that recognizes the first typeIIs recognition sequence and cleaves the second polynucleotide to produce a first end, and a second typeIIs restriction endonuclease that recognizes the second typeIIs recognition sequence and cleaves the second polynucleotide to produce a second end, and wherein the first end is not complementary to or is not compatible with the second end, and d) a DNA ligase. Furthermore, the mixture of the second aspect of this disclosure further comprises a third typeIIs restriction endocuclease and a fourth typeIIs endonuclease and wherein the first polynucleotide further comprises a counter-selectable marker or a double-stranded break, and a third typeIIs recognition sequence and a fourth typeIIs recognition sequence, wherein the third typeIIs restriction endonuclease and the fourth typeIIs endonuclease respectively recognize the third typeIIs recognition sequence and the fourth typeIIs recognition sequence thereby cleaving the first polynucleotide to produce a cleaved polynucleotide having a third end and a fourth end, and wherein the third end is not complementary to the fourth end, and wherein the third end is complementary to the first end.

In one embodiment, the third end of the second aspect of this disclosure comprises a single-stranded overhang comprising the sequence 5'-CAT-3'. In one embodiment the fourth end of the second aspect of this invention comprises a single-stranded overhang comprising the sequence 5'-TAA-3' or 5'-TGA-3' or 5'-TAG-3' or 5'-GGN-3' or 5'-GCN-3'.

In one embodiment, the product polynucleotide of the second aspect of this invention lacks a recognition sequence for the first, the second, the third, or the fourth typeIIs restriction endonuclease.

In one embodiment, the second polynucleotide of the second aspect of this disclosure further comprises a counter-selectable marker. In specific embodiments the counter-selectable marker is selected from the group consisting of sacB, rpsL, tetAR, pheS, thyA, lacY, gata-1, ccdB, kid and barnase. In one embodiment the selectable marker is an antibiotic resistant gene. In specific embodiments, the antibiotic resistant gene is a gene selected from the group consisting of an ampicillin resistant gene, a kanyamycin resistant gene, a chloraphenicol resistant gene, and a zeocin resistant gene.

In one embodiment, the mixture of the second aspect of this disclosure is incubated at 25° C. In another embodiment the mixture is incubated at room temperature.

In one embodiment, the predetermined length of time of the second aspect of this disclosure is between 4 minutes and 10 minutes. In another embodiment the predetermined length of time is between 10 minutes and 30 minutes. In another embodiment the predetermined length of time is between 30 minutes and 50 minutes.

In one embodiment, the first typeIIs restriction endonuclease of the second aspect of this disclosure is selected from a group consisting of BspQI, Bst6I, EarI, Eam1104I, Ksp632I, LguI, PciSI, and SapI. In one embodiment, the second typeIIs restriction endonuclease of the second aspect of this disclosure is selected from a group consisting of BspQI, Bst6I, EarI, Eam1104I, Ksp632I, LguI, PciSI, and SapI. In one embodiment, the third typeIIs restriction endonuclease of the second aspect of this invention is selected from a group consisting of BspQI, Bst6I, EarI, Eam1104I, Ksp632I, LguI, PciSI, and SapI. In one embodiment, the fourth typeIIs restriction endonuclease of the second aspect of this invention is selected from a group consisting of BspQI, Bst6I, EarI, Eam1104I, Ksp632I, LguI, PciSI, and SapI.

In one embodiment, the first typeIIs restriction endonuclease of the second aspect of this disclosure is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. In one embodiment, the second typeIIs restriction endonuclease of the second aspect of this disclosure is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. In one embodiment, the third typeIIs restriction endonuclease of the second aspect of this invention is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. In one embodiment, the fourth typeIIs restriction endonuclease of the second aspect of this invention is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstVII, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I.

In one embodiment, the first typeIIs restriction endonuclease of the second aspect of this disclosure is SapI. In one embodiment, the first typeIIs restriction endonuclease of the second aspect of this disclosure is BsaI. In one embodiment, the second typeIIs restriction endonuclease of the second aspect of this disclosure is SapI. In one embodiment, the second typeIIs restriction endonuclease of the second aspect of this disclosure is BsaI. In one embodiment, the third typeIIs restriction endonuclease of the second aspect of this invention is SapI. In one embodiment, the third typeIIs restriction endonuclease of the second aspect of this invention is BsaI. In one embodiment, the fourth typeIIs restriction endonuclease of the second aspect of this invention is SapI. In one embodiment, the fourth typeIIs restriction endonuclease of the second aspect of this invention is BsaI.

In one embodiment, the first typeIIs restriction endonuclease of the second aspect of this disclosure generates a 5'-ATG-3' overhang. In another embodiment, second typeIIs restriction endonuclease of the second aspect of this disclosure generates a 5'-CTA-3' or 5'-TTA-3' or 5'-TCA-3' or 5'-NCC-3' or 5'-NGC-3' overhang. In a specific embodiment, the first typeIIs restriction endonuclease of the second aspect of this disclosure generates a 5'-CAT-3' overhang. In a specific embodiment, the second typeIIs restriction endonuclease of the second aspect of this disclosure generates a 5'-TAG-3' or 5'-TAA-3' or 5'-TGA-3' or 5'-GGN-3' or 5'-GCN-3' overhang.

In one embodiment, the concentration of the first polynucleotide in the mixture of the second aspect of this disclosure is between 0.1 pM and 100 nM. In an alternate embodiment the concentration of the first polynucleotide in the mixture is between 0.1 pM and 10 nM.

In one embodiment, the concentration of the second polynucleotide in the mixture of the second aspect of this disclosure is between 0.1 pM and 100 nM. In an alternate embodiment the concentration of the second polynucleotide in the mixture is between 1 pM and 10 nM. In an alternate embodiment the concentration of the second polynucleotide in the mixture is between 0.1 pM and 1 µM.

In one embodiment, the concentration of the first and second typeIIs restriction endonuclease in the mixture of the second aspect of this disclosure is each independently between 0.01 U/ul and 100 U/ul. In an alternate embodiment, the concentration of the first and second typeIIs restriction endonuclease in the mixture is each independently between 0.1 U/ul and 10 U/ul. In an alternate embodiment, the concentration of the first and second typeIIs restriction endonuclease in the mixture is each independently between 0.01 U/ul and 10 U/ul.

In one embodiment, the concentration of the DNA ligase in the mixture of the second aspect of this disclosure is each independently between 1 U/ul and 400 U/ul. In an alternate embodiment, the concentration of the DNA ligase in the mixture is between 1 U/ul and 40 U/ul. In an alternate embodiment, the concentration of the DNA ligase in the mixture is between 1 U/ul and 4 U/ul.

In one embodiment, the product polynucleotide of the second aspect of this disclosure lacks a recognition sequence for the first typeIIs restriction endonuclease and lacks a recognition sequence for the second typeIIs restriction endonuclease. In one embodiment, the first typeIIs restriction endonuclease and the second typeIIs restriction endonuclease of the second aspect of this disclosure are the same. In one embodiment, the first polynucleotide of the second aspect of this disclosure is a linear molecule, wherein one end of the first polynucleotide is compatible with the first or second end of the second polynucleotide.

In one embodiment, the first polynucleotide of the second aspect of this disclosure is selected from the group consisting of vectors, expression vectors, plasmid vectors, cosmid vectors, artificial chromosomes, viral vectors, and adeno-associated viral vectors.

In one embodiment, the second aspect of this disclosure also encompasses a method of producing a product polynucleotide comprising transforming the product polynucleotide into a host cell, growing the host cell under conditions that favor the growth of host cells containing the selectable marker and, optionally, isolating the product polynucleotide from the host cell.

In one embodiment, the second aspect of this disclosure also encompasses a kit comprising a) an enzyme mixture comprising the first typeIIs restriction endonuclease that recognizes a first typeIIs recognition sequence and a DNA ligase, b) a reaction buffer, and c) instructions for incubating the enzyme mixture, the reaction buffer, and the first polynucleotide and the second polynucleotide for a predetermined length of time, and transforming the mixture into a host cell. In a specific embodiment, the kit further comprises the first polynucleotide.

The third aspect of this disclosure is a method of producing a product polynucleotide. The method of the third aspect of this disclosure comprises incubating a mixture for a predetermined length of time, transforming the mixture into a host cell, and growing the host cell under conditions that select for the presence of a selectable marker. In certain embodiments, the mixture of the third aspect of this disclosure comprises a) a first polynucleotide comprising the selectable marker, b) a second polynucleotide, other than the first polynucleotide, comprising a first typeIIs recognition sequence and a second typeIIs recognition sequence, c) a first typeIIs restriction endonuclease that recognizes the first typeIIs recognition sequence and cleaves the second polynucleotide to produce a first end, and a second typeIIs restriction endonuclease that recognizes the second typeIIs recognition sequence and cleaves the second polynucleotide to produce a second end, and wherein the first end is not complementary to or is not compatible with the second end, and d) a DNA ligase.

In one embodiment, the second polynucleotide of the third aspect of this disclosure further comprises a counter-selectable marker. In specific embodiments the counter-selectable marker is selected from the group consisting of sacB, rpsL, tetAR, pheS, thyA, lacY, gata-1, ccdB, kid and barnase. In one embodiment the selectable marker is an antibiotic resistant gene. In specific embodiments, the antibiotic resistant gene is a gene selected from the group consisting of an ampicillin resistant gene, a kanamycin resistant gene, a chloramphenicol resistant gene, and a zeocin resistant gene.

In one embodiment, the mixture of the third aspect of this disclosure is incubated at 25° C. In another embodiment the mixture is incubated at room temperature. In another embodiment the mixture is incubated at 37° C.

In one embodiment, the predetermined length of time of the fourth aspect of this invention is between 4 minutes and 10 minutes. In another embodiment the predetermined length of time is between 10 minutes and 30 minutes. In another embodiment the predetermined length of time is between 30 minutes and 90 minutes.

In one embodiment, the first typeIIs restriction endonuclease of the third aspect of this disclosure is selected from a group consisting of BspQI, Bst6I, EarI, Eam1104I, Ksp632I, LguI, PciSI, and SapI. In one embodiment, the second typeIIs restriction endonuclease of the third aspect of this disclosure is selected from a group consisting of BspQI, Bst6I, EarI, Eam1104I, Ksp632I, LguI, PciSI, and SapI. In one embodiment, the third typeIIs restriction endonuclease of the fourth aspect of this invention is selected from a group consisting of BspQI, Bst6I, EarI, Eam1104I, Ksp632I, LguI, PciSI, and SapI. In one embodiment, the fourth typeIIs restriction endonuclease of the fourth aspect of this invention is selected from a group consisting of BspQI, Bst6I, EarI, Eam1104I, Ksp632I, LguI, PciSI, and SapI.

In one embodiment, the first typeIIs restriction endonuclease of the third aspect of this disclosure is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. In one embodiment, the second typeIIs restriction endonuclease of the third aspect of this disclosure is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. In one embodiment, the third typeIIs restriction endonuclease of the fourth aspect of this invention is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. In one embodiment, the fourth typeIIs restriction endonuclease of the fourth aspect of this invention is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I.

In one embodiment, the first typeIIs restriction endonuclease of the third aspect of this disclosure is SapI. In one embodiment, the first typeIIs restriction endonuclease of the third aspect of this disclosure is BsaI. In one embodiment, the second typeIIs restriction endonuclease of the third aspect of this disclosure is SapI. In one embodiment, the second typeIIs restriction endonuclease of the third aspect of this disclosure is BsaI. In one embodiment, the third typeIIs restriction endonuclease of the fourth aspect of this invention is SapI. In one embodiment, the third typeIIs restriction endonuclease of the fourth aspect of this invention is BsaI. In one embodiment, the fourth typeIIs restriction endonuclease of the fourth aspect of this invention is SapI. In one embodiment, the fourth typeIIs restriction endonuclease of the fourth aspect of this invention is BsaI.

In one embodiment, of the first typeIIs restriction endonuclease of the third aspect of this disclosure generates a 5'-ATG-3' overhang. In another embodiment, second typeIIs restriction endonuclease of the third aspect of this disclosure generates a 5'-CTA-3' or 5'-TTA-3' or 5'-TCA-3' or 5'-NCC-3' or 5'-NGC-3' overhang. In a specific embodiment, the first typeIIs restriction endonuclease of the third aspect of this disclosure generates a 5'-CAT-3' overhang. In a specific embodiment, the second typeIIs restriction endonuclease of the third aspect of this disclosure generates a 5'-TAG-3' or 5'-TAA-3' or 5'-TGA-3' or 5'-GGN-3' or 5'-GCN-3' overhang.

In one embodiment, the concentration of the first polynucleotide in the mixture of the third aspect of this disclosure is between 0.1 pM and 100 nM. In an alternate embodiment the concentration of the first polynucleotide in the mixture is between 0.1 pM and 10 nM.

In one embodiment, the concentration of the second polynucleotide in the mixture of the third aspect of this disclosure is between 0.1 pM and 100 nM. In an alternate embodiment the concentration of the second polynucleotide in the mixture is between 1 pM and 10 nM. In an alternate embodiment the concentration of the second polynucleotide in the mixture is between 0.1 pM and 1 µM.

In one embodiment, the concentration of the first and second typeIIs restriction endonuclease in the mixture of the third aspect of this disclosure is each independently between 0.01 U/ul and 100 U/ul. In an alternate embodiment, the concentration of the first and second typeIIs restriction endonuclease in the mixture is each independently between 0.1 U/ul and 10 U/ul. In an alternate embodiment, the concentration of the first and second typeIIs restriction endonuclease in the mixture is each independently between 0.01 U/ul and 10 U/ul.

In one embodiment, the concentration of the DNA ligase in the mixture of the third aspect of this disclosure is each independently between 1 U/ul and 400 U/ul. In an alternate embodiment, the concentration of the DNA ligase in the mixture is between 1 U/ul and 40 U/ul. In an alternate embodiment, the concentration of the DNA ligase in the mixture is between 1 U/ul and 4 U/ul.

In one embodiment, the product polynucleotide of the third aspect of this disclosure lacks a recognition sequence for the first typeIIs restriction endonuclease and lacks a recognition sequence for the second typeIIs restriction endonuclease. In one embodiment, the first typeIIs restriction endonuclease and the second typeIIs restriction endonuclease of the third aspect of this disclosure are the same. In one embodiment, the first polynucleotide of the third aspect of this disclosure is a linear molecule, wherein one end of the first polynucleotide is compatible with the first or second end of the second polynucleotide.

In one embodiment, the first polynucleotide of the third aspect of this disclosure is selected from the group consisting of vectors, expression vectors, plasmid vectors, cosmid vectors, artificial chromosomes, viral vectors, and adeno-associated viral vectors.

In one embodiment, the third aspect of this disclosure also encompasses a method of producing a product polynucleotide comprising transforming the product polynucleotide into a host cell, growing the host cell under conditions that favor the growth of host cells containing the selectable marker and, optionally, isolating the product polynucleotide from the host cell.

In one embodiment, the third aspect of this disclosure also encompasses a kit comprising a) an enzyme mixture comprising the first typeIIs restriction endonuclease that recognizes a first typeIIs recognition sequence and a DNA ligase, b) a reaction buffer, and c) instructions for incubating the enzyme mixture, the reaction buffer, and the first polynucleotide and the second polynucleotide for a predetermined length of time, and transforming the mixture into a host cell. In a specific embodiment, the kit further comprises the first polynucleotide.

The fourth aspect of this disclosure is a method of producing a product polynucleotide. The method of the fourth aspect of this disclosure comprises incubating a mixture for a predetermined length of time, transforming the mixture into a host cell, and growing the host cell under conditions that select for the presence of a selectable marker. In certain embodiments, the mixture of the fourth aspect of this disclosure comprises a) a first polynucleotide comprising the selectable marker, b) a second polynucleotide, other than the first polynucleotide, comprising a first typeIIs recognition sequence and a second typeIIs recognition sequence, c) a first typeIIs restriction endonuclease that recognizes the first typeIIs recognition sequence and cleaves the second polynucleotide to produce a first end, and a second typeIIs restriction endonuclease that recognizes the second typeIIs recognition sequence and cleaves the second polynucleotide to produce a second end, and wherein the first end is not complementary to or is not compatible with the second end, and d) a DNA ligase. Furthermore, the mixture of the fourth aspect of this disclosure further comprises a third typeIIs restriction endocuclease and a fourth typeIIs endonuclease. In specific embodiments, the first polynucleotide further comprises a) a counter-selectable marker or a double-stranded break, and b) a third typeIIs recognition sequence and a fourth typeIIs recognition sequence, wherein the third typeIIs restriction endonuclease and the fourth typeIIs endonuclease respectively recognize the third typeIIs recognition sequence and the fourth typeIIs recognition sequence thereby cleaving the first polynucleotide to produce a cleaved polynucleotide having a third end and a fourth end, and wherein the third end is not complementary to the fourth end, and wherein the third end is complementary to the first end.

In one embodiment, the third end of the fourth aspect of this disclosure comprises a single-stranded overhang comprising the sequence 5'-CAT-3'. In one embodiment the fourth end of the fourth aspect of this disclosure comprises a single-stranded overhang comprising the sequence 5'-TAA-3' or 5'-TGA-3' or 5'-TAG-3' or 5'-GGN-3' or 5'-GCN-3'.

In one embodiment, the product polynucleotide of the fourth aspect of this disclosure lacks a recognition sequence for the first, the second, the third, or the fourth typeIIs restriction endonuclease.

In one embodiment, the second polynucleotide of the fourth aspect of this disclosure further comprises a counter-selectable marker. In specific embodiments the counter-selectable marker is selected from the group consisting of sacB, rpsL, tetAR, pheS, thyA, lacY, gata-1, ccdB, kid and barnase. In one embodiment the selectable marker is an antibiotic resistant gene. In specific embodiments, the antibiotic resistant gene is a gene selected from the group consisting of an ampicillin resistant gene, a kanyamycin resistant gene, a chloraphenicol resistant gene, and a zeocin resistant gene.

In one embodiment, the mixture of the fourth aspect of this disclosure is incubated at 25° C. In another embodiment the mixture is incubated at room temperature.

In one embodiment, the predetermined length of time of the fourth aspect of this disclosure is between 4 minutes and 10 minutes. In another embodiment the predetermined length of time is between 30 minutes and 50 minutes.

In one embodiment, the first typeIIs restriction endonuclease of the fourth aspect of this disclosure is selected from a group consisting of BspQI, Bst6I, EarI, Eam1104I, Ksp632I, LguI, PciSI, and SapI. In one embodiment, the second typeIIs restriction endonuclease of the fourth aspect of this disclosure is selected from a group consisting of BspQI, Bst6I, EarI, Eam1104I, Ksp632I, LguI, PciSI, and SapI.

In one embodiment, the first typeIIs restriction endonuclease of the fourth aspect of this disclosure is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I. In one embodiment, the second typeIIs restriction endonuclease of the fourth aspect of this disclosure is selected from a group consisting of AarI, Acc36I, AceIII, AspBHI, Alw26I, BbvI, BcoDI, BsmAI, BsmFI, BbsI, BfuAI, BsaI, Bsa-HF, BsmBI, Btg2I, BmsI, BseXI, BsIFI, BsoMAI, Bst71I, BstMAI, BstV1I, BbvII, BpiI, BpuAI, Bso31I, BspTNI, BstV2I, BveI, Eco31I, Esp3I, FspEI, FokI, FaqI, LpnPI, LweI, MspJI, R9896, SfaNI, SgeI, SgrTI, and Sth132I.

In one embodiment, the first typeIIs restriction endonuclease of the fourth aspect of this disclosure is SapI. In one embodiment, the first typeIIs restriction endonuclease of the fourth aspect of this disclosure is BsaI. In one embodiment, the second typeIIs restriction endonuclease of the fourth aspect of this disclosure is SapI. In one embodiment, the second typeIIs restriction endonuclease of the fourth aspect of this disclosure is BsaI.

In one embodiment, of the first typeIIs restriction endonuclease of the fourth aspect of this disclosure generates a 5'-ATG-3' overhang. In another embodiment, second typeIIs restriction endonuclease of the fourth aspect of this disclosure generates a 5'-CTA-3' or 5'-TTA-3' or 5'-TCA-3' or 5'-NCC-3' or 5'-NGC-3' overhang. In a specific embodiment, the first typeIIs restriction endonuclease of the fourth aspect of this disclosure generates a 5'-CAT-3' overhang. In a specific embodiment, the second typeIIs restriction endonuclease of the fourth aspect of this disclosure generates a 5'-TAG-3' or 5'-TAA-3' or 5'-TGA-3' or 5'-GGN-3' or 5'-GCN-3' overhang.

In one embodiment, the concentration of the first polynucleotide in the mixture of the fourth aspect of this disclosure is between 0.1 pM and 100 nM. In an alternate embodiment the concentration of the first polynucleotide in the mixture is between 0.1 pM and 10 nM.

In one embodiment, the concentration of the second polynucleotide in the mixture of the fourth aspect of this disclosure is between 0.1 pM and 100 nM. In an alternate embodiment the concentration of the second polynucleotide in the mixture is between 1 pM and 10 nM. In an alternate embodiment the concentration of the second polynucleotide in the mixture is between 0.1 pM and 1 µM.

In one embodiment, the concentration of the first and second typeIIs restriction endonuclease in the mixture of the fourth aspect of this disclosure is each independently between 0.01 U/ul and 100 U/ul. In an alternate embodiment, the concentration of the first and second typeIIs restriction endonuclease in the mixture is each independently between 0.1 U/ul and 10 U/ul. In an alternate embodiment, the concentration of the first and second typeIIs restriction endonuclease in the mixture is each independently between 0.01 U/ul and 10 U/ul.

In one embodiment, the concentration of the DNA ligase in the mixture of the fourth aspect of this disclosure is each independently between 1 U/ul and 400 U/ul. In an alternate embodiment, the concentration of the DNA ligase in the mixture is between 1 U/ul and 40 U/ul. In an alternate embodiment, the concentration of the DNA ligase in the mixture is between 1 U/ul and 4 U/ul.

In one embodiment, the product polynucleotide of the fourth aspect of this disclosure lacks a recognition sequence for the first typeIIs restriction endonuclease and lacks a recognition sequence for the second typeIIs restriction endonuclease, and lacks a recognition sequence for the third typeIIs restriction endonuclease, and lacks a recognition sequence for the fourth typeIIs restriction endonuclease. In one embodiment, the first typeIIs restriction endonuclease and the second typeIIs restriction endonuclease of the fourth aspect of this disclosure are the same. In one embodiment, the first typeIIs restriction endonuclease and the second typeIIs restriction endonuclease and the third typeIIs restriction endonuclease and the fourth typeIIs restriction endonuclease of the fourth aspect of this invention are the same.

In one embodiment, the first polynucleotide of the fourth aspect of this disclosure is selected from the group consisting of vectors, expression vectors, plasmid vectors, cosmid vectors, artificial chromosomes, viral vectors, and adeno-associated viral vectors.

In one embodiment, the fourth aspect of this disclosure also encompasses a method of producing a product polynucleotide comprising transforming the product polynucleotide into a host cell, growing the host cell under conditions that favor the growth of host cells containing the selectable marker and, optionally, isolating the product polynucleotide from the host cell.

In one embodiment, the fourth aspect of this disclosure also encompasses a kit comprising a) an enzyme mixture comprising the first typeIIs restriction endonuclease that recognizes a first typeIIs recognition sequence and a DNA ligase, b) a reaction buffer, and c) instructions for incubating the enzyme mixture, the reaction buffer, and the first polynucleotide and the second polynucleotide for a predetermined length of time, and transforming the mixture into a host cell. In a specific embodiment, the kit further comprises the first polynucleotide or the second polynucleotide.

The above described embodiments are non-limiting examples of this disclosure.

5.2 Definitions

Use of the singular forms "a," "an," and "the" include plural references unless the context clearly dictates otherwise. Thus, for example, reference to "a polynucleotide" includes a plurality of polynucleotides, reference to "a substrate" includes a plurality of such substrates, and reference to "a variant" includes a plurality of variants.

Terms such as "connected," "attached," "linked," and "conjugated" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each sub range between such values. The upper and lower limits of any range can independently be included in or excluded from the range, and each range where either, neither or both limits are included is also encompassed within the disclosure. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the disclosure. Where a combination is disclosed, each sub combination of the elements of that combination is also specifically disclosed and is within the scope of the disclosure. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise herein, all technical and scientific terms used herein have the same meaning as commonly understood by one of ordinary skill in the art to which this invention belongs. Singleton, et al., *Dictionary of Microbiology and Molecular Biology*, 2nd Ed., John Wiley and Sons, New York (1994), and Hale & Marham, *The Harper Collins Dictionary of Biology*, Harper Perennial, NY, 1991, provide one of skill with a general dictionary of many of the terms used in this disclosure. Although any methods and materials similar or equivalent to those described herein can be used in the practice or testing of the present disclosure, the preferred methods and materials are described. Unless otherwise indicated, nucleic acids are written left to right in 5' to 3' orientation; amino acid sequences are written left to right in amino to carboxy orientation, respectively. The terms defined immediately below are more fully defined by reference to the specification as a whole.

The terms "polynucleotide," "oligonucleotide," "nucleic acid" and "nucleic acid molecule" and "gene" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2', 5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates), with negatively charged linkages (e.g., phosphorothioates, phosphorodithioates), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine), those with intercalators (e.g., acridine, psoralen), those containing chelates (of, e.g., metals, radioactive metals, boron, oxidative metals), those containing alkylators, those with modified linkages (e.g., alpha anomeric nucleic acids), as well as unmodified forms of the polynucleotide or oligonucleotide.

The terms "polynucleotide," "oligonucleotide," "nucleic acid" and "nucleic acid molecule" and "gene" refer to the entire sequence or gene or a fragment thereof. The fragment thereof can be a functional fragment.

Where the polynucleotides are to be used to express encoded proteins, nucleotides that can perform that function or which can be modified (e.g., reverse transcribed) to perform that function are used. Where the polynucleotides are to be used in a scheme that requires that a complementary strand be formed to a given polynucleotide, nucleotides are used which permit such formation.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., where one or more of the hydroxyl groups are replaced with halogen, aliphatic groups, or is functionalized as ethers, amines, or the like. The term "nucleotidic unit" is intended to encompass nucleosides and nucleotides.

Standard A-T and G-C base pairs form under conditions which allow the formation of hydrogen bonds between the N3—H and C4-oxy of thymidine and the NI and C6—NH2, respectively, of adenosine and between the C2-oxy, N3 and C4—NH2, of cytidine and the C2—$NH_2$, N'—H and C6-oxy, respectively, of guanosine. Thus, for example, guanosine (2-amino-6-oxy-9-.beta.-D-ribofuranosyl-purine) may be modified to form isoguanosine (2-oxy-6-amino-9-.beta.-D-ribofuranosyl-purine). Such modification results in a nucleoside base which will no longer effectively form a standard base pair with cytosine. However, modification of cytosine (1-.beta.-D-ribofuranosyl-2-oxy-4-amino-pyrimidine) to form isocytosine (1-.beta.-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al., hereby incorporated by reference in its entirety). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al., 1993, J. Am. Chem. Soc. 115:4461-4467 and references cited therein; and isoguanine nucleotides may be prepared using the method described by Switzer et al., 1993, supra, and Mantsch et al., 1993, Biochem. 14:5593-5601, or by the method described in U.S. Pat. No. 5,780,610 to Collins et al., each of which is hereby incorporated by reference in its entirety. Other nonnatural base pairs may be synthesized by the method described in Piccirilli et al., 1990, Nature 343:33-37, hereby incorporated by reference in its entirety, for the synthesis of 2,6-diaminopyrimidine and its complement (1-methylpyrazolo-[4,3] pyrimidine-5,7-(4H,6H)-dione. Other such modified nucleotidic units which form unique base pairs are known, such as those described in Leach et al. (1992) J. Am. Chem. Soc. 114:3675-3683 and Switzer et al., supra.

The phrase "DNA sequence" refers to a contiguous nucleic acid sequence. The sequence can be either single stranded or double stranded, DNA or RNA, but double stranded DNA sequences are preferable. The sequence can be an oligonucleotide of 6 to 20 nucleotides in length to a full length genomic sequence of thousands or hundreds of thousands of base pairs.

The term "Vector" or "DNA Vector" refers to a DNA sequence that is used to perform a "carrying" function for another polynucleotide. For example vectors are often used to allow a polynucleotide to be propagated within a living cell.

The term "Host" refers to any prokaryotic or eukaryotic organism that can be a recipient of a nucleic acid. A "host", as the term is used herein, includes prokaryotic or eukaryotic organisms that can be genetically engineered. For examples of such hosts, see Maniatis et al., Molecular Cloning. A Laboratory Manual, Cold Spring Harbor Laboratory, Cold Spring Harbor, N.Y. (1982). As used herein, the terms "host," "host cell," "host system" and "expression host" are used interchangeably.

The term "Overhang" or "DNA Overhang" refers to the single-stranded portion at the end of a double-stranded DNA molecule. Complementary overhangs are those which will base-pair with each other.

The term "Scar" refers to extra DNA sequences that are left as part of a polynucleotide construct that are an unavoidable consequence of the construction method rather than being incorporated because of their desirable functional properties. For example recombinases, integrases and restriction endonucleases often have recognition sequences that remain within the sequence of a polynucleotide that is constructed using the action of said recombinases, integrases and restriction endonucleases. The term "Scar Size" refers to the length of the extra DNA sequences. For example a scar size of 34 base pairs is left in a construct with a recognition sequence for Cre recombinase, a scar size of 25 base pairs is added on when attB integrase is used. Scars can interfere with the functions of other sequence elements within the construct.

The term "Recognition sequence" refers to a particular DNA sequences which are recognized (and bound by) a protein, DNA, or RNA molecule, including a restriction endonuclease, a modification methylase, and a recombinase. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., Current Opinion in Biotechnology 5:521-527 (1994). Other examples of recognition sequences are the attB, attP, attL, and attR sequences which are recognized by the integrase of bacteriophage lambda. AttB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins IHF, FIS, and Xis. See Landy, Current Opinion in Biotechnology 3:699-707 (1993).

The term "Recombinase" refers to an enzyme which catalyzes the exchange of DNA segments at specific recombination sites.

The term "Recombinational Cloning" refers to a method described herein, whereby segments of DNA molecules are exchanged, inserted, replaced, substituted or modified, in vitro or in vivo.

The term "Recombination proteins" includes excisive or integrative proteins, enzymes, co-factors or associated proteins that are involved in recombination reactions involving one or more recombination sites. See, Landy (1994), infra.

The term "Repression cassette" refers to a DNA segment that contains a repressor of a Selectable marker present in the subcloning vector.

The term "Selectable marker" refers to a DNA segment that allows one to select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions. Examples of Selectable markers include but are not limited to: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as beta-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1-5 above (e.g., antisense oligonucleotides); (7) DNA segments that bind products that modify a substrate (e.g. restriction endonucleases); (8) DNA segments that can be used to isolate a desired molecule (e.g. specific protein binding sites); (9) DNA segments that encode a specific nucleotide sequence which can be otherwise non-functional (e.g., for PCR amplification of subpopulations of molecules); and/or (10) DNA segments, which when absent, directly or indirectly confer sensitivity to particular compounds.

The term "Counter Selectable Marker" refers to a DNA sequence that confers a selective disadvantage upon a host cell. Examples of counter-selectable markers include sacB, rpsL, tetAR, pheS, thyA, gata-1, ccdB, kid and barnase (Bernard, 1995, Journal/Gene, 162: 159-160; Bernard et al., 1994. Journal/Gene, 148: 71-74; Gabant et al., 1997, Journal/Biotechniques, 23: 938-941; Gababt et al., 1998, Journal/Gene, 207: 87-92; Gababt et al., 2000, Journal/Biotechniques, 28: 784-788; Galvao and de Lorenzo, 2005, Journal/Appl Environ Microbiol, 71: 883-892; Hartzog et al., 2005, Journal/Yeat, 22:789-798; Knipfer et al., 1997, Journal/Plasmid, 37: 129-140; Reyrat et al., 1998, Journal/Infect Immun, 66: 4011-4017; Soderholm et al., 2001, Journal/Biotechniques, 31: 306-310, 312; Tamura et al., 2005, Journal/Appl Environ Microbiol, 71: 587-590; Yazynin et al., 1999, Journal/FEBS Lett, 452: 351-354). Counter-selectable markers often confer their selective disadvantage in specific contexts. For example they may confer sensitivity to compounds that can be added to the environment of the host cell, or they may kill a host with one genotype but not kill a host with a different genotype. Conditions which do not confer a selective disadvantage upon a cell carrying a counter-selectable marker are described as "permissive". Conditions which do confer a selective disadvantage upon a cell carrying a counter-selectable marker are described as "restrictive".

The term "Selection scheme" refers to any method which allows selection, enrichment, or identification of a desired Product or Product(s) from a mixture containing the Insert Donor, Vector Donor, and/or any intermediates, (e.g. a Cointegrate) Byproducts. The selection schemes of one preferred embodiment have at least two components that are either linked or unlinked during recombinational cloning. One component is a Selectable marker. The other component controls the expression in vitro or in vivo of the Selectable marker, or survival of the cell harboring the plasmid carrying the Selectable marker. Generally, this controlling element will be a repressor or inducer of the Selectable marker, but other means for controlling expression of the Selectable marker can be used. Whether a repressor or activator is used will depend on whether the marker is for a positive or negative selection, and the exact arrangement of the various DNA segments, as will be readily apparent to those skilled in the art. A preferred requirement is that the selection scheme results in selection of or enrichment for only one or more desired Products. As defined herein, to select for a DNA molecule includes (a) selecting or enriching for the presence of the desired DNA molecule, and (b) selecting or enriching against the presence of DNA molecules that are not the desired DNA molecule.

Examples of such toxic gene products are well known in the art, and include, but are not limited to, restriction endonucleases (e.g., DpnI) and genes that kill hosts in the absence of a suppressing function, e.g., kicB. A toxic gene can alternatively be selectable in vitro, e.g., a restriction site.

The term "expression system" refers to any in vivo or in vitro biological system that is used to produce one or more polypeptide encoded by a polynucleotide.

The term "annealing temperature" or "melting temperature" or "transition temperature" refers to the temperature at which a pair of nucleic acids is in a state intermediate between being fully annealed and fully melted. The term refers to the behavior of a population of nucleic acids: the "annealing temperature" or "melting temperature" or "transition temperature" is the temperature at which 50% of the molecules are annealed and 50% are separate. Annealing temperatures can be determined experimentally. There are also methods well known in the art for calculating these temperatures.

Non-limiting examples of temperature used during the incubation steps described herein are 4° C., or 5° C., or 6° C., or 7° C., or 8° C., or 9° C., or 10° C., or 11° C., or 12° C., or 13° C., or 14° C., or 15° C., or 16° C., or 17° C., or 18° C., or 19° C., or 20° C., or 21° C., or 22° C., or 23° C., or 24° C., or 25° C., or 26° C., or 27° C., or 28° C., or 29° C., or 30° C., or 31° C., or 32° C., or 33° C., or 34° C., or 35° C., or 36° C., or 37° C., or 38° C., or 39° C., or 40° C., or 41° C., or 42° C., or 43° C., or 44° C., or 45° C.

The term "translation" refers to the process by which a polypeptide is synthesized by a ribosome 'reading' the sequence of a polynucleotide.

The term "selectable protein" refers to a protein that provides a physical, chemical or biological method for selecting cells on the basis of how much of the selectable protein is expressed.

The term "coupling element" refers to a DNA sequence that allows the expression of a first polypeptide to be linked to the expression of a second polypeptide. Internal ribosome binding sites and cis-acting hydrolase elements are examples of coupling elements.

The phrase "predetermined time period" or "predetermined length of time" refers to a specified amount of time and the terms can be used interchangeably. A "predetermined period of time" can be on the order of seconds, minutes, hours, days, weeks, or months. For example, a "predetermined time period" can be between 1 and 59 minutes, or any increment between 1 and 2 hours, or any increment between 2 and 4 hours, or any increment between 4 and 6 hours, or any increment between 6 and 12 hours, or any increment between 12 and 24 hours, or any increment between 1 day and 2 days, or any increment between 2 days and 4 days, and any increment between 4 days and 7 days, and any increment between 1 week and 4 weeks, and any increment between 1 month and 12 months, or any combination of incremental time periods therein. In specific embodiments, the predetermined period of time is 1 minute, or 2 minutes, or 3 minutes, or 4 minutes, or 5 minutes, or 6 minutes, or 7 minutes, or 8 minutes, or 9 minutes, or 10 minutes, or 11 minutes, or 12 minutes, or 13 minutes, or 14 minutes, or 15 minutes, or 16 minutes, or 17 minutes, or 18 minutes, or 19 minutes, or 20 minutes, or 21 minutes, or 22 minutes, or 23 minutes, or 24 minutes, or 25 minutes, or 26 minutes, or 27 minutes, or 28 minutes, or 29 minutes, or 30 minutes, or 31 minutes, or 32 minutes, or 33 minutes, or 34 minutes, or 35 minutes, or 36 minutes, or 37 minutes, or 38 minutes, or 39 minutes, or 40 minutes, or 41 minutes, or 42 minutes, or 43 minutes, or 44 minutes, or 45 minutes, or any combination thereof.

The term "typeIIs restriction enzyme" is used herein to refer to any restriction enzyme that cleaves DNA at a defined distance outside its recognition sequence, and whose recognition sequence is non-palindromic.

The term "compatible ends" is used herein to describe two ends of polynucleotide molecules that are both blunt or that both possess overhangs of the same length and directionality (i.e. both are 5'-overhangs, or both are 3'-overhangs) and with perfectly complementary sequences, such that said DNA ends form standard Watson-Crick base pairs (i.e. C with G and T or U with A). Ends are "compatible" with each other when these criteria are met. When at least one end of a compatible pair is phosphorylated, the ends can be joined by a DNA ligase and are "ligatable ends".

Complementarity or Complementary sequences is a property shared between two nucleic acid sequences, such that when they are aligned antiparallel to each other, the nucleotide bases at each position will be complementary. Two bases are complementary if they form Watson-Crick base pairs (i.e. C with G and T or U with A).

The terms "pseudo-ligatable ends" or "pseudo-compatible ends" are used herein to describe two ends of polynucleotide molecules that possess overhangs of the same length and directionality (i.e. both are 5'-overhangs, or both are 3'-overhangs) and with imperfectly paired complementary sequences, such that annealing of said DNA ends requires at least one non-standard Watson-Crick base pair (i.e. T or U with G), but which can nevertheless can be joined by a DNA ligase, albeit at a lower efficiency than ends that form only standard Watson-Crick base pairs.

The term "polynucleotide vector" is used herein to describe a polynucleotide comprising a selectable marker.

The term "Daughter Vector" is used herein to describe a polynucleotide comprising a first typeIIs restriction site and a second typeIIs restriction site, wherein cleavage of said Daughter Vector with said first and second typeIIs restriction enzymes produces a first polynucleotide vector fragment, referred to herein as a "Daughter Vector Fragment", which comprises a selectable marker but lacks said first and second typeIIs restriction sites, and a second polynucleotide fragment, referred to herein as a "Stuffer Fragment".

The term "Daughter Vector Fragment" is used herein to describe a polynucleotide fragment produced by restriction digestion of a polynucleotide with one or more typeIIs restriction enzymes, such that said Daughter Vector Fragment comprises a selectable marker but lacks recognition sites for said one or more typeIIs restriction enzymes.

The term "Mother Polynucleotide" is used herein to describe a polynucleotide comprising a third typeIIs restriction site and a fourth typeIIs restriction site, wherein cleavage of said Mother Polynucleotide with said third and fourth typeIIs restriction enzymes produces an "Insert Fragment" lacking said third and fourth typeIIs restriction sites, and another polynucleotide fragment, referred to herein as a "Discard Fragment".

The term "Insert Fragment" is used herein to describe a polynucleotide fragment produced by restriction digestion of a polynucleotide with one or more typeIIs restriction enzymes such that said Insert Fragment lacks recognition sites for said one or more typeIIs restriction enzymes, and such that it can be ligated with a Daughter Vector Fragment, either individually or in combination with other Insert Fragments.

The term "Product Polynucleotide" is used herein to describe the ligation product of a Daughter Vector Fragment and one or more Insert Fragments.

A One Pot Reaction Mixture is used herein to describe either a mixture comprising
(i) a Daughter Vector,
(ii) a Mother Polynucleotide,
(iii) one or more typeIIs restriction enzymes that release an Insert Fragment from the Mother Polynucleotide and a Daughter Vector Fragment from the Daughter Vector, and
(iv) a DNA ligase
or a mixture comprising:
(i) a Daughter Vector Fragment,
(ii) a Mother Polynucleotide,
(iii) one or more typeIIs restriction enzymes that release an Insert Fragment from the Mother Polynucleotide, and
(iv) a DNA ligase As used herein, the term "One unit" as applied to restriction endonucleases is defined as the amount of enzyme required to digest 1 µg of λ DNA in 1 hour at 37° C. in a total reaction volume of 50 µl.

As used herein, the term "One unit" as it refers to a DNA ligase is defined as the amount of enzyme required to give 50% ligation of the 12-base pair cohesive ends of 1 µg of BstEII-digested λ DNA in a total reaction volume of 50 µl in 15 minutes at 45° C.

The term "Contiguous Polypeptide" is used herein to describe an amino acid sequence that is encoded in the same open reading frame of a single physical polynucleotide sequence without any stop codons.

5.3 Description 5.3.1 One Pot Reaction Mixtures

An Insert Fragment may be ligated with a Daughter Vector Fragment to form a Product Polynucleotide if the two fragments have ends that are compatible with each other. Methods have been described in the art where a restriction enzyme and a ligase are used sequentially to cleave and then join polynucleotides, and the two reactions are performed in the same vessel (see U.S. Pat. App. 20110020830; U.S. Pat. App. 20110033909; Geertsma et al., Biochem 50:3272-3278, 2011 and Jin et al., Prot. Exp. And Purif. 78:69-77, 2011). The benefit claimed for such a method is that the cleavage reactions and ligase reactions are carried out without need to change the reaction buffer. The cited references specifically teach away from performing both reactions at the same time, as they teach a step that inactivates the restriction enzyme prior to addition of the ligase. In contrast to the published art, in a preferred embodiment of the disclosure described herein, one or more typeIIs restriction enzyme and a DNA ligase are both present and active in the same reaction mixture. This is advantageous because it helps to drive the reaction toward the formation of the desired Product Polynucleotide.

In a preferred embodiment a DNA ligase and a typeIIs restriction endonuclease with a 7 bp recognition sequence (for example SapI) are present in the same reaction. An advantage of using SapI restriction endonuclease over other enzymes such as BsaI (Engler et. al., PLoS ONE 3(11), 2008) is that SapI has a non-palindromic 7 bp recognition sequence compared to a 6 bp non-palindromic recognition sequence for BsaI. This means that the recognition sequence for SapI occurs at an average frequency of one in 8192 base pairs: four times less frequently than the recognition sequence for enzymes that have 6 bp recognition sequences including BsaI. The advantage of using SapI over BsaI is that it is four times less likely that SapI will cut inside a typical gene sized DNA fragment. This means that a gene sequence is less likely to be cut in an unintended place, which makes the method more broadly useful when SapI rather than BsaI is used.

A second benefit of SapI over BsaI is that SapI generates a 3 bp overhang, compared with a 4 bp overhang for BsaI. SapI can therefore be used to create overhangs that consist of exactly one codon, which minimizes the scar size for example when open reading frames are being joined. In contrast, because BsaI has a 4 bp overhang, a junction within an open reading frame that is created using BsaI will have to overlap with at least 2 codons.

Open reading frames all begin with a methionine codon (which is 5'-ATG-3') and end with a stop codon (5'-TAG-3', or 5'-TAA-3', or 5'-TGA-3'). Thus one preferred embodiment comprises a plurality of Daughter Vectors that can be cut to produce Daughter Vector Fragments that are compatible with any Insert Fragment that has an overhang comprising 5'-ATG-3' at one end, and 5'-CTA-3', or 5'-TTA-3', or 5'-TCA-3' at the other end. This will allow any open reading frame to be seamlessly subcloned into any Daughter vector.

Another preferred embodiment comprises a plurality of Daughter Vectors that can be cut to produce Daughter Vector Fragments that have overhangs comprising 5'-CAT-3' at one end (complementary to 5'-ATG-3' encoding methionine at the start of an open reading frame), and 5'-GGN-3', or 5'-GCN-3' at the other end. These overhangs encode either a glycine (5'-GGN-3'), or an alanine (5'-GCN-3'). The use of a codon encoding a small amino acid instead of a stop codon means that Daughter vectors may encode C-terminal fusions, a feature that is not available if the open reading frame encoded in the Insert Fragment ends in a stop codon.

It is particularly important to avoid overhangs where the two ends of the Daughter Vector Fragment can ligate with each other, since this would result in a circular DNA molecule that can transform a host cell, but which does not carry an insert. Included in this restriction, the two ends of the cut Daughter Vector should not be pseudo-complementary. That is, they should not be complementary even if T-G is considered also as a complementary base pair. For example if the Daughter Vector Fragment has a 5'-CAT-3' overhang at one end, to be complementary with a 5'-ATG-3' overhang from an insert, the overhang at the other end of the insert should be neither 5'-ATG-3', which is a perfect complement to 5'-CAT-3', nor 5'-GTG-3', because 5'-GTG-3' will complement 5'-CAT-3' with a T-G base pair. Similarly if a Daughter Vector Fragment has a 5'-GGT-3' at one end, the other end should not be the perfectly complementary 5'-ACC-3', but nor should it be 5'-ATT-3' or 5'-GTT-3' or 5'-ACT-3' or 5'-GCT-3' or 5'-ATC-3' or 5'-GTC-3' or 5'-GCC-3', since all of these overhangs will complement 5'-GGT-3' by incorporating one or more T-G base pairs.

In preferred embodiments the Product Polynucleotide lacks recognition sites for the typeIIs restriction enzyme present in the mixture, and therefore is not digested. In preferred embodiments the Mother Polynucleotide in the mixture comprises sites for a typeIIs restriction enzyme present in the mixture, wherein cleavage of the Mother Polynucleotide with the typeIIs restriction enzyme releases an Insert Fragment that lacks sites for the typeIIs restriction enzyme present in the mixture. Thus if the Insert Fragment ligates with other digestion products of the Mother Polynucleotide to reconstitute all or a part of the Mother Polynucleotide, the Mother Polynucleotide will be digested again by the typeIIs restriction enzymes in the reaction to again produce the Insert Fragment. In some embodiments the mixture comprises a predigested and purified Daughter Vector Fragment. In other embodiments the mixture comprises a Daughter Vector that comprises one or more site recognized by the typeIIs restriction enzyme present in the mixture, wherein cleavage of the Daughter Vector with the typeIIs restriction enzyme releases a Daughter Vector Fragment that lacks sites for the typeIIs restriction enzyme present in the mixture. Thus if the Daughter Vector Fragment ligates with other digestion products of the Daughter Vector to reconstitute all or a part of the Daughter Vector, the typeIIs restriction enzyme(s) present in the reaction will re-digest the Daughter Vector to produce again the Daughter Vector Fragment (FIG. 4).

For example, a Product Polynucleotide can be formed in a One Pot Reaction Mixture comprising:
1. A Daughter Vector
2. A Mother Polynucleotide
3. TypeIIs restriction enzymes that release an Insert Fragment from the Mother Polynucleotide, and a Daughter Vector Fragment from the Daughter Vector
4. A DNA ligase Alternatively a Product Polynucleotide can be formed in a One Pot Reaction Mixture comprising:
1. A Daughter Vector Fragment
2. A Mother Polynucleotide
3. TypeIIs restriction enzymes that release an Insert Fragment from the Mother Polynucleotide
4. A DNA ligase The Mother Polynucleotide may be a linear fragment of DNA, or it may be a closed circle of DNA. The Mother polynucleotide may be produced by DNA synthesis, or it may be produced by PCR amplification of a template. PCR amplification may be used to add typeIIs restriction sites and sequences that will produce an Insert Fragment with overhangs that are compatible with the ends of a Daughter Vector Fragment following digestion of the Mother Polynucleotide with typeIIs restriction enzymes.

The Mother Polynucleotide may additionally comprise a selectable marker to facilitate propagation of the Mother Polynucleotide within a host cell. The selectable marker is preferably not contained within the Insert Fragment sequence.

Non-limiting examples of Selectable markers include: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as beta.-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1-5 above (e.g., antisense oligonucleotides); (7) DNA segments that bind products that modify a substrate (e.g. restriction endonucleases); (8) DNA segments that can be used to isolate a desired molecule (e.g. specific protein binding sites); (9) DNA segments that encode a specific nucleotide sequence which can be otherwise non-functional (e.g., for PCR amplification of subpopulations of molecules); and/or (10) DNA segments, which when absent, directly or indirectly confer sensitivity to particular compounds. In some embodiments the selectable marker is an antibiotic, for example selected from but not limited to ampicillin or kanamycin or chloramphenicol or zeocin.

The Product Polynucleotide may be obtained by transforming the One Pot Reaction Mixture into a host cell. For transformation into a host cell it may be advantageous for the Product Polynucleotide to be circular, in some embodiments the Product Polynucleotide may be linear.

When a One Pot Reaction Mixture is transformed into a host cell, in addition to the Product Polynucleotide the reaction may contain Mother Polynucleotide, Daughter Vector, Stuffer Fragments and Discard Fragments. It is advantageous to prepare One Pot Reaction Mixtures such that the Product Polynucleotide enjoys a selective advantage in the host relative to the other polynucleotides in the mixture. This can be accomplished in a number of ways.

For example, if the Daughter Vector Fragment and the Product Polynucleotide comprise a first selectable marker and the Mother Polynucleotide comprises a second selectable marker, it is preferable that the first and second selectable markers are different. After transformation of the mixture into the host cell, it is advantageous to grow the host cell under conditions where the first selectable marker provides a growth advantage, but the second selectable marker does not.

The Mother Polynucleotide may additionally comprise a counter-selectable marker to prevent propagation of the Mother Polynucleotide within a host cell. In certain embodiments, the counter-selectable marker is sacB, rpsL, tetAR, pheS, thyA, lacY, gata-1, ccdB, kid or barnase. In some embodiments said Mother Polynucleotide further comprises a double-stranded DNA break, or a dephosphorylated double-stranded DNA break, or a counter-selectable marker within said Discard Fragment sequence, in some embodiments said counter-selectable marker is sacB, rpsL, tetAR, pheS, thyA, lacY, gata-1, ccdB, kid or barnase. In some embodiments said mixture is transformed into a host cell that is grown under conditions that are restrictive for growth of cells containing a counter-selectable marker, thereby preventing the growth of cells containing DNA comprising said Stuffer Fragment or said Discard Fragment. In certain embodiments, the counter-selectable marker is rpsL that confers sensitivity to streptomycin. In certain embodiments, the counter-selectable marker is pheS that confers sensitivity to p-chloro-phenylalanine, a toxic form of amino acid phenylalanine.

For example, if the Mother Polynucleotide comprises a counter-selectable marker that is not present or not functional in the Insert Fragment sequence, then cells that have been transformed with the Mother Polynucleotide may be selected against by growing the transformed cells under conditions that are restrictive for the counter-selectable marker. Useful counter-selectable markers include sacB, rpsL, tetAR, pheS, thyA, lacY, gata-1, ccdB, kid or barnase. If the Mother Polynucleotide comprises a counter-selectable marker, then it is possible to use the same selectable marker in both the Mother Polynucleotide and the Product Polynucleotide, and to select for cells that are carrying only the Product Polynucleotide by selecting for the selectable marker and against the counter-selectable marker.

A Daughter Vector may also comprise a counter-selectable marker that is not present or not functional in the Daughter Vector Fragment sequence, or in the Product Polynucleotide. In this case, it may not be necessary to use Daughter Vector Fragment in the One Pot Reaction, but untreated Daughter Vector may be used. IN this case, cells that have been transformed with the Daughter Vector may be selected against by growing the transformed cells under conditions that are restrictive for the counter-selectable marker. Thus only host cells carrying Daughter Vector from which the Stuffer Fragment has been excised and into which an Insert Fragment has been ligated, will survive. Useful counter-selectable markers include sacB, rpsL, tetAR, pheS, thyA, lacY, gata-1, ccdB, kid or barnase. A Daughter Vector counter-selectable marker may be the same or different from a Mother Polynucleotide counter-selectable marker.

Under appropriate growth conditions, a counterselectable gene promotes the death of the microorganism harboring it, hence allowing transformants that have retained the counterselectable marker to be eliminated in the presence of the counterselective compound. Non-limiting examples of counter-selectable markers include rpsL genes that make cells sensitive to streptomycin; pheS genes that encodes the α subunits of Phe-tRNA synthetase, which renders bacteria sensitive to the phenylalanine analog p-chlorophenylalanine; sacB genes that encodes levansucrase, an enzyme that converts sucrose to levans which are harmful to bacteria; thyA genes which encodes thymidilate synthetase, which confers sensitivity to trimethoprim and related compounds; lacy genes that encode lactose permease, which renders bacteria sensitive to t-o-nitrophenyl-b-D-galactopyranoside; gata-1 genes that encodes zinc finger DNA-binding proteins which inhibit initiation of bacterial replication; and ccdB genes which encode a cell-killing protein which is a potent poison of bacterial gyrase.

Another aspect of this disclosure is compositions containing mixtures of Mother Polynucleotide, Daughter Vector or Daughter Vector Fragment, typeIIs restriction endonucleases and ligase. Preferred mixtures comprise Daughter Vector or Daughter Vector Fragment concentrations between 0.01 pM and 1 µM, more preferred mixtures contain Daughter Vector or Daughter Vector Fragment concentrations between 0.1 pM and 100 nM, more preferred mixtures contain Daughter Vector or Daughter Vector Fragment concentrations between 1 pM and 10 nM. Preferred mixtures comprise Mother Polynucleotide concentrations between 0.01 pM and 1 µM, more preferred mixtures contain Mother Polynucleotide concentrations between 0.1 pM and 100 nM, more preferred mixtures contain Mother Polynucleotide concentrations between 1 pM and 10 nM. Preferred mixtures comprise restriction endonuclease concentrations between 0.01 U/ul and 100 U/ul, more preferred mixtures contain endonuclease concentrations between 0.1 U/ul and 10 U/ul, more preferred mixtures contain endonuclease concentrations between 0.1 U/ul and 1 U/ul. Preferred mixtures comprise DNA ligase concentrations between 1 U/ul and 400 U/ul, more preferred mixtures contain DNA ligase concentrations between 1 U/ul and 40 U/ul, more preferred mixtures contain DNA ligase concentrations between 1 U/ul and 4 U/ul.

In a particular embodiment, the restriction endonuclease(s) can be combined with the DNA ligase(s) in a single tube prior to use in a One Pot Reaction. This allows an optimal ratio of the two enzymes to be added easily. It also prevents inadvertent omission of one of the enzymes from a reaction. In another particular embodiment, the buffer(s), restriction endonuclease(s) and the ligase(s) are can be pre-mixed and retain each individual component's desired function. Providing these two reagents in an easy-to-use form is advantageous to the user, and a preferred embodiment of the disclosure.

5.3.2 Daughter Vector Compositions

TypeIIs restriction endonucleases recognize asymmetric DNA sequences and cleave both DNA strands at fixed positions, typically several base pairs away from the recognition sites. This property makes typeIIs restriction endonucleases particularly useful for assembling DNA fragments, where fragments with matching type IIs-generated ends are annealed and ligated, leaving an assembled DNA product without restriction recognition sequence scars at the ligation junctions. Type IIs restriction endonucleases that recognize non-palindromic sequences of 5, 6 or 7 base pairs, are found at an average frequency of one in 512, 2048 or 8192 base pairs respectively. It is therefore, relatively easy to identify typeIIs restriction endonucleases that do not cut inside a typical gene-sized DNA fragment.

A Daughter Vector can be constructed to permit cloning using typeIIs restriction endonucleases and ligase by incorporating a Stuffer flanked by typeIIs restriction sites into a vector comprising a selectable marker. It is advantageous to place typeIIs restriction sites in a Daughter Vector such that cleavage of the Daughter Vector with one or more typeIIs restriction enzymes yields a Daughter Vector Fragment with ends that are not compatible with each other. This design imposes directionality upon the ligation of one or more Insert Fragments with the Daughter Vector Fragment, it also prevents the Daughter Vector Fragment from ligating with itself. In preferred embodiments the Daughter Vector Fragment ends are also not pseudo-compatible with each other; that is they do not anneal with each other by forming at least one non-standard Watson-Crick base pair (i.e., T or U with G) in a way that can be joined by a DNA ligase with reasonable efficiency.

Any vector can be converted to a Daughter Vector capable of supporting a one-step typeIIs restriction cloning. This can be done by designing and synthesizing a nucleic acid sequence for a cloning cassette as described herein, then cloning that cassette into the vector to be converted. In some embodiments the cloning cassette comprises a counter-selectable marker flanked by typeIIs restriction sites, wherein the typeIIs restriction sites are not present in the other parts of the vector to be converted. Such design and synthesis methods are well known in the art. The conversion of vectors to allow 1-step type IIs cloning is expressly contemplated.

Of course, one of skill in the art will recognize that alternative methods can be used to construct a vector suitable for use in the methods, compositions, and kits described herein. For example, oligonucleotides containing appropriate Type IIs recognition sequences can be synthesized and introduced into the vector using standard techniques, or a counter-selectable marker may be amplified by the polymerase chain reaction.

Because typeIIs restriction endonucleases cleave DNA outside their target sequences, they generate overhangs whose sequences are independent of their recognition sequence. Thus the Product Polynucleotide may contain a sequence derived from the Daughter Vector Fragment that is precisely juxtaposed with a sequence derived from the Insert Fragment. In some embodiments a Product Polynucleotide comprises an element that controls or influences expression that is derived from one of the fragments, placed precisely in relation to an element to be expressed that is derived from the other fragment. Elements controlling or influencing expression may include a transcriptional promoter or an enhancer or a terminator, an element that binds to a regulatory protein such as an activator or repressor of transcription, or an element that modulates the efficiency of initiation of translation such as a ribosome binding site or a Kozak consensus sequence or an internal ribosome entry site (IRES). The activity of expression-regulating elements may be specific to a certain host or group of hosts, for example specific to bacterial hosts or mammalian hosts or insect hosts or plant hosts or yeast hosts.

In some embodiments a Product Polynucleotide comprises two elements encoding polypeptides, one derived from the Insert Fragment and the other derived from the Daughter Vector Fragment, wherein the two elements are juxtaposed such that they encode a single contiguous polypeptide without any extraneous sequence derived from residual restriction recognition sequences. In some embodiments the contiguous polypeptide comprises a sequence that is partly encoded by a the Daughter Vector Fragment, and that confers a property affecting solubility, stability, proper folding, improved yields, localization, color or fluorescence of a protein, or affinity of a protein for a substrate, or a characteristic that facilitates purification or tracking of a protein in a cell.

In some embodiments, the Daughter Vector comprises sequences encoding fusion tags, wherein the fusion tags are fused either to the N or C-terminus of an open reading frame (ORF) encoded in the Product Polynucleotide by sequences derived from the Insert Fragment. Fusion tags can facilitate detection and/or purification of a protein. For example, use of poly-histidine tags are well known in the art and are used for detection of expression using antibodies raised against poly-histidine, they can also facilitate affinity purification using a $Ni^{2+}$ or $Co^{2+}$ affinity columns. Poly-histidine tags have an affinity for nickel or cobalt ions which are coordinate covalently bonded with a chelator for purposes of solid medium entrapment. In some embodiments the Daughter Vector comprises a sequence that encodes a polyhistidine tag comprising from about two to ten contiguous histidine residues (e.g., two, three, four, five, six, seven, eight, nine or ten contiguous histidine residues). The tag can also be a peptide tag which binds nickel ions, as well as other metal ions (e.g., copper ion), and can be used for metal chelate affinity chromatography. Examples of such tags include peptides having the formula: $R_1$-(His-X)$_n$-$R_2$, wherein (His-X) represents a metal chelating peptide and n is a number between two through ten (e.g., two, three, four, five, six, seven, eight, nine or ten), and X is an amino acid selected from the group consisting of alanine, arginine, aspartic acid, asparagines, cysteine, glutamic acid, glutamine, glycine, histidine, isoleucine, leucine, lysine, methionine, phenylalanine, proline, serine, threonine, tryptophan, tyrosine, and valine. Further $R_2$ may be a polypeptide that is covalently linked to the metal chelating peptide and $R_1$ may be either a hydrogen or one or more (e.g., one, two, three, four, five, six, seven, eight, nine, ten, twenty, thirty, fifty, sixty or more) amino acid residues. In addition $R_1$ may be a polypeptide which is covalently linked to the metal chelating peptide and $R_2$ may be either a hydrogen or one or more (e.g., one, two, three, four, five, six, seven, eight, nine, ten, twenty, thirty, fifty, sixty or more) amino acid residues. Tags of this nature are described in U.S. Pat. No. 5,594,115.

In some embodiments, the Daughter Vector comprises sequences encoding other fusion tags including but not limited to glutathione-S-transferase (GST), maltose binding protein (MBP), FLAG tag, V5 epitope, a c-myc epitope, a hemagglutinin A epitope, Streptavidin II, T7 tag, S-tag, DHFR tag, chitin binding domain, calmodulin binding domain, cellulose biding domain, T7 gene 10 tag, NusA tag, thioredoxin, SUMO, ubiquitin tags, SNAP tag, MCP tag, ACP tag. In some embodiments, the Daughter Vector comprises sequences encoding a peptide sequence that serves as the recognition and/or cleavage site for a sequence specific protease. Such sequences include but are not limited to TEV protease, AcTEV, ProTEV, HRV3C protease, thrombin, Factor Xa, Prescission protease, genenase I, Enterokinase (enteropeptidase), Furin, Proteinase K, modified Trypsin, Endoproteinase GluC, Endoproteinase AspN, SUMO proteases, Immobilized subtilisin BPN, Tagzyme (DAPase).

In certain embodiments, a Daughter Vector encodes a cell compartmentalization domain, such as a plasma membrane localization domain, a nuclear localization signal, a mitochondrial membrane localization signal, an endoplasmic reticulum localization signal, or a protein transduction domain such as the human immunodeficiency virus TAT protein transduction domain, which can facilitate translocation of a peptide linked thereto into a cell (see Schwarze et al., Science 285: 1569-1572, 1999; Derossi et al., J. Biol. Chem. 271:18188, 1996; Hancock et al., EMBO J. 10:4033-4039, 1991; Buss et al., Mol. Cell. Biol. 8:3960-3963, 1988; U.S. Pat. No. 5,776,689). Such a domain can be useful to target a fusion polypeptide compressing the domain and a polypeptide encoded by an Insert Fragment, to a particular compartment in the cell, or for secretion from or entry into a cell.

In some embodiments the contiguous polypeptide comprises a 2A peptide or a CHYSEL sequence which allow the expression of more than one polypeptide to be driven by a single promoter sequence in eukaryotic cells. A 2A peptide sequence or a CHYSEL site causes a eukaryotic ribosome to release the growing polypeptide chain, but continue translating, thereby giving rise to two separate polypeptides from a single translating ribosome. An expression cassette using a 2A peptide or a CHYSEL coupling element comprises a promoter, a nucleic acid sequence encoding a first polypeptide, a nucleic acid sequence that encodes a 2A peptide or a CHYSEL peptide and a second nucleic acid sequence encoding a second polypeptide. In some embodiments the first or second polypeptide may comprise a selectable protein including any chromogenic or fluorescent protein. One functional order of elements is promoter then selectable protein then 2A peptide or CHYSEL peptide then open reading frame of interest. Another functional order of elements is promoter then open reading frame of interest then 2A peptide or CHYSEL peptide then selectable protein.

In certain embodiments, the Daughter Vector is a cloning vector or an expression vector. In some embodiments the Daughter Vector comprises a eukaryotic origin of replication. In some embodiments, the Daughter Vector is a plasmid vector, a cosmid vector, an artificial chromosome (for example a bacterial artificial chromosome, a yeast artificial chromosome or a mammalian artificial chromosome), a viral vector such as a bacteriophage, baculovirus, retrovirus, lentivirus, adenovirus, Vaccinia virus, semliki forest virus or adeno-associated virus vector, all of which are well known and can be purchased from commercial sources (Promega, Madison Wis.; Stratagene, La Jolla Calif.; GIBCO/BRL. Gaithesburg Md.). Viral expression vectors can be particularly useful where a method is practiced for the purpose of generating a recombinant nucleic acid molecule that is to be introduced into a cell, particularly a cell in a subject. Viral vectors provide the advantage that they can infect host cells with relatively high efficiency and can infect specific cell types or can be modified to infect particular cells in a host.

In some embodiments the Daughter Vector is a viral vector developed for use in a particular host system; for example a baculovirus vector which infects insect cells; a retroviral vector, a lentiviral vector based on the human immunodeficiency virus (HIV), an adenovirus vector, an adeno-associated virus (AAV) vector, a herpesvirus vector, or a Vaccinia virus vector which infects mammalian cells (Miller and Rosman, Biotechniques 7:980-990, 1992; Anderson et al., Nature 392:25-30 Suppl., 1998; Verma and Somia, Nature 389:239-242, 1997; Wilson, New Engl. J. Med. 334:1185-1187, 1996, each of which is incorporated herein by reference). For example, a viral vector based on an HIV can be used to infect T cells, a viral vector based on an adenovirus can be used, for example, to infect respiratory epithelial cells, and a viral vector based on herpesvirus can be used to infect neuronal cells. Other vectors, such as AAV vectors can have a greater host cell range and, therefore, can be used to infect various cell types, although viral or non-viral vectors can also be modified with specific receptors or ligands to alter target specificity through receptor mediated events.

In some embodiments the Daughter Vector comprises a transcriptional expression control element that is a promoter from a virus including cytomegalovirus, Miloney leukemia virus and herpes virus; or a promoter from a gene encoding metallothionein, skeletal actin, phosphoenolpyruvate carboxylase, phosphoglycerate, dihydrofolate reductase, or thymidine kinase; or a promoter from a viral long terminal repeat (LTR) such as Rous sarcoma virus LTR; or a constitutive enhancer such as an immunoglobin enhancer; or an inducible enhancer such as an SV40 enhancer. A metallothionein promoter is a constitutively active promoter that can be induced to a higher level of expression upon exposure to a metal ion such as copper, nickel or cadmium ion. A tetracycline (tet) inducible promoter is an example of a promoter that is induced upon exposure to tetracycline, or a tetracycline analog, but is otherwise inactive.

In some embodiments the Daughter Vector comprises a tissue specific transcriptional expression control element. Tissue specific promoters are active in specific type of cells or tissues such as B cells, monocytic cells, leukocytes, macrophages, muscle, pancreatic acinar calls, endothelial cells, astrocytes and lung. For example, promoters B29 r in B cells, CD14 in monocytic cells, CD43 in leukocytes and platelets, CD45 in haematopoietic cells, CD68 in macrophages, Desmin in muscle, Elastase-1r in pancreatic acinar cells, Endoglin in endothelial cells, Fibronectin in differentiating and healing tissue, Flt-1 in endothelial cells, GFAP in astrocytes, GPIIb in megakaryocytes, ICAM-2 in endothelial cells, INF-β and WASP in hematopoietic cells, Mb in muscle, NphsI in podocytes, OG-2 in osteoblasts and odonblasts, SP-B in lung, SYN1 in neurons. In one example, a muscle cell specific expression control element, such that expression of an encoded product is restricted to the muscle cells in an individual, or to muscle cells in a mixed population of cells in culture, for example, an organ culture. Muscle cell specific expression control elements including, for example, the muscle creatine kinase promoter (Sternberg et al., Mol. Cell. Biol. 8:2896-2909, 1988) and the myosin light chain enhancer/promoter (Donoghue et al., Proc. Natl. Acad. Sci., USA 88:5847-5851, 1991) are well known in the art. Other tissue specific promoters, as well as expression control elements only expressed during particular developmental stages of a cell or organism are well known in the art.

In certain embodiments, a Daughter Vector further comprises woodchuck hepatitis post-transcriptional regulatory element (WPRE) or a scaffold attachment region (SAR).

In certain embodiments, a Daughter Vector further comprises a recombination protein, for example a recombinase, an integrase or a transposase including a piggyBac transposase and two or more site specific integration recognition sites to facilitate integration of an expression cassette into the genome of an expression host. In certain embodiments, these integration-facilitating sequences include a TTAA-target site specific insertion element. In certain embodiments the integration-facilitating sequences are recognized by an integrase or a transposase, in certain embodiments said integrase is a piggyBac integrase. In certain embodiments said Daughter Vector further comprises a gene encoding said integrase. In certain embodiments, an expression vector further comprises Lentiviral LTR (long terminal repeats) to facilitate integration of an expression cassette into the genome of an expression host.

In some embodiments, the Daughter vector sizes can range from 1 kb to 20 kb or more (for e.g. 1 or 2 or 3 or 4 or 5 or 6 or 7 or 8 or 9 or 10 or 11 or 12 or 13 or 14 or 15 or 16 or 17 or 18 or 19 or 20 or more kb). Since the Daughter vectors contain a toxic gene such as ccdB as described herein, there is no need for gel purification and therefore the Daughter vector is not limited in size.

In some embodiments, the Insert fragments can range from 25 base pairs to 10 kb or more (for e.g. 25 or 30 or 40 or 50 or 60 or 70 or 80 or 1000 or 2000 or 3000 4000 or 5000 or 6000 or 7000 or 8000 or 9000 or 10000 or 11000 or 12000 or 13000 or 14000 or more base pairs, or any combination thereof). The use of typeIIs recognition sequences as described herein allow non-compatible overhangs to be generated at each end of the insert fragment thereby preventing the insert fragment from looping back on itself and self-ligating. This allows for a range of insert sizes without the possibility for self-ligation. Very large insert fragment sizes are also possible since the typeIIs restriction enzyme SapI as described herein has a 7 base pair recognition sequence that occurs at an average frequency of 1 in 8192 base pairs, which means that the likelihood of the site occurring within the insert sequence is very low. Since the method described herein allows for easy transfer of insert fragment from mother polynucleotide to daughter vector, the insert fragment needs to be cloned into the mother polynucleotide only once, therefore avoiding mutagenic events introduced by use of polymerases or recombinases, allowing for a greater range of insert fragment sizes.

Expression control and other elements useful in the vectors can be obtained in various ways. In particular, many of the elements are included in commercially available vectors and can be isolated there from and can be modified as disclosed herein. In addition, the sequences of or encoding the elements useful herein generally are well known and disclosed in publications. In many cases, the elements, for example, transcriptional and translational expression control elements, as well as compartmentalization domains, are relatively short sequences, and, therefore, are amenable to chemical synthesis of the element or a nucleotide sequence encoding the element.

A vector useful in the methods described herein also can encode a ribonucleic acid (RNA) molecule, which can function, for example, as a riboprobe, an antisense nucleic acid molecule, a ribozyme, or a triplexing nucleic acid molecule, or can be used in an in vitro translation reaction, and the second nucleic acid molecule can encode an expression control element useful for expressing an RNA from the first nucleic acid molecule. For example, where it is desired to produce a large amount of RNA, a second nucleic acid molecule component for performing a method as described herein can comprise an RNA polymerase promoter such as T7, T5, T3 or SP6 RNA polymerase promoter. Where the RNA molecule is to be expressed in a cell, for example, an antisense molecule to be expressed in a mammalian cell, the second (or other) nucleic acid molecule can include a promoter that is active in a mammalian cell, particularly a tissue specific promoter, which is active only in a target cell. Furthermore, where the RNA molecule is to be translated, for example, in a coupled in vitro transcription/translation reaction, the first nucleic acid molecule or second (or other) nucleic acid molecule can contain appropriate translational expression control elements.

In many of the embodiments described herein, the Daughter Vectors can contain an origin of replication. However, it should be understood that the methods and compositions can work with vectors that do not comprise an origin of replication, e.g., vectors that integrate into the genome of a host following appropriate introduction into the host. Any such vector known to one skilled in the art without limitation can be used in the methods, compositions and kits.

Other embodiments include DNA and vectors useful in the methods of the present disclosure. In particular, Mother Polynucleotide molecules are provided, wherein one Mother Polynucleotide embodiment comprises a first DNA segment and a second DNA segment, the first or second segment comprising a selectable marker. A second Mother Polynucleotide embodiment comprises a first DNA segment and a second DNA segment, the first or second DNA segment comprising a toxic gene. A third Mother Polynucleotide embodiment comprises a first DNA segment and a second DNA segment, the first or second DNA segment comprising an inactive fragment of at least one selectable marker, wherein the inactive fragment of the selectable marker is capable of reconstituting a functional selectable marker when combined into a Product Polynucleotide with another inactive fragment of at least one selectable marker derived from the Daughter Vector.

5.3.3 Compatibility of one Mother Polynucleotide with Multiple Daughter Vectors

Sub-cloning of DNA segments is performed as a daily routine in many research labs. It is frequently performed in order to move a first polynucleotide sequence from a first vector into a second vector, where the second vector performs a function that is not performed by the first. Differences between the two vectors may include differences in selectable markers or differences in replicative sequences. They may also include differences in vector sequence elements that may directly interact with the first polynucleotide, for example by affecting expression of the first polynucleotide, or by encoding polypeptides that interact with or are joined to polypeptides encoded by the first polynucleotide.

When a Mother Polynucleotide and a Daughter Vector are cleaved by their respective typeIIs restriction endonucleases, the resulting overhangs are not contained within the typeIIs recognition sequences so in principle any set of compatible overhangs may be selected. Thus it is possible to completely control the sequence of the Product Polynucleotide, without being forced to incorporate restriction sites or recombination sequences. This is an advantage of the present disclosure. In preferred embodiments an Insert Fragment derived from a Mother Polynucleotide may be ligated with a plurality of different Daughter Vector Fragments, all of which share the same pair of overhangs. This allows a plurality of sequence contexts to be explored in parallel. For example in embodiments where the Insert Fragment comprises a polynucleotide that encodes a polypeptide, it may be advantageous to express the encoded polypeptide under a plurality of conditions, for example under the control of one or more promoter, with one or more C-terminal fusion or one or more N-terminal fusion; under control of one or more ribosome binding sites; with one or more IRES or 2A peptide elements for bicistronic expression; under control of one or more transcription control elements that are host specific to determine conditions that yield the most preferred levels of expression, or the most preferred polypeptide solubility, or the most preferred polypeptide activity.

In preferred embodiments therefore, groups of Daughter Vectors are designed so that the overhangs of a single Insert Fragment are compatible with the ends of any Daughter Vector Fragment selected from the group. In preferred embodiments the overhang comprises a sequence that can perform a specific function, in some embodiments the overhang comprises the sequence of a codon, in some embodiments the codon encodes a methionine or a glycine or a stop codon. In some embodiments an overhang comprises the sequence 5'-ATG-3', or 5'-CAT-3', or 5'-GGT-3', or 5'-ACC-3', or 5'-TAA-3', or 5'-TTA-3', or 5'-AATG-3', or 5'-CATT-3' or 5'-TAAA-3', or 5'-ATTT-3', or 5'-CCCC-3', or 5'-GGGG-3', or 5'-TTTT-3', or 5'-AAAA-3'.

Preferred embodiments comprise a plurality of Daughter Vectors that are all useable with any open reading frame. Open reading frames all begin with a methionine codon (which is 5'-ATG-3') and end with a stop codon (5'-TAG-3', or 5'-TAA-3', or 5'-TGA-3'). Thus one preferred embodiment comprises a plurality of Daughter Vectors that can be cut to produce Daughter Vector Fragments that are compatible with any Insert Fragment that has an overhang comprising 5'-ATG-3' at one end, and 5'-TAG-3', or 5'-TAA-3', or 5'-TGA-3' at the other end. Another preferred embodiment comprises a plurality of Daughter Vectors that can be cut to produce Daughter Vector Fragments that have overhangs comprising 5'-ATG-3' at one end, and 5'-GGN-3', or 5'-GCN-3' at the other end and are ligatable with any Insert Fragment that has compatible overhangs. The Daughter Vector Fragments comprise a transcriptional promoter which becomes operably linked to the ORF encoded in the Insert Fragment when the two molecules are joined in the One Pot Reaction to form a Product Polynucleotide. The Product Polynucleotide is transformed into an Expression Host, where transcription from the promoter causes the ORF encoded on the Insert Fragment to be expressed. In a preferred embodiment the plurality of Daughter Vectors differ from one another in sequences that control or influence expression, for example a promoter, a terminator, a ribosome biding site, a sequence that affects the initiation of translation, an enhancer, an element that affects the copy number of the Daughter Vector in the Expression Host, an element that affects the site of genomic integration in an expression host. Thus an ORF encoded in a Mother Polynucleotide may be easily joined with a plurality of different Daughter Vector Fragments to obtain a construct producing desired expression properties. In some embodiments a Mother Polynucleotide is joined with each of a plurality of Daughter Vector Fragments in a plurality of One Pot Reactions, each comprising a single Mother Polynucleotide and a single Daughter Vector Fragment. In some embodiments a Mother Polynucleotide is joined with each of a plurality of Daughter Vector Fragments in a One Pot Reaction comprising a single Mother Polynucleotide and a plurality of Daughter Vector Fragments. In some embodiments, a plurality of Mother Polynucleotides are each joined with a respective Daughter Vector Fragment in a plurality of Daughter Vector Fragments in a One Pot Reaction comprising a plurality of Mother Polynucleotides and a plurality of Daughter Vector Fragments.

In other preferred embodiments, a plurality of Daughter Vector Fragments comprise a transcriptional promoter and a sequence encoding a fusion tag, which is a polypeptide that confers a property affecting solubility, stability, proper folding, improved yields, localization, color or fluorescence of a protein, or affinity of a protein for a substrate, or a characteristic that facilitates purification or tracking of a protein in a cell. When an Insert Fragment encoding an ORF is joined with such a Daughter Vector Fragment in the One Pot Reaction to form a Product Polynucleotide, the Product Polynucleotide comprises a sequence encoding the fusion tag joined to the ORF encoded in the Insert Fragment.

In a preferred embodiment the plurality of Daughter Vectors differ from one another in sequences that control or influence expression, or in the sequence and properties of the encoded fusion tag (which may be added to the C-terminus or the N-terminus of the polypeptide encoded in the Inset Fragment. Thus an ORF encoded in a Mother Polynucleotide may be easily joined with a plurality of different Daughter Vector Fragments to obtain a construct producing a polypeptide fusion with desired properties. In some embodiments a Mother Polynucleotide is joined with each of a plurality of Daughter Vector Fragments in a plurality of One Pot Reactions, each comprising a single Mother Polynucleotide and a single Daughter Vector Fragment. In some embodiments a Mother Polynucleotide is joined with each of a plurality of Daughter Vector Fragments in a One Pot Reaction comprising a single Mother Polynucleotide and a plurality of Daughter Vector Fragments. In some embodiments, a plurality of Mother Polynucleotides are each joined with a respective Daughter Vector Fragment in a plurality of Daughter Vector Fragments in a One Pot Reaction comprising a plurality of Mother Polynucleotides and a plurality of Daughter Vector Fragments.

When a Product Polynucleotide comprises a sequence encoding a polypeptide that originates in part from a Daughter Vector Fragment and in part from an Insert Fragment, if the Daughter Vector Fragment contributes the C-terminus of the encoded polypeptide, then the sequence from the Insert Fragment cannot end with a stop codon, as that would prevent a C-terminal fusion from the Daughter Vector Fragment. In this case it is advantageous instead to have open reading frames end with a codon that encodes an amino acid that is least likely to disrupt structure, and most likely to participate in a productive join to the C-terminally fused peptide or polypeptide. In preferred embodiments the open reading frame encoded in an Insert Fragment or a Mother Polynucleotide ends with a glycine codon or an alanine codon. In preferred embodiments the Mother Polynucleotide is cleaved in a One Pot Reaction to produce an overhang comprising 5'-ACC-3', or 5'-TCC-3', or 5'-GCC-3', or 5'-CCC-3', or 5'-TGC-3', or 5'-AGC-3', or 5'-CGC-3', or 5'-GGC-3' that is compatible with one end of a Daughter Vector Fragment.

In a most preferred embodiment, an Insert Fragment comprising a sequence that encodes a polypeptide can be subcloned into a plurality of Daughter Vector Fragments, wherein the Daughter Vector Fragments may differ from one another in sequences that control or influence expression, or they may differ from one another in sequences that encode a fusion tag, or both. Such a system has the advantage that a Mother Polynucleotide need be prepared and sequenced only once, and then it can be transferred simply and easily with the fidelity of restriction digestion and ligation (which is less mutagenic than assembly techniques that require in vitro DNA polymerases), but without the residual sequence element "scars" that result from recombinase action. An example of such a preferred embodiment is a plurality of Daughter Vectors which can be cleaved by a typeIIs enzyme to produce an overhang comprising 5'-CAT-3' at one end at one end and either 5'-GGT-3', or 5'-GGA-3', or 5'-GGC-3', or 5'-GGG-3', or 5'-GCT-3', or 5'-GCA-3', or 5'-GCC-3', or 5'-GCG-3' at the other. In preferred embodiments each Daughter Vector Fragment in the plurality of Daughter Vector Fragments has the same two overhangs.

As described herein, the specialized vectors used for subcloning DNA segments are functionally diverse. These include but are not limited to: vectors for expressing genes in various organisms; for regulating gene expression; for providing tags to modify polypeptide properties such as solubility, localization, affinity for a substrate, color, fluorescence, characteristics that facilitate protein purification and characteristics that facilitate tracking of proteins in cells; for modifying the cloned DNA segment (e.g., generating deletions); for the synthesis of probes (e.g., riboprobes); for the preparation of templates for DNA sequencing; for the identification of protein coding regions; for the fusion of various protein-coding regions; for expressing one or more enzymes to catalyze a reaction and for providing large amounts of the DNA of interest. It is common that a particular investigation will involve subcloning the DNA segment of interest into several different specialized vectors. By designing specialized acceptor or daughter vectors with appropriate typeIIs restriction sites flanking the cloning site, any nucleotide fragment encoding an open reading frame of interest can be quickly and efficiently cloned into one or multiple daughter expression vectors (FIGS. 6A-6B). The nucleotide fragment can either be cloned into a mother polynucleotide as described herein or can be amplified with flanking typeIIs recognition sequences using PCR. PCR products can be directly cloned into any of the specialized daughter vectors.

5.3.4 Multi-Part Assembly

In one embodiment, the recombinant nucleic acid molecules encode chimeric polypeptides for performing a two-hybrid assay. In such a method, the vector encodes a polypeptide, or a relevant domain thereof, that is suspected of having or being examined for the ability to interact specifically with one or more (e.g., 1, or 2, or 3, or 4, or 5, or 6, or 7, or 8, or 9, or 10, or 11, or 12, or 13, or 14, or 15, or more) other polypeptides. The insert nucleic acid, to which the vector is to be linked as described herein, can encode a transcription activation domain or a DNA binding domain. For example, a first nucleic acid molecule to be directionally linked is modified, for example to contain a 5' overhang on a first end and a typeIIs recognition site, or cleavage product thereof, at or near the first end. A second nucleic acid molecule to be linked contains, or is modified to contain, a 5' sequence complementary to the 5' overhang at the first end of the first nucleic acid molecule. Upon contact of the overhangs of the first and second nucleic acid molecules generated by cleavage with typeIIs enzymes and in the presence of T4 ligase, the directionally linked nucleic acid molecules encodes a first hybrid useful for performing a two hybrid assay (see, for example, Fields and Song, Nature 340:245-246, 1989; U.S. Pat. No. 5,283,173; Fearon et al., Proc. Natl. Acad. Sci., USA 89:7958-7962, 1992; Chien et al., Proc. Natl. Acad. Sci., USA 88:9578-9582, 1991; Young, Biol. Reprod. 58:302-311, 1998). Similar methods are used to generate the second hybrid protein, which can comprise a plurality of polypeptides to be tested for the ability to interact with the polypeptide, or domain thereof, of the first hybrid protein. Such methods similarly can be used to construct directionally linked nucleic acid molecules encoding fusion protein useful for a modified form of a two hybrid assay such as the reverse two hybrid assay (Leanna and Hannink, Nucl. Acids Res. 24:3341-3347, 1996), the repressed transactivator system (U.S. Pat. No. 5,885,779) and the protein recruitment system (U.S. Pat. No. 5,776,689).

The vectors can be used to construct, for example, a DNA library. In such embodiments, the insert can be a plurality of nucleic acid molecules, for example a cDNA library, a combinatorial library of nucleic acid molecules, or a population of variegated nucleic acid molecules. As such, the methods are particularly useful for generating recombinant polynucleotides encoding chimeric polypeptides for performing a high throughput two hybrid assay for identifying protein-protein interactions that occur among populations of polypeptides (see U.S. Pat. No. 6,057,101 and 6,083,693). In such a method, each of the hybrid proteins of the two hybrid assay is generated using a different one of two populations (pluralities) of nucleic acid molecules encoding polypeptides, each plurality having a complexity of a few related but different nucleic acid molecules to tens of thousands of such molecules. By, for example, using a PCR primer pair to amplify each nucleic acid molecule in a plurality, directionally linked recombinant polynucleotides encoding a population of chimeric prey polypeptides can be readily generated. Such populations are generated by contacting the amplified pluralities of nucleic acid molecules, each of which comprises an appropriate end with typeIIs recognition sites and a nucleic acid molecule which contains a suitable typeIIs site at or near its ends and encodes a transcription activation domain or a DNA binding domain.

5.3.5 Kits for One Step Cloning Using typeIIs Restriction Endonuclease

Further provided are kits for one-step typeIIs cloning. In certain embodiments, the kit comprises a vector that will support one step type IIs cloning, a typeIIs restriction enzyme and T4 DNA ligase mix. In certain embodiments, the kits comprise one or more reagents (e.g., 1, or 2, or 3, or 4, or 5, or 6, or 7, or 8, or 9, or 10, or 11, or 12, or 13, or 14, or 15, or more) useful for performing a method as described herein. In one embodiment, the kit comprises a nucleic acid, e.g., a vector, suitable for use in a method described herein. One or more typeIIs restriction endonucleases, can also be part of the kit. The nucleic acid in the kit can, but need not be a vector and can contain one or more (e.g., 1, or 2, or 3, or 4, or 5, or 6, or 7, or 8, or 9, or 10, or 11, or 12, or 13, or 14, or 15, or more) expression control elements. In certain embodiments, the kit comprises instructions for using kit components.

A kit can include a plurality of second nucleic acid molecules, wherein each nucleic acid molecule in the plurality has a first end, wherein the first end includes a 5' nucleotide sequence that is complementary to a 5' overhang of the first nucleic acid molecule, e.g., the vector. The second nucleic acid molecules in the plurality can encode a plurality of transcriptional regulatory elements, translational regulatory elements, or a combination thereof, or can encode a plurality of peptides, such as peptide tags, cell compartmentalization domains and protease cleavage sites.

A nucleic acid molecule component of a kit can be, for example, a circularized or linearized vector such as a cloning vector or expression vector. If desired, such a kit can contain a plurality of nucleic acid molecules, each comprising a different expression control element or other element such as, but not limited to a sequence encoding tag or other detectable molecule or a cell compartmentalization domain. The different elements can be different types of a particular expression control element, for example, constitutive or inducible promoters or tissue specific promoters, or can be different types of elements including, for example, transcriptional and translational expression control elements and epitope tags. In addition, the plurality of nucleic acid molecules can have 5' overhanging sequences that are unique to a particular expression control element, or that are common to a plurality of related expression control elements, for example, to a plurality of different promoter elements. The 5' overhanging sequences of nucleic acid molecules can be designed such that one or more expression control elements contained on the nucleic acid molecule can be operatively directionally linked to provide a useful function, for example, an element comprising a Kozak sequence and an element comprising a translation start site can have complementary 5' overhangs such that the elements can be operatively linked as described herein.

Further provided are kits for linking nucleic acid molecules using methods described herein. Thus, kits may comprise one or more components for performing methods described herein. In particular embodiments, the kits may comprise one or more components selected from the group consisting of instructions for use of kits components, one or more buffers, one or more nucleic acid molecules (e.g., one or more nucleic acid molecules having a 5' overhang or a 3' overhang or a 5' overhang and a 3' overhang or two 5' overhangs or two 3' overhangs or more.), one or more typeIIs endonucleases, one or more ligase, one or more adapter linker for preparing molecules having a 5' overhang and/or a 3' overhang, and/or one or more containers in which to perform methods described herein. In certain embodiments, the kits comprise a buffer in which both a typeIIs restriction endonuclease and a DNA ligase are active.

6. EXAMPLES

The following examples are intended to illustrate the methods, compositions and kits disclosed herein and should not be construed as limiting in any way. Various equivalents will be apparent to one skilled in the art from the following examples; such equivalents are also contemplated to be part of the disclosure disclosed herein.

6.1 One-Step Cloning of Yellow Fluorescent Protein from Mother Polynucleotides to Daughter Vectors This experiment is shown schematically in FIG. 5. A gene for yellow fluorescent protein was synthesized and cloned into two mother polynucleotide constructs 107888 (SEQ ID NO: 1) and 107889 (SEQ ID NO: 2). The mother polynucleotides used had a pUC bacterial origin of replication, terminators, counter-selectable markers rpsL or pheS respectively and a gene conferring antibiotic resistance to the antibiotic ampicillin. The gene that encodes yellow fluorescent protein (SEQ ID NO: 5) was used as a DNA test insert for fragment exchange into acceptor or daughter vectors.

The daughter vectors used were vector constructs 107892 (SEQ ID NO: 3) with a T5 promoter, strong RBS and gene conferring antibiotic resistance to kanamycin; and construct 106730 (SEQ ID NO: 4) with a rhamnose inducible rhapBAD promoter, a medium copy origin of replication pBR and gene conferring resistance to kanamycin. The daughter vectors also contained a stuffer fragment flanked by type IIs restriction sites that contained a counter selectable maker ccdB. Concentrations of mother polynucleotides 107888 and 107889; and daughter vectors 107892 and 106730 were determined using Nanodrop.

The Daughter Vector Fragments from 107892 and 106730 were prepared as follows: 20 µg of uncut vector was digested in a total volume of 200 µl with 50 mM potassium acetate, 20 mM Tris-acetate, 10 mM magnesium acetate, 1 mM dithiothreitol, pH7.9 and 50 units of restriction enzyme SapI (from New England Biolabs). The reactions were incubated for 1 hr at 37° C. 25 units Calf Intestinal Phosphatase (CIP from New England Biolabs) was added to the reaction and incubated for 1 hour at 37° C. 40 µl of 6XLB was added to each reaction and run out in 4 wells for each construct with 60 µl/well of a 10-well preparative 1% Agarose/TBE gel. Gel was run at 80V for 50 minutes. Bands on gel were excised and gel purified using Qiaex II™ (from Qiagen) with 20 µl of beads as per Qiaex™ protocol, eluting each band in 60 µl warm Tris-EDTA buffer (TE). Concentration of linearized daughter vectors from gel excised bands was determined using Nanodrop and used in subsequent reactions for fragment exchange.

Subcloning of the gene that encodes yellow fluorescent protein from Mother Polynucleotides 107888 and 107889 to Daughter Vectors 107892 and 106730 was carried out. One reaction for each possible mother: daughter combinations; Mother 107888 X Daughter 107892; Mother 107888 X Daughter 106730; Mother 107889 X Daughter 107892; and Mother 107889 X Daughter 106730 were set up, including no enzyme or single enzyme controls for each of the mother: daughter combinations, a total of 16 reactions. 20 µl reactions were set up on ice containing 0.075 pmol Mother Polynucleotide, 0.025 pmol Daughter Vector Fragment with 50 mM potassium acetate, 20 mM Tris-acetate, 10 mM magnesium acetate, 1 mM dithiothreitol, pH7.9, 1 mM ATP (from New England Biolabs), and combinations of 2 units of SapI and/or 400 units of T4 DNA ligase (from New England Biolabs). Reactions were placed in a thermocycler and run under the following cycling conditions: 1 hour at 25° C., 20 minutes at 65° C., hold at 12° C., stop. 16 tubes containing 50 µl of NEB 10-beta competent cells (from New England Biolabs) were thawed on ice, 2.5 µl of each reaction was added and tubes heated for 30 seconds at 42° C. and immediately placed on ice for 2 minutes. 950 µl of SOC was added per tube, transferred to a culture tube and incubated with rolling for 1 hr at 37° C. 100 µl of each transformation was plated onto LB Agar plates with 30 µg/mL kanamycin alone or with kanamycin and 100 µg/mL streptomycin or YEG Agar plates with 30 µg/mL and 10 mM chloro-phenylalanine (phenylalanine analog).

The numbers of transformants for the different reactions are shown in Table 1.

TABLE 1

One-step cloning test.

| 1. Mother 107888 (rpsL) × Daughter 107892 | | | | |
| --- | --- | --- | --- | --- |
| Plate | 1 (No enzyme) | 2 (SapI only) | 3 (Lig only) | 4 (SapI + Lig) |
| LB/Kan | 0 | 4 White | 2 White | >1000 Yellow |
| LB/Kan/Str | 0 | 0 | 2 White | >1000 Yellow |

| 2. Mother 107888 (rpsL) × Daughter 106730 | | | | |
| --- | --- | --- | --- | --- |
| Plate | 5 (No enzyme) | 6 (SapI only) | 7 (Lig only) | 8 (SapI + Lig) |
| LB/Kan | 0 | 0 | 0 | >1000 |
| LB/Kan/Str | 4 | 0 | 1 | >1000 |

| 3. Mother 107889(pheS) × Daughter 107892 | | | | |
| --- | --- | --- | --- | --- |
| Plate | 9 (No enzyme) | 10 (SapI only) | 11 (Lig only) | 12 (SapI + Lig) |
| LB/Kan | 1 White | 7 White | 0 | >1000 Yellow |
| YEG/Kan | 0 | 5 White | 0 | >1000 White* |

| 4. Mother 107889 (pheS) × Daughter 106730 | | | | |
| --- | --- | --- | --- | --- |
| Plate | 13 (No enzyme) | 14 (SapI only) | 15 (Lig only) | 16 (SapI + Lig) |
| LB/Kan | 1 White | 1 White | 2 White | >1000 White |
| YEG/Kan | 0 | 2 White | 2 White | >1000 White |

*White on YEG due to glucose suppressing T5 promoter

Only reactions 4, 8, 12 and 16 with both SapI and T4 Ligase resulted in a significantly higher number of transformants compared to reactions with no enzyme or with either SapI or T4 ligase only. Although transformants were observed on plates with a single selection antibiotic as well as plates with antibiotic selection and counter selection streptomycin or the phenylalanine analog, background is lower with a dual selection.

These results show that incubation of Mother DNA, Daughter Vector Fragment DNA, type IIs restriction enzyme SapI and T4 DNA ligase in a single tube resulted in the subcloning and stable propagation of the yellow fluorescent protein-encoding fragment from the mother polynucleotide to the Daughter Vector. This method allows cloning and quick exchange of ORFs (open reading frame) to any expression or Daughter vectors designed to work in various host systems, thereby facilitating selection of best expression and host system for ORF of interest.

6.2 Time Course for Yellow Fluorescent Protein Cloning from Mother Polynucleotides to a Daughter Vector Mother polynucleotides (0.075 pmol of 107888 or 107889) encoding yellow fluorescent protein were incubated with 0.025 pmol Daughter Vector Fragment 107892 in 20 µl reactions containing 50 mM potassium acetate, 20 mM Tris-acetate, 10 mM magnesium acetate, 1 mM dithiothreitol, pH7.9, 1 mM ATP (from New England Biolabs), 2 units of SapI and 400 units of T4 DNA ligase.

Reactions were incubated for 1 hour at 25° C. and 20 minutes at 65° C. 2.5 µl of each reaction was added to 50 µl of NEB 10-beta competent cells (from New England Biolabs), heat shocked for 30 seconds at 42° C. and immediately placed on ice for 2 minutes. 950 µl of SOC was added per tube, transferred to a culture tube and incubated with rolling for 1 hr at 37° C. 100 µl of each transformation was plated onto LB Agar plates with 30 µg/mL kanamycin alone or with kanamycin and 100 µg/mL streptomycin or YEG Agar plates with 30 µg/mL and 10 mM chloro-phenylalanine (phenylalanine analog). 1:10 and 1:100 dilutions of the transformation culture were also plated. Colony counts are shown in Table 2.

These results show that incubation of Mother Polynucleotide DNA, Daughter Vector Fragment DNA, type IIs restriction enzyme SapI and T4 DNA ligase in a single tube resulted in the exchange and stable propagation of the yellow fluorescent protein fragment from the Mother polynucleotide to the Daughter vector in as little as 5 minutes at 25° C. (FIGS. 6A and 6B).

TABLE 2

Reaction time course.

| | CFU/1 µl plated LB + Kan | | CFU/1 µl plated LB + Kan + Step or YEG + Kan + chlorophe | |
|---|---|---|---|---|
| TIME | pMOTHER (rpsL) × pDAUGHTER (T5) | pMOTHER (pheS) × pDAUGHTER (T5) | pMOTHER (rpsL) × pDAUGHTER (T5) | pMOTHER (pheS) × pDAUGHTER (T5) |
| 5 minutes | 35 | 18 | 39 | 21 |
| 10 minutes | 87 | 67 | 115 | 68 |
| 20 minutes | 252 | 202 | 332 | 222 |
| 40 minutes | 423 | 381 | 432 | 421 |
| 60 minutes | 383 | 367 | 380 | 363 |

Reactions could also be carried out successfully for 5 minutes at room temperature (bench top) with no heat kill (data not shown). Background from carryover of mother polynucleotide is less than 10% and falls below 2% with counter selection. This method would allow quick cloning and exchange of ORFs (open reading frame) to any expression or daughter vectors designed to work in various host systems, thereby facilitating selection of optimal expression and host system for ORF of interest.

6.3 Variations of Concentrations of Parts and Enzymes

Mother Polynucleotide 107889 encoding yellow fluorescent protein was incubated with Daughter Vector Fragment 107892 in 20 µl reactions containing 50 mM potassium acetate, 20 mM Tris-acetate, 10 mM magnesium acetate, 1 mM dithiothreitol, pH7.9, 1 mM ATP (from New England Biolabs). The amount of each polynucleotide in a reaction is as shown in Table 3.

Each reaction contained 2 units of SapI and 400 units of T4 DNA ligase, except for the 1:5 dilution, which contained 0.4 units SapI and 80 units T4 DNA ligase.

Reactions were incubated for 1 hour at 25° C. and 20 minutes at 65° C. 2.5 µl of each reaction was added to 50 µl of NEB 10-beta competent cells (from New England Biolabs), heat shocked for 30 seconds at 42° C. and immediately placed on ice for 2 minutes. 950 µl of SOC was added per tube, transferred to a culture tube and incubated with rolling for 1 hr at 37° C. 100 µl of each transformation was plated onto LB Agar plates with 30 µg/mL kanamycin alone or with kanamycin and 100 µg/mL streptomycin or YEG Agar plates with 30 µg/mL and 10 mM chloro-phenylalanine (phenylalanine analog). 1:10 and 1:100 dilutions of the transformation culture were also plated.

TABLE 3

Varying reactant concentrations.

| Mother (ng/20 ul) | Daughter (ng/20 ul) | Enzyme Mix | CFU/1 ul plated |
|---|---|---|---|
| 25 | 25 | No dilution | 452 |
| 50 | 50 | No dilution | 397 |
| 100 | 100 | No dilution | 518 |
| 25 | 100 | No dilution | 528 |
| 100 | 25 | No dilution | 351 |
| 0 | 25 | 1:5 dilution | 20 |

Plates were incubated overnight at 37° C. and colonies counted. The results showed little difference in the number of transformants despite 4-fold variations in concentrations of Mother Polynucleotide and Daughter Vector. Reduction of enzyme concentrations by fivefold affected the total number of transformants; dropping by approximately 15-fold but does not kill the reaction.

In a separate experiment, we varied the Daughter Vector Fragment concentration while keeping the amount of Mother Polynucleotide constant. Mother polynucleotide 107889 was kept constant at 25 ng/20 ul reaction, Daughter Vector Fragment 107892 concentrations were varied as shown in Table 4.

Reactions were incubated for 1 hour at 25° C. and 20 minutes at 65° C. 2.5 µl of each reaction was added to 50 µl of NEB 10-beta competent cells (from New England Biolabs), heat shocked for 30 seconds at 42° C. and immediately placed on ice for 2 minutes. 950 µl of SOC was added per tube, transferred to a culture tube and incubated with rolling for 1 hr at 37° C. 100 µl of each transformation was plated onto LB Agar plates with 30 µg/mL kanamycin alone or with kanamycin and 100 µg/mL streptomycin or YEG Agar plates with 30 μg/mL and 10 mM chloro-phenylalanine (phenylalanine analog). 1:10 and 1:100 dilutions of the transformation culture were also plated.

TABLE 4

Varying Daughter Vector Fragment concentrations.

| Reaction | Mother polynucleotide (ng/20 ul) | Daughter Vector Fragment (ng/20 ul) | CFU/100 ul | CFU/10 ul | CFU/1 ul |
|---|---|---|---|---|---|
| 1 | 25 | 25 | >1000 | >1000 | 358 Yellow |
| 2 | 25 | 5 | >1000 | >1000 | 74 Yellow |
| 3 | 25 | 1 | >1000 | 177 Yellow | 19 Yellow |
| 4 | 25 | 0.2 | >1000 | 67 Yellow | 9 Yellow |
| 5 | 25 | 0.04 | 134 Yellow | 12 Yellow | 0 |
| 6 | 25 | 0.008 | 19 Yellow | 3 Yellow | 0 |
| 7 | 25 | 0.0016 | 1 Yellow | 1 Yellow | 0 |
| 8 | 25 | 0 | 0 | 0 | 0 |

Colonies were observed even at the lowest concentration of Daughter vector tested i.e. at 1.6 picograms per 20 ul reaction.

TABLE 5

Varying Mother Polynucleotide concentrations.

| Reaction | Mother polynucleotide (ng) | Daughter vector (ng) | CFU/100 ul | CFU/10 ul | CFU/1 ul |
|---|---|---|---|---|---|
| 9 | 25 | 25 | >1000 | >1000 | 308 Yellow |
| 10 | 5 | 25 | >1000 | >1000 | 154 Yellow |
| 11 | 1 | 25 | >1000 | 237 Yellow | 27 Yellow |
| 12 | 0.2 | 25 | >1000 | 79 Yellow | 5 Yellow |
| 13 | 0.04 | 25 | 155 Yellow | 18 Yellow | 0 |
| 14 | 0.008 | 25 | 36 Yellow | 0 | 0 |
| 15 | 0.0016 | 25 | 7 Yellow 3 White | 2 Yellow | 0 |
| 16 | 0 | 25 | 0 | 0 | 0 |

In a separate experiment, we varied the Mother Polynucleotide concentration while keeping the amount of Daughter Vector Fragment constant.

Daughter Vector Fragment 107892 was kept constant at 25 ng/20 ul reaction, Mother Polynucleotide 107889 concentrations were varied as shown in Table 5.

Colonies were observed even at the lowest concentration of Mother Polynucleotide tested i.e. at 1.6 picograms per 20 ul reaction. These results demonstrated that it is possible to get transformants with very low concentrations of Mother or Daughter vectors in the reaction. The transformants seen were all yellow indicating that the insert fragment from the Mother Polynucleotide ligated in the correct orientation into the Daughter Vector, without incorporation of any deleterious mutation.

In a separate experiment different amounts of enzyme were used to join Mother Polynucleotide 107889 (SEQ ID NO: 2) with Daughter Vector Fragment 107892 (SEQ ID NO: 3). Reactions contained 50 mM potassium acetate, 20 mM Tris-acetate, 10 mM magnesium acetate, 1 mM dithiothreitol, pH7.9 and 2.5 ng/μl Mother Polynucleotide and 2.5 ng/μl Daughter Vector Fragment and SapI and T4 DNA ligase as shown in Table 6. Reactions were transformed into competent NEB 10-Beta cells as described in examples above.

TABLE 6

Varying enzyme concentrations.

| SapI (units/10 ul) | T4 DNA ligase (units/10 ul) | CFU/100 ul | CFU/10 ul | CFU/1 ul |
|---|---|---|---|---|
| 0 | 0 | 3 White | NA | NA |
| 1 | 200 | >1000 | >1000 | 1 White, 488 Yellow |
| 0.5 | 100 | >1000 | >1000 | 1 White, 561 Yellow |
| 0.25 | 50 | >1000 | >1000 | 1 White, 261 Yellow |
| 0.125 | 25 | >1000 | >1000 | 3 White, 69 Yellow |
| 0.0625 | 12.5 | >1000 | 8 White, 72 Yellow | 8 yellow |
| 0.031 | 6.2 | 11 White, 62 Yellow | 3 White, 7 Yellow | 0 |
| 0.016 | 3.1 | 1 White, 3 Yellow | 0 | 0 |

As shown in Table 6, SapI concentrations as low as 3 units/ml and T4 DNA ligase concentrations as low as 620 units/ml produced good numbers of subcloned genes.

6.4 Cloning of PCR Product into Daughter Vectors

To determine if it was possible to clone a PCR product without any prior treatment or cleanup, into a daughter vector using the one pot reaction approach described in examples above, we amplified yellow fluorescent protein encoded by construct 107889 (SEQ ID NO: 1) using primers 107888A-ampF (SEQ ID NO: 6) and 107888A-ampR (SEQ IDS NO: 7). 4 PCR reactions were set up, each in a 50 μl reaction volume with 2.5 μl (3.0 ng) 107889 as template, 2.5 μl of each primer 107888A-ampF and 107888A-ampR at 10 μM each, 10 μl 5×PCR buffer, 1.7 μl 6 mM dNTPs (from Fermentas), 1 μl of a proof reader enzyme and 28.3 μl of water. Amplification was carried out in a thermal cycler as follows: Step 1: 45 seconds at 96° C., Step 2: 15 seconds at 96° C., Step 3: 15 seconds at 55° C., Step 4: 30 seconds at 72° C., Step 5: Go to Step 2 24 times, Step-6: 30 seconds at 72° C., Step 7: Hold at 4° C. 5 μl of each reaction was run on a 1% agarose-TBE gel. A strong and clean amplicon running at 750 bp was observed. Based on loading of 10 ul of NEB Quick-Load® 1 kb ladder, concentration of PCR reaction was estimated to be 100 ng/μl.

Cloning of PCR product into Daughter Vector Fragment 107892 was carried out as a one pot reaction. A 20 ul mixture containing 50 mM potassium acetate, 20 mM Tris-acetate, 10 mM magnesium acetate, 1 mM dithiothreitol, pH7.9, 20 ng of Daughter Vector Fragment 107892, 2 ul of PCR reaction (~200 ng of Mother Polynucleotide PCR product), 2 units SapI and 400 units T4 DNA ligase was incubated for 5 minutes at room temperature. Reactions with no enzyme added were set up as background controls. Transformation into NEB 10-beta competent cells was carried out as described in examples above and plated onto LB+Kanamycin plates. Plates were incubated at 37° C. for 24 hours.

TABLE 7

PCR cloning.

| PLATE | CFU/100 μl | CFU/10 μl | CFU/1 μl | no enzyme control CFU/100 μl |
|---|---|---|---|---|
| LB/Kan | >1000 | 3 white, 162 yellow | 1 white, 7 yellow | 0 |
| YEG/Kan | >1000 | >1000 | 11 yellow | 2 |

The results, shown in Table 7, demonstrate that PCR product can be cloned into a daughter vector without any PCR reaction cleanup, by incubating with SapI and T4 DNA ligase for 5 minutes at room temperature with a majority of transformants expressing yellow fluorescent protein. We expect that typeIIs/ligase-based cloning into a Daughter Vector will be possible for any PCR product where typeIIs sites have been added to incorporate suitable overhangs. This will allow efficient transfer of any open reading frame of interest into a variety of host expression systems using the approach described herein.

6.5 Multi-Part Assembly into Daughter Vectors (SapI Ends)

Assembly of multiple fragments into a Daughter vector to make a new insert that is scarless is possible using the method described herein. Yellow fluorescent protein fragments encoded by constructs 109629 (SEQ ID NO: 8) and 109630 (SEQ ID NO: 9) were cloned into Daughter vector 107892 (SEQ ID NO: 3). The two fragments have flanking SapI recognition sites that create compatible overhangs with each other and the ends of the daughter vector as shown in FIG. 7.

Four reactions were set up: each reaction was set up in a 10 µl reaction with 50 mM potassium acetate, 20 mM Tris-acetate, 10 mM magnesium acetate, 1 mM dithiothreitol, pH7.9, 1 mM ATP, 50 ng of Mother Polynucleotide 109629, 50 ng of Mother Polynucleotide 109630, 50 ng of Daughter Vector Fragment 107892, 0.5 units SapI and 100 units T4 DNA ligase. Buffer, ATP and enzymes were from New England Biolabs. Reactions 1 and 2 lacked one of the Mother Polynucleotides and reaction 4 contained all the components except enzyme. Incubation was carried out at room temperature (25 degrees Celsius) for 20 minutes. 2.5 µl of each reaction was transformed into NEB 10-Beta cells as described in examples above. 100 µl of undiluted culture as well as dilutions were plated on LB Agar+30 µg/ml Kanamycin. Results are shown in Table 8.

Only 10% of the colonies were yellow i.e. with the two fragments assembled together and ligating into the daughter vector to form a functional yellow fluorescent protein. A large percentage of white colonies observed suggest that the TTA overhang of fragment insert from 109629, generated upon digestion with SapI, is pseudo-compatible to the GGT overhang generated by SapI digestion of daughter vector 107892, forming a non-standard Watson-Crick base pairing, T with G in a way that can be joined by DNA ligase with reasonable efficiency (FIG. 7).

TABLE 8

Two part Mother Polynucleotide assembly

| Reaction | 109629 | 109630 | 107892 | CFU/100 ul | CFU/10 ul | CFU/1 ul |
|---|---|---|---|---|---|---|
| 1 | 50 ng | 0 | 50 ng | >1000 all white | NA | NA |
| 2 | 0 | 50 ng | 50 ng | 134 all white | NA | NA |
| 3 | 50 ng | 50 ng | 50 ng | >1000 (~10% are yellow) | ~1000 (105 yellow) | 106 white 9 yellow |
| 4 no enzyme control | 50 ng | 50 ng | 50 ng | 20 all white | NA | NA |

The reactions described above were repeated with new Mother Polynucleotides with Yellow fluorescent protein fragments encoded by constructs 110706 (SEQ NO: 10) and 110707 (SEQ NO: 11). The 3'-end of 110706 had a 5'-GGT-3' overhang, while the 5'-end of 110707 had a 5'-ACC-3' overhang. Results are shown in Table 9.

TABLE 9

Two part Mother Polynucleotide assembly

| Reaction | 110706 | 110707 | 107892 | CFU/100 ul | CFU/10 ul | CFU/1 ul |
|---|---|---|---|---|---|---|
| 1 | 25 ng | 0 | 25 ng | 55 White | NA | NA |
| 2 | 0 | 25 ng | 25 ng | 3 White | NA | NA |
| 3 | 25 ng | 25 ng | 25 ng | >1000 | >1000 | 95 White, 93 Yellow |
| 4 no enzyme mix control | 25 ng | 25 ng | 25 ng | 9 White | NA | NA |

In this experiment, we placed the same overhang (5'-ACC-3') at each end of the second Insert Fragment, and it could therefore ligate in either orientation. Accordingly, approximately 50% of transformants in this experiment were yellow, and approximately 50% of the transformants were white colonies. Sequencing confirmed that white colonies resulted from the second fragment ligating in the antisense direction.

We determined that it is therefore critically important to avoid ends that are either perfectly compatible or pseudo-compatible with other ends in the ligation, if ligation to those ends is not desired.

TABLE 10

Two part Mother Polynucleotide assemblyoverhang

| | YELLOW | WHITE | y % |
|---|---|---|---|
| GTA | 90 | 0 | 1.00 |
| ACA | 24 | 0 | 1.00 |
| ATA | 24 | 0 | 1.00 |
| GCA | 91 | 2 | 0.98 |
| TAC | 125 | 4 | 0.97 |
| CTT | 55 | 2 | 0.96 |
| TAT | 36 | 2 | 0.95 |
| AAT | 121 | 7 | 0.95 |
| ACG | 83 | 5 | 0.94 |
| CCT | 122 | 8 | 0.94 |
| CAG | 101 | 7 | 0.94 |
| AGC | 170 | 12 | 0.93 |
| GAC | 145 | 11 | 0.93 |
| CGT | 92 | 7 | 0.93 |
| TGC | 63 | 5 | 0.93 |
| GGA | 82 | 7 | 0.92 |
| CCC | 82 | 7 | 0.92 |
| CTG | 57 | 5 | 0.92 |
| AGA | 68 | 6 | 0.92 |
| CAA | 56 | 5 | 0.92 |
| GCG | 207 | 19 | 0.92 |
| GAA | 59 | 6 | 0.91 |
| CGA | 38 | 5 | 0.88 |
| TCC | 69 | 10 | 0.87 |
| AAG | 139 | 21 | 0.87 |
| AGG | 46 | 7 | 0.87 |
| CGC | 80 | 14 | 0.85 |
| GAT | 147 | 26 | 0.85 |
| CCG | 47 | 10 | 0.82 |
| GGG | 79 | 17 | 0.82 |
| TAG | 32 | 8 | 0.80 |
| TTG | 12 | 3 | 0.80 |
| TTA | 11 | 3 | 0.79 |
| CAC | 66 | 19 | 0.78 |
| AGT | 95 | 29 | 0.77 |
| AAC | 25 | 8 | 0.76 |
| CTA | 18 | 6 | 0.75 |
| CCA | 12 | 4 | 0.75 |
| TCA | 6 | 2 | 0.75 |
| TCG | 26 | 9 | 0.74 |
| GGC | 162 | 60 | 0.73 |

TABLE 10-continued

Two part Mother Polynucleotide assemblyoverhang

| | YELLOW | WHITE | y % |
|---|---|---|---|
| TGT | 26 | 11 | 0.70 |
| TTT | 9 | 5 | 0.64 |
| CTC | 50 | 28 | 0.64 |
| TGG | 16 | 11 | 0.59 |
| AAA | 7 | 5 | 0.58 |
| TGA | 5 | 4 | 0.56 |
| CGG | 21 | 20 | 0.51 |
| GAG | 26 | 25 | 0.51 |
| TAA | 1 | 5 | 0.17 |
| TCT | 0 | 2 | 0.00 |

When two Mother Polynucleotides are joined with each other and with a Daughter Vector Fragment, the overhang between the two Mother Polynucleotide Insert Fragments can significantly affect the yield of correctly assembled full-length genetic construct. To test this further we designed 52 pairs of Mother Polynucleotides, each comprising two recognition sequences for SapI. The Mother Polynucleotides also had the following properties. Following cleavage with SapI, the first member of each pair had a 5'-ACC-3' overhang at one end, and a different 3 base 5'-overhang at the other end. Following cleavage with SapI, the second member of each pair had a 5'-ATG-3' overhang at one end, and a 3 base 5'-overhang complementary to the first member of the pair at the other end. These overhangs are shown in Table 10. Ligation of the two members of each pair by joining at the complementary 3 bp overhangs produces a sequence comprising the sequence of YFP 107889 (SEQ ID NO: 1) with compatible ends to Daughter Vector Fragment 107892.

Each Mother Polynucleotide was created by PCR amplification using gene 107889 as a template. After amplification, for each pair of Mother Polynucleotides, a 10 ul reaction was set up containing 50 mM potassium acetate, 20 mM Tris-acetate, 10 mM magnesium acetate, 1 mM dithiothreitol, pH7.9, 1 mM ATP, 50 ng of Daughter Vector 107892 (NOT previously digested), 1 ul of the PCR reaction in which the first member of the pair was amplified, 1 ul of the PCR reaction in which the second member of the pair was amplified, 0.5 units SapI and 100 units T4 DNA ligase. The reaction was incubated for 15 minutes at 25° C. 2.5 µl of each reaction was transformed into NEB 10-Beta cells. 100 µl of culture was plated on LB Agar+30 µg/ml Kanamycin.

The results shown in Table 10 demonstrate that incubation of a Daughter Vector (comprising a counter-selectable marker, but not pre-digested with a restriction endonuclease) with DNA from PCR reactions (but not purified in any way) and a typeIIs restriction endonuclease and a DNA ligase can result in accurate and specific combining of 3 DNA fragments to create a single contiguous polynucleotide whose function depends on the order in which the DNA elements are assembled.

Table 10 shows that different overhangs joining two Insert Fragments have very different efficiencies of ligation when combined with a Daughter Vector Fragment carrying a 5'-TAC-3' overhang at one end and a 5'-GGT-3' overhang at the other end. The most efficiently ligated overhangs were 5'-GTA-3', 5'-ACA-3', 5'-ATA-3', 5'-GCA-3', 5'-TAC-3', 5'-CTT-3', 5'-TAT-3', 5'-AAT-3', 5'-ACG-3', 5'-CAG-3', 5'-AGC-3', 5'-GAC-3', 5'-CGT-3', 5'-TGC-3', 5'-GGA-3', 5'-CCC-3', 5'-CTG-3', 5'-AGA-3', 5'-CAA-3', 5'-GCG-3' and 5'-GAA-3'. The least efficiently ligated overhangs were 5'-TCT-3', 5'-TAA-3', 5'-GAG-3', 5'-CGG-3', 5'-TGA-3', 5'-AAA-3', 5'-TGG-3', 5'-CTC-3', 5'-TTT-3'.

When a Daughter Vector Fragment has overhangs comprising 5'-CAT-3' and 5'-GGT-3', and two or more Insert Fragments are to be ligated into the Daughter Vector Fragment, the most preferred overhangs for at least one junction between two Insert Fragments comprise 5'-GTA-3', 5'-ACA-3', 5'-ATA-3', 5'-GCA-3', 5'-TAC-3', 5'-CTT-3', 5'-TAT-3', 5'-AAT-3', 5'-ACG-3', 5'-CAG-3', 5'-AGC-3', 5'-GAC-3', 5'-CGT-3', 5'-TGC-3', 5'-GGA-3', 5'-CCC-3', 5'-CTG-3', 5'-AGA-3', 5'-CAA-3', 5'-GCG-3' and 5'-GAA-3; and the least preferred overhangs for at least one junction between two Insert Fragments comprise-5'-TCT-3', 5'-TAA-3', 5'-GAG-3', 5'-CGG-3', 5'-TGA-3', 5'-AAA-3', 5'-TGG-3', 5'-CTC-3' and 5'-TTT-3'.

6.6 Multi-Part Assembly into Daughter Vectors (BsaI Ends)

Multi-part assembly is possible using other typeIIs generated overhangs. We used Mother Polynucleotide 109632 (SEQ ID NO: 12) encoding a fragment of yellow fluorescent protein with flanking BsaI recognition sites and Mother Polynucleotide 109631 (SEQ ID NO: 13) encoding another fragment of yellow fluorescent protein to demonstrate assembly of the two fragments into a full length yellow fluorescent protein into Daughter Vector Fragment pJ441 (SEQ ID NO: 14), shown in FIG. 8.

Four reactions were set up: each reaction was set up in a 10 µl reaction with 50 mM potassium acetate, 20 mM Tris-acetate, 10 mM magnesium acetate, 1 mM dithiothreitol, pH7.9, 1 mM ATP, 50 ng of Mother Polynucleotide 109632, 50 ng of Mother Polynucleotide 109631, 50 ng of Daughter Vector Fragment pJ441, 2.5 units BsaI and 100 units T4 DNA ligase. Buffer, ATP and enzymes were from New England Biolabs. Reactions 1 and 2 lacked one of the Mother Polynucleotides and reaction 4 contained all the components except enzyme. Incubation was carried out at 37° C. for 60 minutes. 2.5 µl of each reaction was transformed into NEB 10-Beta cells as described in examples above. 100 µl of undiluted culture as well as dilutions were plated on LB Agar+30 µg/ml Kanamycin. Results are shown in Table 8.

Reactions were set up as described in example 6.4 and incubated at 37° C. in a thermocycler for 60 minutes, followed by 20 minutes at 65° C. 2.5 µl of each reaction was transformed into NEB 10-Beta cells and plated onto LB Agar+kanamycin plates as described in examples herein.

TABLE 11

Multi-part assembly into daughter vectors.

| Reaction | 109632 | 109633 | pJ441 | CFU/100 ul | CFU/10 ul | CFU/1 ul |
|---|---|---|---|---|---|---|
| 1 | 50 ng | 0 | 50 ng | 2 white | NA | NA |
| 2 | 0 | 50 ng | 50 ng | 7 white | NA | NA |
| 3 | 50 ng | 50 ng | 50 ng | 523 yellow, 1 white | 47 yellow, 1 white | 2 yellow |
| 4 no enzyme control | 50 ng | 50 ng | 50 ng | 4 white | NA | NA |

We observed a majority of yellow colonies with less than 10% of the colonies that are white indicating that the multi-part assembly of the yellow fluorescent protein to a full length polynucleotide and its expression in a daughter vector was successful.

7. References

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method of joining two or more polynucleotides to form a product polynucleotide, the method comprising incubating a mixture, wherein the mixture comprises:
 a) a first polynucleotide comprising a selectable marker and an open reading frame encoding a polypeptide and first and second typeIIs recognition sequences, each of seven nucleotides;
 b) a second polynucleotide, other than the first polynucleotide, comprising first and second typeIIs recognition sequences of seven nucleotides, a promoter and transcriptional terminator; or a vector fragment resulting from cleavage of the second polynucleotide by a type II enzyme recognizing the recognition sequences, the vector fragment comprising the promoter and transcriptional terminator between first and second overhangs;
 c) one or more typeIIs restriction endonucleases; and
 d) a DNA ligase;
 wherein recognition of the typeIIs recognition sequences in the first polynucleotide and the second polynucleotide, if not already cleaved into the vector fragment before forming the mixture, by the one or more typeIIs restriction endonucleases generates from the first polynucleotide an insert fragment with the open reading frame between first and second overhangs and without the selection marker, and the vector fragment, wherein the first overhang of the insert fragment is compatible with the first overhang of the vector fragment and the second overhang of the insert fragment is compatible with the second overhang of the vector fragment, wherein the compatible ends anneal and the ligase joins the insert fragment and the vector fragment forming the product polynucleotide with the open reading frame operably linked to the promoter and transcriptional terminator; wherein the first and second overhangs are start and stop codons, or one is a start or stop codon and the other is an ala or gly codon.

2. The method of claim 1, wherein the first polynucleotide further comprises a counter-selectable marker or a double-stranded break positioned outside the insert fragment.

3. The method of claim 1, wherein the first and second overhangs of the insert fragment are start and stop codons.

4. The method of claim 1, wherein one of the first and second overhangs of the insert fragment is a start or stop codon and the other is an alanine or glycine codon and the second polynucleotide encodes a polynucleotide expressed as fusion protein with the polypeptide encoded by the first polynucleotide.

5. The method of claim 1, wherein the second polynucleotide further comprises a counter-selectable marker absent in the vector fragment.

6. The method of claim 2 wherein the counter-selectable marker is selected from the group consisting of sacB, rpsL, tetAR, pheS, thyA, lacY, gata-1, ccdB, kid and barnase.

7. The method of claim 5 wherein the counter-selectable marker is selected from the group consisting of sacB, rpsL, tetAR, pheS, thyA, lacY, gata-1, ccdB, kid and barnase.

8. The method of claim 1, wherein the typeIIs restriction endonuclease with a seven-base recognition sequence and generating three-base overhangs is SapI or BsmBI or BspQI.

9. The method of claim 1, wherein the product polynucleotide lacks a recognition sequence for the one or more typeIIs restriction endonucleases.

10. The method of claim 1, wherein the one or more typeIIs restriction endonucleases are the same.

11. The method of claim 1, wherein the first polynucleotide is selected from the group consisting of vectors, expression vectors, plasmid vectors, cosmid vectors, artificial chromosomes, viral vectors, and adeno-associated viral vectors.

12. A method of producing a product polynucleotide comprising transforming the product polynucleotide prepared using the method of claim 1 into a host cell, growing the host cell under conditions that favor the growth of host cells containing the selectable marker and, optionally, isolating the product polynucleotide from the host cell.

13. A method of producing a product polynucleotide comprising transforming the product polynucleotide prepared using the method of claim 2 into a host cell, growing the host cell under conditions that select against host cells that contain the counter-selectable marker, and optionally, isolating the product polynucleotide from the host cell.

14. A kit comprising:
 a) an enzyme mixture comprising
  i) first typeIIs restriction endonuclease that recognizes a first typeIIs recognition sequence of seven bases to generate three base overhangs, and
  ii) a DNA ligase,
 b) a reaction buffer, and
 c) instructions for incubating the enzyme mixture, the reaction buffer, and the first polynucleotide and the second polynucleotide of claim 1 for a predetermined length of time, and transforming the mixture into a host cell.

15. The kit of claim 14 further comprising a first polynucleotide comprising a selectable marker and first and second typeIIs recognition sequences.

16. The method of claim 1 further comprising transforming the mixture into a host cell, and growing the host cell under conditions that select for the presence of a selectable marker.

* * * * *

```
                            SEQUENCE LISTING

<160> NUMBER OF SEQ ID NOS: 14

<210> SEQ ID NO 1
<211> LENGTH: 1700
<212> TYPE: DNA
<213> ORGANISM: Escherichia coli

<400> SEQUENCE: 1
tgtcactttg cttgatatat gagaattatt taaccttata aatgagaaaa aagcaacgca      60
ctttaaataa gatacgttgc tttttcgatt gatgaacacc tataattaaa ctattcatct     120
attatttatg attttttgta tatacaatat ttctagtttg ttaaagagaa ttaagaaaat     180
aaatctcgaa aataataaag ggaaaatcag tttttgatat caaaattata catgtcaacg     240
ataatacaaa atataataca aactataaga tgttatcagt atttattatg catttagaat     300
aggggaagtc ttcgctcttc tatgacggca ctgactgaag gcgcaaaact gttcgagaaa     360
gaaatcccat atatcactga gctggaaggt gacgttgaag gtatgaagtt tatcatcaag     420
ggtgaaggta ccggtgacgc gagcgtcggt aaagtggatg ctcagttcat ttgtaccacg     480
ggcgacgttc cggttccgtg gagcacgctg gtcaccacgc tgacgtatgg tgctcagtgc     540
tttgccaagt atccgcgcca cattgcggat ttcttcaaaa gctgcatgcc ggaaggttac     600
gtccaagagc gcaccatcac ctttgagggt gatggcgtgt tcaagacccg tgcggaagtc     660
acctttgaaa atggcagcgt gtacaaccgt gtaaaactga acggccaggg tttcaagaag     720
gacggccacg tgctgggcaa aaatctggag tttaacttta cccctcattg tttgtacatt     780
tggggtgacc aagcgaatca tggcctgaaa agcgcgttca aaatcatgca tgagatcacc     840
ggctccaaag aggatttcat tgttgccgat cacacccaaa tgaatacccc gattggtggt     900
ggtccggtgc acgtgccgga gtaccaccac attacgtatc atgttaccct gtctaaagac     960
gtcaccgatc accgtgacca tttgaacatt gttgaggtga tcaaggcagt tgacctggaa    1020
acgtaccgtt aaggtagaag agcgaagact aaaaagagtc gaataagggc gacacaaatc    1080
atgaaaaatt tatttgcttt gtgagcggat aacaattata ataggaggta aaaatggca    1140 acggtgaatc aattggtccg caagcctcgt gcacgcaaag tcgctaagtc taatgttccg    1200
gcactggaag cgtgcccgca gaagcgtggt gtttgcacgc gcgtttacac cacgaccccg    1260
aagaagccga atagcgccct gcgcaaggtg tgtcgcgtcc gcctgaccaa cggcttcgag    1320
gttaccagct atattggcgg cgaaggccac aacttgcagg agcacagcgt tattctgatc    1380
cgtggtggcc gtgtgaagga tctgccaggc gtccgttatc atactgtgcg cggtgccctg    1440
gactgtagcg gtgtgaagga tcgtaaacaa gcgcgttcga aatacggtgt aaaacgcccg    1500
aaagcgtaaa agggcgacac cccataatta gcccgggcga aaggcccagt ctttcgactg    1560
agcctttcgt tttatttgat gcctggcagt tccctactct cgcatgggga gtccccacac    1620
taccatcggc gctacggcgt ttcacttctg agttcggcat ggggtcaggt gggaccaccg    1680
cgctactgcc gccaggcaaa                                                1700

<210> SEQ ID NO 2
<211> LENGTH: 2333
<212> TYPE: DNA
```

<213> ORGANISM: Escherichia coli

<400> SEQUENCE: 2

```
tttgcctggc ggcagtagcg cggtggtccc acctgacccc atgccgaact cagaagtgaa    60
acgccgtagc gccgatggta gtgtggggac tccccatgcg agagtaggga actgccaggc   120
atcaaataaa acgaaaggct cagtcgaaag actgggcctt tcgcccgggc taattatggg   180
gtgtcgccct tattcgactc ggggaagtct tcgctcttct atgacggcac tgactgaagg   240
cgcaaaactg ttcgagaaag aaatcccata tatcactgag ctgaaggtg acgttgaagg    300
tatgaagttt atcatcaagg gtgaaggtac cggtgacgcg agcgtcggta agtggatgc    360
tcagttcatt tgtaccacgg gcgacgttcc ggttccgtgg agcacgctgg tcaccacgct   420
gacgtatggt gctcagtgct ttgccaagta tccgcgccac attgcggatt tcttcaaaag   480
ctgcatgccg aaggttacg tccaagagcg caccatcacc tttgagggtg atggcgtgtt    540
caagacccgt gcggaagtca cctttgaaaa tggcagcgtg tacaaccgtg taaaactgaa   600
cggccagggt ttcaagaagg acggccacgt gctgggcaaa atctggagt ttaactttac    660
ccctcattgt ttgtacattt ggggtgacca agcgaatcat ggcctgaaaa gcgcgttcaa   720
aatcatgcat gagatcaccg gctccaaaga ggatttcatt gttgccgatc acacccaaat   780
gaataccccg attggtggtg gtccggtgca cgtgccggag taccaccaca ttacgtatca   840
tgttaccctg tctaaagacg tcaccgatca ccgtgaccat ttgaacattg ttgaggtgat   900
caaggcagtt gacctggaaa cgtaccgtta aggtagaaga gcgaagacta aaagagtcg    960
aataagggcg acacattctg aaatgagctg ttgacaatta atcatccggc tcgtatatag  1020
gaggtaaaaa aatgtcccac ttggcggaat tggtagcgag cgcgaaagca gcaattagcc  1080
aggcaagcga cgtggcagcg ctggataatg tccgtgtgga gtatctgggt aaaaagggcc  1140
acctgacccct gcaaatgacg accttgcgtg agttgccgcc agaagaacgt ccggcagccg  1200
gtgcggtgat taatgaagcg aaagagcaag tgcaacaggc gctgaatgcc cgtaaggctg  1260
agctggagag cgctgcgctg aacgcgcgtt tggccgcaga aacgatcgac gtgagcctgc  1320
cgggtcgtcg tatcgagaac ggtggcctgc atccggttac gcgtaccatc gaccgcattg  1380
agagcttctt cggcgaactg ggtttttaccg tggcgacggg tccggagatc gaggatgact  1440
accacaactt cgacgctctg aacatcccgg gtcaccaccc agcacgtgcc gaccatgaca  1500
cctttttggtt cgatacgacc cgtctgctgc gtacccaaac ttccggtgtt cagatccgta  1560
ccatgaaagc ccagcagccg ccgattcgta ttatcgcgcc tggtcgcgtg tatcgcaacg  1620
attacgacca gacccacacc ccgatgttcc atcaaatgga aggcctgatt gttgatacga  1680
acatctcttt taccaatctg aaaggcaccc tgcatgattt cctgcgtaac ttttcgaag   1740
aggatctgca gattcgcttc cgtccgagct actttccgtt tacggagccg tcggcggaag  1800
ttgatgtcat gggtaagaat ggtaagtggc tggaagttct gggttgcggc atggttcacc  1860
cgaatgtcct gcgcaatgtc ggcattgacc ctgaggtcta cagcggcttt ggttttggta  1920
tgggtatgga gcgcctgact atgctgcgct atggcgttac cgatttgcgc agcttttcg   1980
aaaacgatct gcgcttcctg aaacaattca gtagaaggg cgacacaaaa tttattctaa   2040
atgcataata aatactgata acatcttata gtttgtatta tattttgtat tatcgttgac  2100
atgtataatt ttgatatcaa aaactgattt tcccttatt attttcgaga tttatttttct  2160
taattctctt taacaaacta gaaatattgt atatacaaaa aatcataaat aatagatgaa  2220
tagtttaatt ataggtgttc atcaatcgaa aaagcaacgt atcttattta aagtgcgttg  2280
```

-continued

| cttttttctc atttataagg ttaaataatt ctcatatatc aagcaaagtg aca | 2333 |

<210> SEQ ID NO 3
<211> LENGTH: 1659
<212> TYPE: DNA
<213> ORGANISM: Escherichia coli

<400> SEQUENCE: 3

| aaatcatgaa aaatttattt gctttgtgag cggataacaa ttataatatg tggaattgtg | 60 |
| agcgctcaca attccacaac ggtttccctc tagaaataat tttgtttaac ttttaaggag | 120 |
| gtaaaaaatg tgaagagctt atttgccgac taccttggtg atctcgcctt tcacgtagtg | 180 |
| gacaaattct tccaactgat ctgcgcgcga ggccaagcga tcttcttctt gtccaagata | 240 |
| agcctgtcta gcttcaagta tgacgggctg atactgggcc ggcaggcgct ccattgccca | 300 |
| gtcggcagcg acatccttcg gcgcgatttt gccggttact gcgctgtacc aaatgcggga | 360 |
| caacgtaagc actacatttc gctcatcgcc agcccagtcg ggcggcgagt tccatagcgt | 420 |
| taaggtttca tttagcgcct caaatagatc ctgttcagga accggatcaa agagttcctc | 480 |
| cgccgctgga cctaccaagg caacgctatg ttctcttgct tttgtcagca agatagccag | 540 |
| atcaatgtcg atcgtggctg gctcgaagat tcctgcaaga atgtcattgc gctgccattc | 600 |
| tccaaattgc agttcgcgct tagctggata acgccacgga atgatgtcgt cgtgcacaac | 660 |
| aatggtgact tctacagcgc ggaggatttc gctctctcca ggggaagccg aagtttccaa | 720 |
| aaggtcgttg atcaaagctc gccgcgttgt ttcatcaagc cttacggtca ccgtaaccag | 780 |
| caaatcaata tcactgtgtg gcttcaggcc gccatccact gcggagccgt acaaatgtac | 840 |
| ggccagcaac gtcggttcga gatggcgctc gatgacgcca actacctctg atagttgagt | 900 |
| cgatacttcg gcgatcaccg cttccctcat atgttttccc tccttatgtt aagcttactc | 960 |
| agttattata tcataaatat ctgtgtcaag aataaactcg gcttactaaa agccagataa | 1020 |
| cagtatgcat atttgcgcgc tgattttttgc ggtataagaa tatatactga tatgtatacc | 1080 |
| cgaagtatgt caaaaagagg tatgctatga agcagcgtat tacagtgaca gttgacagcg | 1140 |
| acagctatca gttgctcaag gcatatatga tgtcaatatc tccggtctgg taagcacaac | 1200 |
| catgcagaat gaagcccgtc gtctgcgtgc cgaacgctgg aaagcggaaa atcaggaagg | 1260 |
| gatggctgag gtcgcccggt ttattgaaat gaacggctct tttgctgacg agaacagggg | 1320 |
| ctggtgaaat gcagtttaag gtttacacct ataaagaga gagccgttat cgtctgtttg | 1380 |
| tggatgtaca gagtgatatt attgacacgc ccgggcgacg gatggtgatc ccctggcca | 1440 |
| gtgcacgtct gctgtcagat aaagtctccc gtgaacttta cccggtggtg catatcgggg | 1500 |
| atgaaagctg gcgcatgatg accaccgata tggccagtgt gccggtttcc gttatcgggg | 1560 |
| aagaagtggc tgatctcagc caccgcgaaa atgacatcaa aaacgccatt aacctgatgt | 1620 |
| tctggggaat ataagctctt caggttgacc ccaagggcg | 1659 |

<210> SEQ ID NO 4
<211> LENGTH: 1611
<212> TYPE: DNA
<213> ORGANISM: Escherichia coli

<400> SEQUENCE: 4

| gactggtcgt agggaagcca caacggtttc cctctagaaa taattttgtt taactataag | 60 |
| aaggagatat acatatgtga agagcttatt tgccgactac cttggtgatc tcgcctttca | 120 |

```
cgtagtggac aaattcttcc aactgatctg cgcgcgaggc caagcgatct tcttcttgtc    180
caagataagc ctgtctagct tcaagtatga cgggctgata ctgggccggc aggcgctcca    240
ttgcccagtc ggcagcgaca tccttcggcg cgattttgcc ggttactgcg ctgtaccaaa    300
tgcgggacaa cgtaagcact acatttcgct catcgccagc ccagtcgggc ggcgagttcc    360
atagcgttaa ggtttcattt agcgcctcaa atagatcctg ttcaggaacc ggatcaaaga    420
gttcctccgc cgctggacct accaaggcaa cgctatgttc tcttgctttt gtcagcaaga    480
tagccagatc aatgtcgatc gtggctggct cgaagattcc tgcaagaatg tcattgcgct    540
gccattctcc aaattgcagt tcgcgcttag ctggataacg ccacggaatg atgtcgtcgt    600
gcacaacaat ggtgacttct acagcgcgga ggatttcgct ctctccaggg gaagccgaag    660
tttccaaaag gtcgttgatc aaagctcgcc gcgttgtttc atcaagcctt acggtcaccg    720
taaccagcaa atcaatatca ctgtgtggct tcaggccgcc atccactgcg gagccgtaca    780
aatgtacggc cagcaacgtc ggttcgagat ggcgctcgat gacgccaact acctctgata    840
gttgagtcga tacttcggcg atcaccgctt ccctcatatg ttttcctcc ttatgttaag    900
cttactcagt tattatatca taaatatctg tgtcaagaat aaactcggct tactaaaagc    960
cagataacag tatgcatatt tgcgcgctga ttttgcggt ataagaatat atactgatat    1020
gtatacccga agtatgtcaa aaagaggtat gctatgaagc agcgtattac agtgacagtt    1080
gacagcgaca gctatcagtt gctcaaggca tatatgatgt caatatctcc ggtctggtaa    1140
gcacaaccat gcagaatgaa gcccgtcgtc tgcgtgccga acgctggaaa gcggaaaatc    1200
aggaagggat ggctgaggtc gcccggttta ttgaaatgaa cggctctttt gctgacgaga    1260
acaggggctg gtgaaatgca gtttaaggtt tacacctata aagagagag ccgttatcgt    1320
ctgtttgtgg atgtacagag tgatattatt gacacgcccg ggcgacggat ggtgatcccc    1380
ctggccagtg cacgtctgct gtcagataaa gtctcccgtg aactttaccc ggtggtgcat    1440
atcggggatg aaagctggcg catgatgacc accgatatgg ccagtgtgcc ggtttccgtt    1500
atcggggaag aagtggctga tctcagccac cgcgaaaatg acatcaaaaa cgccattaac    1560
ctgatgttct ggggaatata atgctcttca ggttagagcg ccgccaccg c              1611
```

<210> SEQ ID NO 5
<211> LENGTH: 236
<212> TYPE: PRT
<213> ORGANISM: Escherichia coli

<400> SEQUENCE: 5

Met Thr Ala Leu Thr Glu Gly Ala Lys Leu Phe Glu Lys Glu Ile Pro
1               5                   10                  15

Tyr Ile Thr Glu Leu Glu Gly Asp Val Glu Gly Met Lys Phe Ile Ile
            20                  25                  30

Lys Gly Glu Gly Thr Gly Asp Ala Ser Val Gly Lys Val Asp Ala Gln
        35                  40                  45

Phe Ile Cys Thr Thr Gly Asp Val Pro Val Pro Trp Ser Thr Leu Val
    50                  55                  60

Thr Thr Leu Thr Tyr Gly Ala Gln Cys Phe Ala Lys Tyr Pro Arg His
65                  70                  75                  80

Ile Ala Asp Phe Phe Lys Ser Cys Met Pro Glu Gly Tyr Val Gln Glu
                85                  90                  95

Arg Thr Ile Thr Phe Glu Gly Asp Gly Val Phe Lys Thr Arg Ala Glu
            100                 105                 110

Val Thr Phe Glu Asn Gly Ser Val Tyr Asn Arg Val Lys Leu Asn Gly
            115                 120                 125

Gln Gly Phe Lys Lys Asp Gly His Val Leu Gly Lys Asn Leu Glu Phe
        130                 135                 140

Asn Phe Thr Pro His Cys Leu Tyr Ile Trp Gly Asp Gln Ala Asn His
145                 150                 155                 160

Gly Leu Lys Ser Ala Phe Lys Ile Met His Glu Ile Thr Gly Ser Lys
                165                 170                 175

Glu Asp Phe Ile Val Ala Asp His Thr Gln Met Asn Thr Pro Ile Gly
            180                 185                 190

Gly Gly Pro Val His Val Pro Glu Tyr His His Ile Thr Tyr His Val
        195                 200                 205

Thr Leu Ser Lys Asp Val Thr Asp His Arg Asp His Leu Asn Ile Val
    210                 215                 220

Glu Val Ile Lys Ala Val Asp Leu Glu Thr Tyr Arg
225                 230                 235

<210> SEQ ID NO 6
<211> LENGTH: 77
<212> TYPE: DNA
<213> ORGANISM: Escherichia coli

<400> SEQUENCE: 6
tacacgtact tagtcgctga aggggaagtc ttcgctcttc tatgacggca ctgactgaag      60
gcgcaaaact gttcgag                                                    77

<210> SEQ ID NO 7
<211> LENGTH: 77
<212> TYPE: DNA
<213> ORGANISM: Escherichia coli

<400> SEQUENCE: 7
aggtacgaac tcgattgacg ttttttagtct tcgctcttct accttaacgg tacgtttcca    60
ggtcaactgc cttgatc                                                    77

<210> SEQ ID NO 8
<211> LENGTH: 367
<212> TYPE: DNA
<213> ORGANISM: Escherichia coli

<400> SEQUENCE: 8
gctcttctat gacggcactg actgaaggcg caaaactgtt cgagaaagaa atcccatata     60
tcactgagct ggaaggtgac gttgaaggta tgaagtttat catcaagggt gaaggtaccg    120
gtgacgcgag cgtcggtaaa gtggatgctc agttcatttg taccacgggc gacgttccgg    180
ttccgtggag cacgctggtc accacgctga cgtatggtgc tcagtgcttt gccaagtatc    240
cgcgccacat tgcggatttc ttcaaaagct gcatgccgga aggttacgtc caagagcgca    300
ccatcacctt tgagggtgat ggcgtgttca agacccgtgc ggaagtcacc tttgaaaata    360
gaagagc                                                              367

<210> SEQ ID NO 9
<211> LENGTH: 382
<212> TYPE: DNA
<213> ORGANISM: Escherichia coli

<400> SEQUENCE: 9
gctcttctaa tggcagcgtg tacaaccgtg taaaactgaa cggccagggt ttcaagaagg     60

```
acggccacgt gctgggcaaa atctggagt ttaactttac ccctcattgt ttgtacattt    120
ggggtgacca agcgaatcat ggcctgaaaa gcgcgttcaa atcatgcat gagatcaccg     180 gctccaaaga ggatttcatt gttgccgatc acccaaat gaatacccg attggtggtg      240 gtccggtgca cgtgccggag taccaccaca ttacgtatca tgttaccctg tctaaagacg   300
tcaccgatca ccgtgaccat ttgaacattg ttgaggtgat caaggcagtt gacctggaaa   360
cgtaccgtta aggtagaaga gc                                            382
```

<210> SEQ ID NO 10
<211> LENGTH: 358
<212> TYPE: DNA
<213> ORGANISM: Escherichia coli

<400> SEQUENCE: 10

```
gctcttctat gacggcactg actgaaggcg caaaactgtt cgagaaagaa atcccatata   60
tcactgagct ggaaggtgac gttgaaggta tgaagtttat catcaagggt gaaggtaccg   120
gtgacgcgag cgtcggtaaa gtggatgctc agttcatttg taccacgggc gacgttccgg   180
ttccgtggag cacgctggtc accacgctga cgtatggtgc tcagtgcttt gccaagtatc   240
cgcgccacat tgcggatttc ttcaaaagct gcatgccgga aggttacgtc caagagcgca   300
ccatcacctt tgagggtgat ggcgtgttca agacccgtgc ggaagtcacc agaagagc    358
```

<210> SEQ ID NO 11
<211> LENGTH: 391
<212> TYPE: DNA
<213> ORGANISM: Escherichia coli

<400> SEQUENCE: 11

```
gctcttctac ctttgaaaat ggcagcgtgt acaaccgtgt aaaactgaac ggccagggtt   60
tcaagaagga cggccacgtg ctgggcaaaa atctggagtt taactttacc cctcattgtt   120
tgtacatttg gggtgaccaa gcgaatcatg gcctgaaaag cgcgttcaaa atcatgcatg   180
agatcaccgg ctccaaagag gatttcattg ttgccgatca cccaaatg aatacccga     240 ttggtggtgg tccggtgcac gtgccggagt accaccacat tacgtatcat gttaccctgt   300
ctaaagacgt caccgatcac cgtgaccatt tgaacattgt tgaggtgatc aaggcagttg   360
acctggaaac gtaccgttaa ggtagaagag c                                  391
```

<210> SEQ ID NO 12
<211> LENGTH: 372
<212> TYPE: DNA
<213> ORGANISM: Escherichia coli

<400> SEQUENCE: 12

```
ggtctccttt taaggaggta aaaatgacg gcactgactg aaggcgcaaa actgttcgag    60
aaagaaatcc catatatcac tgagctggaa ggtgacgttg aaggtatgaa gtttatcatc   120
aagggtgaag gtaccggtga cgcgagcgtc ggtaaagtgg atgctcagtt catttgtacc   180
acgggcgacg ttccggttcc gtggagcacg ctggtcacca cgctgacgta tggtgctcag   240
tgctttgcca agtatccgcg ccacattgcg gatttcttca aaagctgcat gccgaaggt    300 tacgtccaag agcgcaccat cacctttgag ggtgatggcg tgttcaagac ccgtgcggaa   360
gtcaccgaga cc                                                       372
```

<210> SEQ ID NO 13

```
<211> LENGTH: 395
<212> TYPE: DNA
<213> ORGANISM: Escherichia coli

<400> SEQUENCE: 13
ggtctcgtca cctttgaaaa tggcagcgtg tacaaccgtg taaaactgaa cggccagggt    60
ttcaagaagg acggccacgt gctgggcaaa atctggagt ttaactttac ccctcattgt   120
ttgtacattt ggggtgacca agcgaatcat ggcctgaaaa gcgcgttcaa atcatgcat    180 gagatcaccg gctccaaaga ggatttcatt gttgccgatc acacccaaat gaatacccg    240 attggtggtg gtccggtgca cgtgccggag taccaccaca ttacgtatca tgttaccctg   300
tctaaagacg tcaccgatca ccgtgaccat ttgaacattg ttgaggtgat caaggcagtt   360
gacctggaaa cgtaccgtta aggtccccag agacc                              395

<210> SEQ ID NO 14
<211> LENGTH: 4034
<212> TYPE: DNA
<213> ORGANISM: Escherichia coli

<400> SEQUENCE: 14
ctcatgacca aaatcccttta acgtgagtta cgcgcgcgtc gttccactga gcgtcagacc    60
ccgtagaaaa gatcaaagga tcttcttgag atccttttttt tctgcgcgta atctgctgct   120
tgcaaacaaa aaaaccaccg ctaccagcgg tggtttgttt gccggatcaa gagctaccaa   180 ctcttttttcc gaaggtaact ggcttcagca gagcgcagat accaaatact gttcttctag   240
tgtagccgta gttagcccac cacttcaaga actctgtagc accgcctaca tacctcgctc   300
tgctaatcct gttaccagtg gctgctgcca gtggcgataa gtcgtgtctt accgggttgg   360
actcaagacg atagttaccg gataaggcgc agcggtcggg ctgaacgggg ggttcgtgca   420
cacagcccag cttggagcga acgacctaca ccgaactgag atacctacag cgtgagctat   480
gagaaagcgc cacgcttccc gaagggagaa aggcggacag gtatccggta agcggcaggg   540
tcggaacagg agagcgcacg agggagcttc caggggggaaa cgcctggtat ctttatagtc   600
ctgtcgggtt tcgccacctc tgacttgagc gtcgattttt tgtgatgctcg tcagggggggc   660 ggagcctatg gaaaaacgcc agcaacgcgg ccttttttacg gttcctggcc ttttgctggc   720
cttttgctca catgttcttt cctgcgttat cccctgattc tgtggataac cgtattaccg   780
cctttgagtg agctgatacc gctcgccgca gccgaacgac cgagcgcagc gagtcagtga   840
gcgaggaagc ggaaggcgag agtagggaac tgccaggcat caaactaagc agaaggcccc   900
tgacggatgg cctttttgcg tttctacaaa ctctttctgt gttgtaaaac gacggccagt   960
cttaagctcg ggcccctgg gcggttctga taacgagtaa tcgttaatcc gcaaataacg  1020
taaaaacccg cttcggcggg ttttttttatg gggggagttt agggaaagag catttgtcag  1080
aatatttaag ggcgcctgtc actttgcttg atatatgaga attatttaac cttataaatg  1140
agaaaaaagc aacgcacttt aaataagata cgttgctttt tcgattgatg aacacctata  1200
attaaactat tcatctatta tttatgattt tttgtatata caatatttct agtttgttaa  1260
agagaattaa gaaaataaat ctcgaaaata taaagggaa aatcagtttt tgatatcaaa  1320
attatacatg tcaacgataa tacaaaatat aatacaaact ataagatgtt atcagtattt  1380
attatgcatt tagaataaat tttgtgtcgc ccttaattgt gagcggataa caattacgag  1440
cttcatgcac agtgaaatca tgaaaaattt atttgctttg tgagcggata acaattataa  1500
tatgtggaat tgtgagcgct cacaattcca caacggtttc cctctagaaa taattttgtt  1560
```

```
taacttttcg agaccttagg aggtaaacat ggtaccgaat tctgtacagg cctgcagaga      1620
tctgagctcg ctagccgtcg acaagcttgc ggccgctaat gactcgagta agtaactaag      1680 gtctcaccccc aagggcgaca ccccctaatt agcccgggcg aaaggcccag tctttcgact     1740
gagcctttcg ttttatttga tgcctggcag ttccctactc tcgcatgggg agtccccaca      1800
ctaccatcgg cgctacggcg tttcacttct gagttcggca tggggtcagg tgggaccacc      1860
gcgctactgc cgccaggcaa acaaggggtg ttatgagcca tattcaggta taaatgggct      1920
cgcgataatg ttcagaattg gttaattggt tgtaacactg acccctattt gtttattttt      1980
ctaaatacat tcaaatatgt atccgctcat gagacaataa ccctgataaa tgcttcaata      2040
atattgaaaa aggaagaata tgagccatat tcaacgggaa acgtcgaggc cgcgattaaa      2100
ttccaacatg gatgctgatt tatatgggta taaatgggct cgcgataatg tcggcaatc      2160 aggtgcgaca atctatcgct tgtatgggaa gcccgatgcg ccagagttgt ttctgaaaca      2220
tggcaaaggt agcgttgcca atgatgttac agatgagatg gtcagactaa actggctgac      2280
ggaatttatg ccacttccga ccatcaagca ttttatccgt actcctgatg atgcatggtt      2340
actcaccact gcgatccccg gaaaaacagc gttccaggta ttagaagaat atcctgattc      2400
aggtgaaaat attgttgatg cgctggcagt gttcctgcgc cggttgcact cgattcctgt      2460
ttgtaattgt ccttttaaca gcgatcgcgt atttcgcctc gctcaggcgc aatcacgaat      2520
gaataacggt ttggttgatg cgagtgattt tgatgacgag cgtaatggct ggcctgttga      2580
acaagtctgg aaagaaatgc ataaactttt gccattctca ccggattcag tcgtcactca      2640
tggtgatttc tcacttgata accttatttt tgacgagggg aaattaatag gttgtattga      2700
tgttggacga gtcggaatcg cagaccgata ccaggatctt gccatcctat ggaactgcct      2760
cggtgagttt tctccttcat tacagaaacg gcttttcaa aaatatggta ttgataatcc      2820
tgatatgaat aaattgcagt ttcatttgat gctcgatgag ttttctaag cggcgcgcca      2880 tcgaatggcg caaaaccttt cgcggtatgg catgatagcg cccggaagag agtcaattca      2940
gggtggtgaa tatgaaacca gtaacgttat acgatgtcgc agagtatgcc ggtgtctctt      3000
atcagaccgt ttcccgcgtg gtgaaccagg ccagccacgt ttctgcgaaa acgcgggaaa      3060
aagtggaagc ggcgatggcg gagctgaatt acattcccaa ccgcgtggca caacaactgg      3120
cgggcaaaca gtcgttgctg attggcgttg ccacctccag tctggccctg cacgcgccgt      3180
cgcaaattgt cgcggcgatt aaatctcgcg ccgatcaact gggtgccagc gtggtggtgt      3240
cgatggtaga acgaagcggc gtcgaagcct gtaaagcggc ggtgcacaat cttctcgcgc      3300
aacgcgtcag tgggctgatc attaactatc cgctggatga ccaggatgcc attgctgtgg      3360
aagctgcctg cactaatgtt ccggcgttat ttcttgatgt ctctgaccag acacccatca      3420
acagtattat tttctcccat gaggacggta cgcgactggg cgtggagcat ctggtcgcat      3480
tgggtcacca gcaaatcgcg ctgttagcgg gcccattaag ttctgtctcg gcgcgtctgc      3540
gtctggctgg ctggcataaa tatctcactc gcaatcaaat tcagccgata gcggaacggg      3600
aaggcgactg gagtgccatg tccggttttc aacaaaccat gcaaatgctg aatgagggca      3660
tcgttcccac tgcgatgctg gttgccaacg atcagatggc gctgggcgca atgcgcgcca      3720
ttaccgagtc cgggctgcgc gttggtgcgg atatctcggt agtgggatac gacgataccg      3780
aagatagctc atgttatatc ccgccgttaa ccaccatcaa acaggatttt cgcctgctgg      3840
ggcaaaccag cgtggaccgc ttgctgcaac tctctcaggg ccaggcggtg aagggcaatc      3900
```

| | | | | | |
|---|---|---|---|---|---|
| agctgttgcc | agtctcactg | gtgaaaagaa | aaaccaccct | ggcgcccaat | acgcaaaccg | 3960 |
| cctctccccg | cgcgttggcc | gattcattaa | tgcagctggc | acgacaggtt | tcccgactgg | 4020 |
| aaagcgggca | gtga | | | | | 4034 |